(12) United States Patent
Sun et al.

(10) Patent No.: US 12,338,193 B2
(45) Date of Patent: Jun. 24, 2025

(54) METHODS FOR ENANTIOSELECTIVE PREPARATION OF CHIRAL TETRAARYLMETHANES

(71) Applicant: The Hong Kong University of Science and Technology, Hong Kong (CN)

(72) Inventors: Jianwei Sun, Hong Kong (CN); Xingguang Li, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 993 days.

(21) Appl. No.: 17/424,220

(22) PCT Filed: Jan. 2, 2020

(86) PCT No.: PCT/CN2020/070124
§ 371 (c)(1),
(2) Date: Jul. 20, 2021

(87) PCT Pub. No.: WO2020/156022
PCT Pub. Date: Aug. 6, 2020

(65) Prior Publication Data
US 2022/0112138 A1    Apr. 14, 2022

Related U.S. Application Data

(60) Provisional application No. 62/918,404, filed on Jan. 29, 2019.

(51) Int. Cl.
| | | |
|---|---|---|
| *C07D 207/32* | (2006.01) | |
| *B01J 31/02* | (2006.01) | |
| *C07B 53/00* | (2006.01) | |
| *C07D 209/08* | (2006.01) | |
| *C07D 403/06* | (2006.01) | |
| *C07D 409/06* | (2006.01) | |
| *C07D 413/14* | (2006.01) | |
| *C07D 417/06* | (2006.01) | |
| *C07D 417/14* | (2006.01) | |

(52) U.S. Cl.
CPC .......... *C07B 53/00* (2013.01); *B01J 31/0258* (2013.01); *C07D 207/32* (2013.01); *C07D 209/08* (2013.01); *C07D 403/06* (2013.01); *C07D 409/06* (2013.01); *C07D 413/14* (2013.01); *C07D 417/06* (2013.01); *C07D 417/14* (2013.01); *B01J 2531/0266* (2013.01)

(58) Field of Classification Search
CPC .. C07D 207/32; C07D 209/08; C07D 403/06; C07D 409/06; C07D 413/14; C07D 417/06; C07D 417/14; C07B 53/00
See application file for complete search history.

(56) References Cited

PUBLICATIONS

Dörwald, F. Zaragoza. Side Reactions in Organic Synthesis: A Guide to Successful Synthesis Design, Weinheim: WILEY-VCH Verlag Gmbh & Co. KGaA, 2005, Preface (Year: 2005).*
Gong et al. Org. Biomol. Chem. 2015, 13, 7993-8000 (Year: 2015).*
Li et al. Org. Lett. 2024, 26, 396-400 (Year: 2024).*
Li et al. Nature Catalysis 2020, 3, 1010-1019 (Year: 2020).*
Wang et al.; Catalytic asymmetric 1,6-Conjugate Addition of para-Quinone Methides: Formation of All-Carbon quaternary Stereocenters; Angewandte Chemie International Edition; Sep. 22, 2015; vol. 54, Issue 46; pp. 13711-13714.
Zhuo; Minghua Research of Enantioselective Synthesis of Triarylmethanes by Biaxially Chiral Imidodiphosphoric Acids Catalyzed Friedel-Crafts Reactions; Chinese Doctoral Dissertations Full-text Database, Engineering Science and Technology I; Aug. 15, 2016; No. 8 B014-106.

\* cited by examiner

*Primary Examiner* — Matthew P Coughlin
(74) *Attorney, Agent, or Firm* — S&F/WEHRW

(57) ABSTRACT

Provided herein are enantioselective organocatalytic methods for preparing chiral tetraaryl methanes.

13 Claims, 13 Drawing Sheets

| | | | |
|---|---|---|---|
| 5. |  R = H, = Cl, = SCF₃, | r.t. 12 h | No reaction |
| 6. | (1R)-(−)-10-Camphorsulfonic acid | -20 °C, 2 h | >95% yield, 2% ee |
| 8. | L(+)-Tartaric acid | 40 °C, 12 h | No reaction |
| 9. | Zr (acac)₄ (10 mol%)  (10 mol%) | rt, 12 h | No reaction |
| 10. | Ti(OPr$^i$)₄ (10 mol%)  (10 mol%) | rt, 12 h | No reaction |

| Entry | Solvent | Conv.(%) | Ee (%) |
|---|---|---|---|
| 1 | DCM | 100 | -96.1 (-96.4) |
| 2 | DCE | 96 | -91.9 |
| 3 | CHCl₃ | 54 | -96.3 (-96.2) |
| 4 | toluene | 83 | -79 |
| 5 | PhCF₃ | 100 | -75 |
| 6 | PhF | 98 | -85 |
| 7 | CCl₄ | 100 | -70 |
| 8 | Et₂O | 6 | -85 |
| 9 | PhCl | 96 | -79 |

| Entry | T (°C) | Conv.(%) | Yield | Ee (%) |
|---|---|---|---|---|
| 1 | rt | 95 | 92 | -96.6 |
| 2 | 0 | 42 | 40 | -95.6 |
| 3 | -20 | 0 | 10 | -94.8 |
| 4 | -40 | 0 | 0 | -- |

| Entry | x | t (h) | Conv.(%) | Yield (%) | Ee (%) |
| --- | --- | --- | --- | --- | --- |
| 1 | 10 | 24 | 100 | >99 | -95.5 |
| 2 | 7.5 | 24 | 100 | 98 | -95.8 |
| 3 | 5 | 24 | 100 | 97 | -95.8 |
| 4 | 2.5 | 24 | 54 | 55 | -96.0 |

| Entry | x | t (h) | Conv.(%) | Yield (%) | Ee (%) |
| --- | --- | --- | --- | --- | --- |
| 1 | 1.2 | 24 | 100 | 90 | -95.9 |
| 2 | 2 | 24 | 100 | >99 | -96.1 |
| 3 | 3 | 24 | 100 | >99 | -96.2 |
| 4 | 5 | 24 | 100 | 97 | -95.2 |

Reactions were performed with 1a (0.20 mmol, 1.0 equiv.), 2a (0.40 mmol, 2.0 equiv.), catalyst (10 mol %), and 7.5 mol% of A3 in DCE (4.0 mL) at 0 °C for 48 h. isolated yield. e.e. determined by chiral HPLC analysis. modification of conditions were noted under the product.

METHODS FOR ENANTIOSELECTIVE PREPARATION OF CHIRAL TETRAARYLMETHANES

CROSS-REFERENCE TO RELATED APPLICATIONS

This application claims the benefit of priority of U.S. Provisional Application No. 62/918,404, filed on Jan. 29, 2019, the contents of which being hereby incorporated by reference in their entirety for all purposes.

TECHNICAL FIELD

The present disclosure generally relates to the area of organic synthesis. More particularly, the present disclosures relates to methods useful for the enantioselective preparation of chiral tetraarylmethanes.

BACKGROUND

Tetraarylmethanes have attracted increasing attention in the fields of organic materials, pharmaceuticals, life sciences and supramolecular chemistry due to their applications, including optoelectronic devices, functional material frameworks, drug delivery, pharmaceuticals, and protein translocation detection.

Currently, there is no direct method for catalytic asymmetric construction of chiral tetraarylmethanes. Conventional methods require preparation of chiral tetraarylmethanes as a racemic mixture and separation of the enantiomers, which results in loss of the undesired enantiomer and purification steps. Catalytic enantioselective preparation of tetraarylmethanes has remained as an unmet, but highly desirable goal in synthetic organic chemistry. There thus exists a need for an enantioselective catalytic method for producing chiral tetraarylmethanes that overcomes the challenges described above.

SUMMARY

Provided herein are methods for preparing structurally diverse tetraarylmethanes in high yield and enantiomeric excess (ee) utilizing an organo-catalytic enantioselective electrophilic aromatic substitution reaction.

In a first aspect, provided herein is an enantioselective method for preparing a tetraarylmethane having Formula I:

$$\text{Ar}^3 \overset{\text{Ar}^1}{\underset{\text{Ar}^4}{\diagup\!\!\!\!\diagdown}} \text{Ar}^2 \quad \text{I}$$

wherein each of $Ar^1$, $Ar^2$, $Ar^3$, $Ar^4$ is independently aryl or heteroaryl;
the method comprising:
contacting a compound of Formula II:

$$\text{Ar}^3 \overset{\text{Ar}^1}{\underset{\text{Ar}^4}{\diagup\!\!\!\!\diagdown}} \text{OH} \quad \text{II}$$

with a heteroaromatic nucleophile in the presence of a chiral Brønsted acid under conditions that facilitate an electrophilic aromatic substitution reaction thereby forming the compound of Formula I, wherein the compound of Formula I is chiral.

In a first embodiment, provided herein is the method of the first aspect, wherein the tetraarylmethane has Formula Ia:

$$(R^1)_m\!\!-\!\!\underset{}{\bigcirc}\!\!\overset{\text{Ar}^1}{\underset{}{\diagup\!\!\!\!\diagdown}}\!\!\overset{\text{Ar}^2}{\underset{}{\bigcirc}}\!\!-\!\!(R^2)_n \quad \text{Ia}$$

wherein
each of m and n is independently selected from 1, 2, 3, or 4;
$Ar^1$ is aryl or heteroaryl;
$Ar^2$ is a heteroaryl;
$R^1$ and $R^2$ are each independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, $-OR^3$, $-OSi(R^3)_3$, $-O(C=O)R^3$, $-(C=O)OR^3$, $-O(C=O)OR^3$, $-(C=O)R^3$, $-N(R^4)_2$, $-N(R^4)(C=O)R^3$, $-(C=O)N(R^4)_2$, $-N(R^4)(C=O)N(R^4)_2$, $-N(R^4)(C=O)OR^3$, $-O(C=O)N(R^4)_2$, $-SR^3$, $-(S=O)R^3$, $-SO_2R^3$, $-SO_2N(R^4)_2$, $-N(R^4)SO_2R^3$, $-SeR^3$, $-P(R^3)_3$, $-P(OR^3)_3$, and $-(P=O)(OR^3)_3$; or two instances of $R^1$ taken together with the carbons to which they are attached form a 5-6 membered cycloalkyl, heterocycloalkyl, aryl, or heteroaryl; or two instances of $R^2$ taken together with the carbons to which they are attached form a 5-6 membered cycloalkyl, heterocycloalkyl, aryl, or heteroaryl;
$R^3$ is selected from the group consisting of hydrogen, alkyl, haloalkyl, perhaloalkyl, alkene, alkyne, cycloalkyl, heterocycloalkyl, aryl, araalkyl, and heteroaryl; and
$R^4$ for each instance is independently selected from the group consisting of hydrogen, alkyl, haloalkyl, perhaloalkyl, alkene, alkyne, cycloalkyl, heterocycloalkyl, aryl, araalkyl, and heteroaryl; or two instances of $R^4$ taken together with the nitrogen to which they are attached form a 3-6 membered heterocycloalkyl; or one instance of $R^3$ and one instance of $R^4$ taken together with the atoms to which they are attached form a 4-6 membered heterocycloalkyl; and the method comprises:
contacting a compound of Formula IIa:

$$(R^1)_m\!\!-\!\!\underset{}{\bigcirc}\!\!\overset{\text{Ar}^1}{\underset{}{\diagup\!\!\!\!\diagdown}}\!\!\overset{\text{OH}}{\underset{}{\bigcirc}}\!\!-\!\!(R^2)_n \quad \text{IIa}$$

with a heteroaromatic nucleophile in the presence of a chiral Brønsted acid under conditions that facilitate an electrophilic aromatic substitution reaction thereby forming the compound of Formula Ia.

In a second embodiment, provided herein is the method of the first aspect, wherein the chiral Brønsted acid is a chiral phosphoric acid.

In a third embodiment, provided herein is the method of the second embodiment of the first aspect, wherein the chiral phosphoric acid is represented by the Formula IIIa, Formula IIIb, Formula IIIc or Formula IIId:

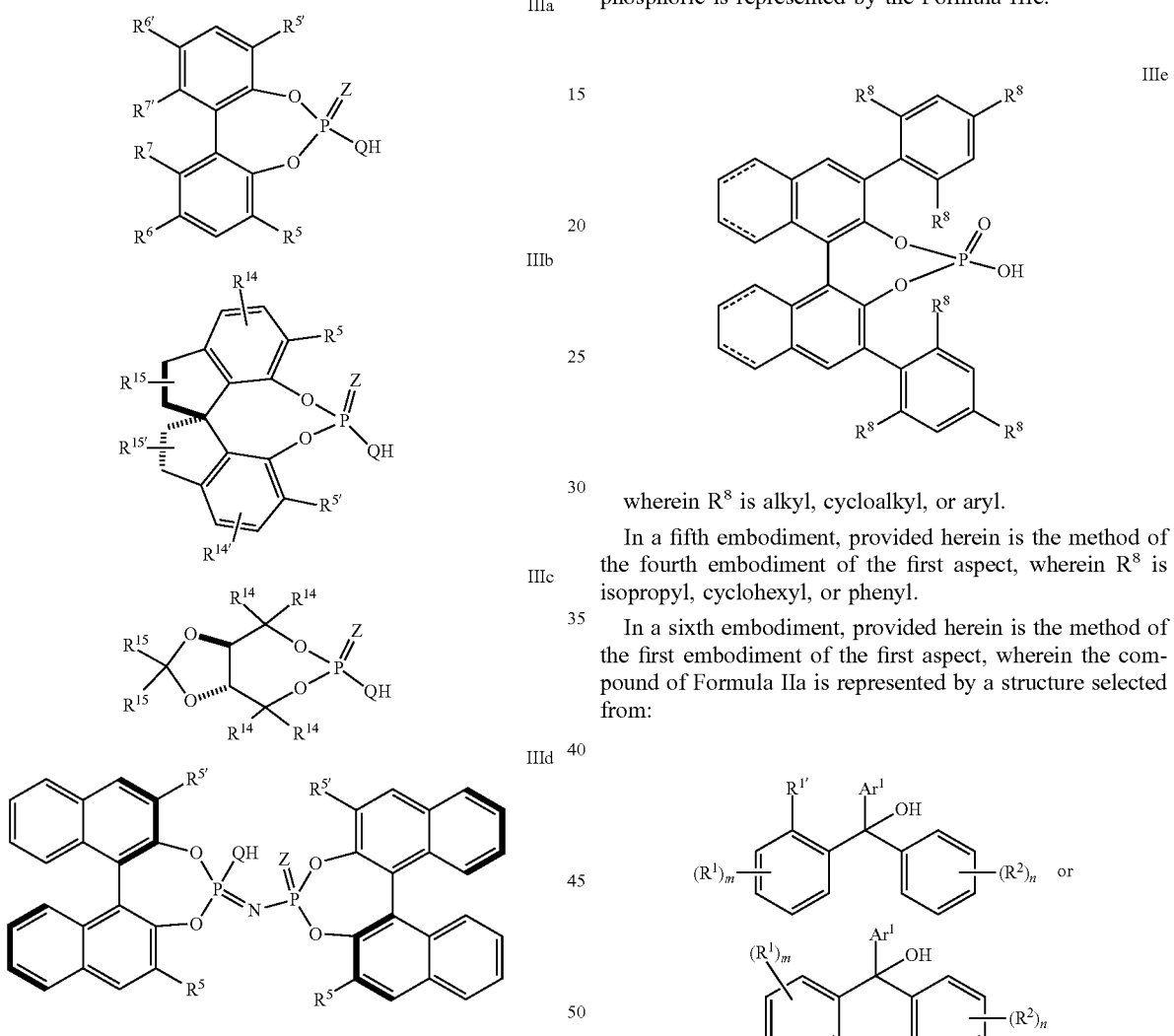

wherein Q is O, S, or $NSO_2R^{16}$;

Z is O, S, or Se;

each of $R^5$ and $R^{5'}$ is independently hydrogen, alkyl, haloalkyl, perhaloalkyl, cycloalkyl, heterocycloalkyl, aryl, araalkyl, heteroaryl, halide, or triarylsilane;

each of $R^6$ and $R^{6'}$ is independently hydrogen, alkyl, haloalkyl, perhaloalkyl, cycloalkyl, heterocycloalkyl, aryl, araalkyl, heteroaryl, halide, or trialkylsilane;

each of $R^7$ and $R^{7'}$ is independently alkyl, haloalkyl, perhaloalkyl, cycloalkyl, heterocycloalkyl, aryl, araalkyl, heteroaryl, halide, or trialkylsilane; or $R^{6'}$ and $R^{7'}$ taken together with the carbons to which they are attached form 5-6 membered cycloalkyl or 6 membered aryl and $R^6$ and $R^7$ taken together with the carbons to which they are attached form 5-6 membered cycloalkyl or 6 membered aryl;

each of $R^{14}$ and $R^{14'}$ is independently hydrogen, alkyl, haloalkyl, perhaloalkyl, cycloalkyl, heterocycloalkyl, aryl, araalkyl, heteroaryl, halide, or trialkylsilane;

each of $R^{15}$ and $R^{15'}$ is independently hydrogen, alkyl, haloalkyl, perhaloalkyl, cycloalkyl, heterocycloalkyl, aryl, araalkyl, heteroaryl, halide, or trialkylsilane; and $R^{16}$ is alkyl or aryl.

In a fourth embodiment, provided herein is the method of the third embodiment of the first aspect, wherein the chiral phosphoric is represented by the Formula IIIe:

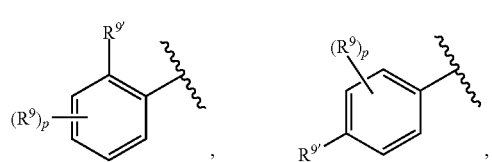

wherein $R^8$ is alkyl, cycloalkyl, or aryl.

In a fifth embodiment, provided herein is the method of the fourth embodiment of the first aspect, wherein $R^8$ is isopropyl, cyclohexyl, or phenyl.

In a sixth embodiment, provided herein is the method of the first embodiment of the first aspect, wherein the compound of Formula IIa is represented by a structure selected from:

wherein m is 0, 1, 2, or 3;

p is 0, 1, 2, or 3;

q is 0, 1, or 2;

$Ar^1$ is selected from the group consisting of:

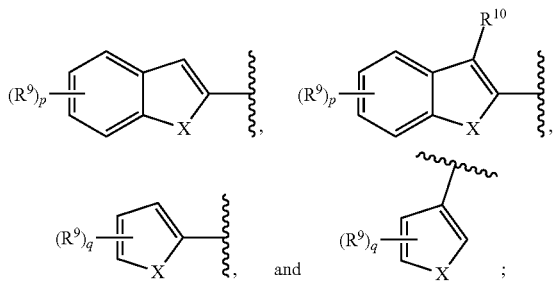

X is NR$^{11}$, O, S, or Se;

R$^1$ is selected from the group consisting of —OR$^3$, —OSi(R$^3$)$_3$, —O(C=O)R$^3$, —O(C=O)OR$^3$, —N(R$^4$)$_2$, —N(R$^4$)(C=O)R$^3$, —N(R$^4$)(C=O)N(R$^4$)$_2$, —N(R$^4$)(C=O)OR$^3$, —O(C=O)N(R$^4$)$_2$, —SR$^3$, —N(R$^4$)SO$_2$R$^3$, —SeR$^3$, —P(R$^3$)$_3$, and —P(OR$^3$)$_3$; or R$^{1'}$ and one instance of R$^1$ taken together with the carbons to which they are attached form a 5-6 membered cycloalkyl, heterocycloalkyl, aryl, or heteroaryl;

each R$^9$ is independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —OR$^3$, —OSi(R$^3$)$_3$, —O(C=O)R$^3$, —(C=O)OR$^3$, —O(C=O)OR$^3$, —(C=O)R$^3$, —N(R$^4$)$_2$, —N(R$^4$)(C=O)R$^3$, —(C=O)N(R$^4$)$_2$, —N(R$^4$)(C=O)N(R$^4$)$_2$, —N(R$^4$)(C=O)OR$^3$, —O(C=O)N(R$^4$)$_2$, —SR$^3$, —(S=O)R$^3$, —SO$_2$R$^3$, —SO$_2$N(R$^4$)$_2$, —N(R$^4$)SO$_2$R$^3$, —SeR$^3$, —P(R$^3$)$_3$, —P(OR$^3$)$_3$, and —(P=O)(OR$^3$)$_3$;

R$^{9'}$ is selected from the group consisting of —OR$^3$, —OSi(R$^3$)$_3$, —O(C=O)R$^3$, —O(C=O)OR$^3$, —N(R$^4$)$_2$, —N(R$^4$)(C=O)R$^3$, —N(R$^4$)(C=O)N(R$^4$)$_2$, —N(R$^4$)(C=O)OR$^3$, —O(C=O)N(R$^4$)$_2$, —SR$^3$, —N(R$^4$)SO$_2$R$^3$, —SeR$^3$, —P(R$^3$)$_3$, and —P(OR$^3$)$_3$; or two instances of R$^9$ taken together with the carbons to which they are attached form a 5-6 membered cycloalkyl, heterocycloalkyl, aryl, or heteroaryl; and R$^{10}$ is selected from the group consisting of alkyl, haloalkyl, perhaloalkyl, alkene, alkyne, cycloalkyl, heterocycloalkyl, aryl, araalkyl, heteroaryl, halide, —OR$^3$, —OSi(R$^3$)$_3$, —O(C=O)R$^3$, —O(C=O)OR$^3$, —N(R$^4$)$_2$, —N(R$^4$)(C=O)R$^3$, —N(R$^4$)(C=O)N(R$^4$)$_2$, —N(R$^4$)(C=O)OR$^3$, —O(C=O)N(R$^4$)$_2$, —SR$^3$, —N(R$^4$)SO$_2$R$^3$, or —SeR$^3$; and R$^{11}$ is hydrogen, alkyl, haloalkyl, perhaloalkyl, alkene, alkyne, cycloalkyl, heterocycloalkyl, aryl, araalkyl, heteroaryl, —(C=O)OR$^3$, —(C=O)R$^3$, —(C=O)N(R$^4$)$_2$, —SO$_2$R$^3$, or —SO$_2$N(R$^4$)$_2$.

In a seventh embodiment, provided herein is the method of the sixth embodiment of the first aspect, wherein Ar$^1$ is selected from the group consisting of:

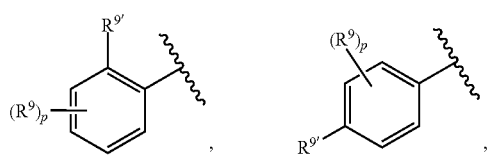

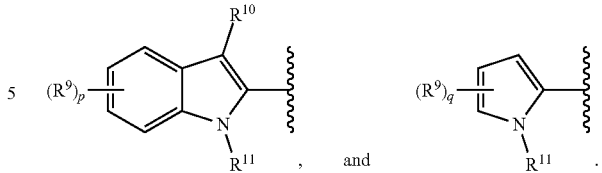

In an eighth embodiment, provided herein is the method of the first embodiment of the first aspect, wherein the heteroaromatic nucleophile is represented by the Formula IV:

wherein t is 0, 1, 2, or 3;

Y is NR$^{13}$, O, S, or Se;

each R$^{12}$ is independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —OR$^3$, —OSi(R$^3$)$_3$, —O(C=O)R$^3$, —(C=O)OR$^3$, —O(C=O)OR$^3$, —(C=O)R$^3$, —N(R$^4$)$_2$, —N(R$^4$)(C=O)R$^3$, —(C=O)N(R$^4$)$_2$, —N(R$^4$)(C=O)N(R$^4$)$_2$, —N(R$^4$)(C=O)OR$^3$, —O(C=O)N(R$^4$)$_2$, —SR$^3$, —(S=O)R$^3$, —SO$_2$R$^3$, —SO$_2$N(R$^4$)$_2$, —N(R$^4$)SO$_2$R$^3$, —SeR$^3$, —P(R$^3$)$_3$, —P(OR$^3$)$_3$, and —(P=O)(OR$^3$)$_3$; or two instances of R$^{12}$ taken together with the carbons to which they are attached form a 5-6 membered cycloalkyl, heterocycloalkyl, aryl, or heteroaryl; and R$^{13}$ is hydrogen, alkyl, haloalkyl, perhaloalkyl, alkene, alkyne, cycloalkyl, heterocycloalkyl, aryl, araalkyl, heteroaryl, —(C=O)OR$^3$, —(C=O)R$^3$, —(C=O)N(R$^4$)$_2$, —SO$_2$R$^3$, or —SO$_2$N(R$^4$)$_2$.

In a ninth embodiment, provided herein is the method of the eighth embodiment of the first aspect, wherein Y is NR$^{13}$;

each R$^{12}$ is independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —OR$^3$, —OSi(R$^3$)$_3$, —O(C=O)R$^3$, —O(C=O)OR$^3$, —N(R$^4$)$_2$, —N(R$^4$)(C=O)R$^3$—N(R$^4$)(C=O)N(R$^4$)$_2$, —N(R$^4$)(C=O)OR$^3$, —O(C=O)N(R$^4$)$_2$, —SR$^3$, —SO$_2$N(R$^4$)$_2$, —N(R$^4$)SO$_2$R$^3$, and —SeR$^3$; or two instances of R$^{12}$ taken together with the carbons to which they are attached form a 6 membered cycloalkyl or aryl; and R$^{13}$ is hydrogen, alkyl, haloalkyl, perhaloalkyl, alkene, alkyne, cycloalkyl, heterocycloalkyl, aryl, araalkyl, or heteroaryl.

In a tenth embodiment, provided herein is the method of the first embodiment of the first aspect, wherein the compound of Formula IIa is represented by a structure selected from:

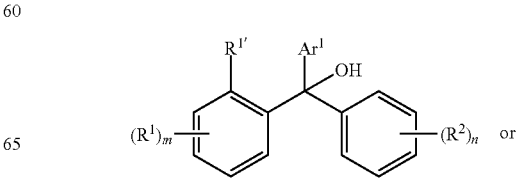

-continued

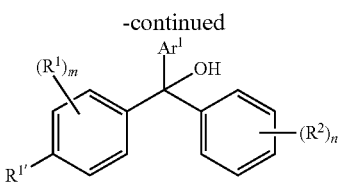

wherein m is 0, 1, 2, or 3;

p is 0, 1, 2, or 3;

q is 0, 1, or 2;

Ar¹ is selected from the group consisting of:

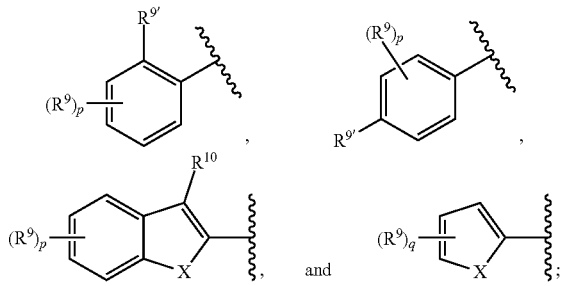

X is S or NR¹¹;

R¹' is selected from the group consisting of —OR³, —OSi(R³)$_3$, —O(C=O)R³, —O(C=O)OR³, —N(R⁴)$_2$, —N(R⁴)(C=O)R³, —N(R⁴)(C=O)N(R⁴)$_2$, —N(R⁴)(C=O)OR³, —O(C=O)N(R⁴)$_2$, —SR³, —N(R⁴)SO$_2$R³, —SeR³, —P(R³)$_3$, and —P(OR³)$_3$; or R¹' and one instance of R¹ taken together with the carbons to which they are attached form a 5-6 membered cycloalkyl, heterocycloalkyl, aryl, or heteroaryl;

each R⁹ is independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —OR³, —OSi(R³)$_3$, —O(C=O)R³, —(C=O)OR³, —O(C=O)OR³, —(C=O)R³, —N(R⁴)$_2$, —N(R⁴)(C=O)R³, —(C=O)N(R⁴)$_2$, —N(R⁴)(C=O)N(R⁴)$_2$, —N(R⁴)(C=O)OR³, —O(C=O)N(R⁴)$_2$, —SR³, —(S=O)R³, —SO$_2$R³, —SO$_2$N(R⁴)$_2$, —N(R⁴)SO$_2$R³, —SeR³, —P(R³)$_3$, —P(OR³)$_3$, and —(P=O)(OR³)$_3$;

R⁹' is selected from the group consisting of —OR³, —OSi(R³)$_3$, —O(C=O)R³, —O(C=O)OR³, —N(R⁴)$_2$, —N(R⁴)(C=O)R³, —N(R⁴)(C=O)N(R⁴)$_2$, —N(R⁴)(C=O)OR³, —O(C=O)N(R⁴)$_2$, —SR³, —N(R⁴)SO$_2$R³, —SeR³, —P(R³)$_3$, and —P(OR³)$_3$; or two instances of R⁹ taken together with the carbons to which they are attached form a 5-6 membered cycloalkyl, aryl, or heteroaryl; and R¹⁰ is selected from the group consisting of alkyl, haloalkyl, perhaloalkyl, cycloalkyl, heterocycloalkyl, aryl, araalkyl, heteroaryl, and halide; and R¹¹ is hydrogen, alkyl, haloalkyl, perhaloalkyl, alkene, alkyne, cycloalkyl, heterocycloalkyl, aryl, araalkyl, or heteroaryl; and the heteroaromatic nucleophile is represented by the Formula IV:

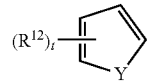

IV wherein t is 0, 1, 2, or 3;

Y is NR¹³;

each R¹² is independently selected from the group consisting of hydrogen, alkyl, haloalkyl, perhaloalkyl, alkene, alkyne, cycloalkyl, heterocycloalkyl, aryl, araalkyl, heteroaryl, halide, azide, —OR³, —OSi(R³)$_3$, —O(C=O)R³, —O(C=O)OR³, —N(R⁴)$_2$, —N(R⁴)(C=O)R³, —N(R⁴)(C=O)N(R⁴)$_2$, —N(R⁴)(C=O)OR³, —O(C=O)N(R⁴)$_2$, —SR³, —N(R⁴)SO$_2$R³, —SeR³, —P(R³)$_3$, and —P(OR³)$_3$; or two instances of R¹² taken together with the carbons to which they are attached form a 5-6 membered cycloalkyl, heterocycloalkyl, aryl, or heteroaryl; and R¹³ is hydrogen, alkyl, haloalkyl, perhaloalkyl, alkene, alkyne, cycloalkyl, heterocycloalkyl, aryl, araalkyl, or heteroaryl.

In an eleventh embodiment, provided herein is the method of the tenth embodiment of the first aspect, wherein m is 0 or 1; R¹ is —OR³, —OSi(R³)$_3$, —O(C=O)R³, —O(C=O)OR³, or —O(C=O)N(R⁴)$_2$;

Ar¹ is selected from the group consisting of:

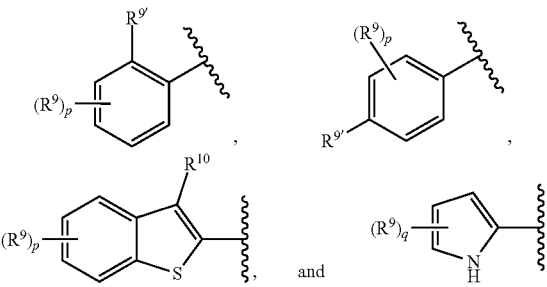

wherein p is 0 or 1;

q is 0 or 1;

R⁹' is selected from the group consisting of —OR³, —OSi(R³)$_3$, —O(C=O)R³, —O(C=O)OR³, or —O(C=O)N(R⁴)$_2$; and R¹⁰ is aryl; and the heteroaromatic nucleophile is selected from:

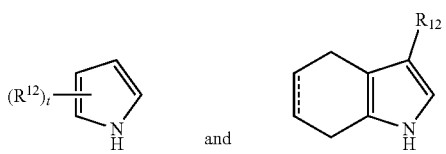

wherein t is 0 or 1; and each R¹² is independently selected from the group consisting of hydrogen, alkyl, haloalkyl, perhaloalkyl, alkene, alkyne, cycloalkyl, heterocycloalkyl, aryl, araalkyl, heteroaryl, halide, azide, —OR³, —OSi(R³)$_3$, —O(C=O)R³, —O(C=O)OR³, —N(R⁴)$_2$, —N(R⁴)(C=O)R³, —N(R⁴)(C=O)N(R⁴)$_2$, —N(R⁴)(C=O)

$OR^3$, $-O(C=O)N(R^4)_2$, $-SR^3$, $-N(R^4)SO_2R^3$, $-SeR^3$, $-P(R^3)_3$, and $-P(OR^3)_3$; or two instances of $R^{12}$ taken together with the carbons to which they are attached form a 5-6 membered cycloalkyl, heterocycloalkyl, aryl, or heteroaryl.

In a twelfth embodiment, provided herein is the method of the eleventh embodiment of the first aspect, wherein the chiral Brønsted acid is represented by the Formula IIIf or Formula IIIg:

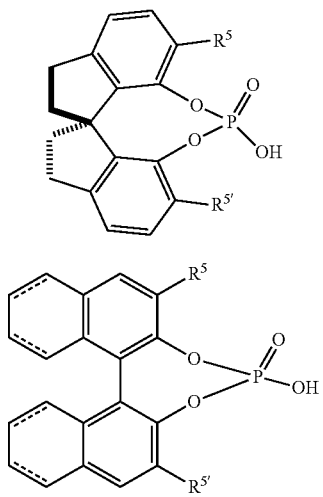

IIIf

IIIg wherein each of $R^5$ and $R^{5'}$ is alkyl, aryl, or triarylsilane.

In a thirteenth embodiment, provided herein is the method of the twelfth embodiment of the first aspect, wherein $R^5$ is 2,4,6-(iPr)$_3$C$_6$H$_2$—, 2,4,6-Cy$_3$C$_6$H$_2$—, 1-napthyl, 9-anthryl, 9-phenanthryl, 1-pyrene, or 2,6-iPr$_2$-6-(9-anthryl).

In a fourteenth embodiment, provided herein is the method of the first aspect, wherein the step of contacting a compound of Formula II with a heteroaromatic nucleophile in the presence of a chiral Brønsted acid occurs in a solvent selected from the group consisting of chlorobenzene, PhCF$_3$, PhF, CCl$_4$, CH$_2$Cl$_2$ (DCM), CHCl$_3$, PhMe, and ClCH$_2$CH$_2$Cl (DCE).

In a fifteenth embodiment, provided herein is the method of the first aspect, wherein the chiral Brønsted acid is present at a mole concentration of between 0.1% and 25% relative to the compound of Formula II.

In a sixteenth embodiment, provided herein is the method of the first aspect, wherein the step of contacting a compound of Formula II with a heteroaromatic nucleophile in the presence of a chiral Brønsted acid occurs at a temperature between −30° C. and 40° C.

In a seventeenth embodiment, provided herein is the method of the first aspect, wherein the tetraarylmethane having Formula I is prepared with an enantiomeric excess (ee) between 40 to 99.9%.

In an eighteenth embodiment, provided herein is the method of the ninth embodiment of the first aspect, wherein the tetraarylmethane having Formula I is prepared with an ee of 80 to 97%

In a nineteenth embodiment, provided herein is the method of the first aspect, wherein the compound of Formula II is a racemic mixture.

BRIEF DESCRIPTION OF DRAWINGS

The above and other objects and features of the present disclosure will become apparent from the following description of the disclosure, when taken in conjunction with the accompanying drawings, in which.

DETAILED DESCRIPTION

Definitions

Figure 1A:
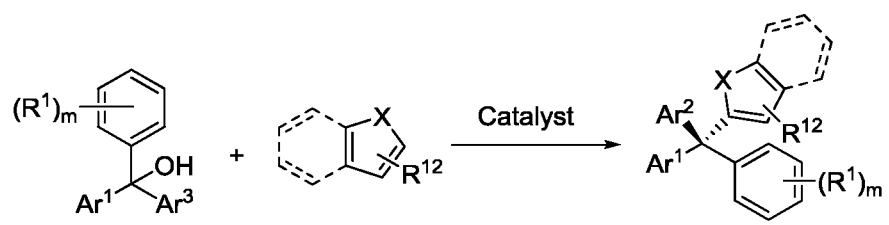
FIG. 1A depicts an exemplary enantioselective electrophilic aromatic substitution reaction in accordance with certain embodiments of the methods described herein.
Figure 1B:
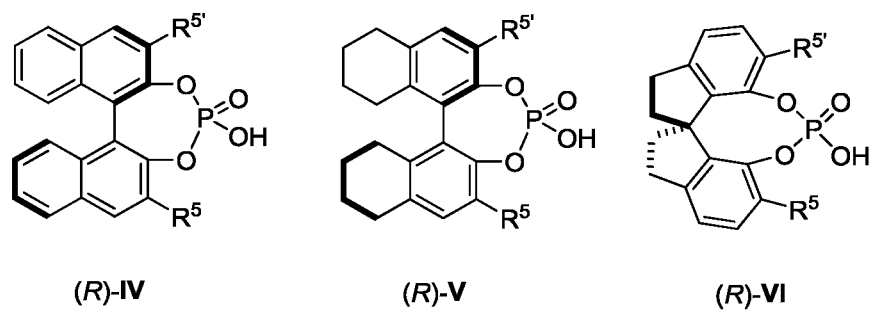
FIG. 1B depicts the chemical structures of exemplary chiral Brønsted acids useful as catalysts in accordance with certain embodiments of the methods described herein.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

The term "aralkyl" is art-recognized and refers to an alkyl group substituted with an aryl group (e.g., an aromatic or heteroaromatic group).

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bi cyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalky 1/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be optionally substituted as described herein. The aryl ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C$_6$F$_5$), are included within the definition of "haloaryl." In certain embodiments, an aryl group is substituted with another aryl group and can be referred to as a biaryl group. Each of the aryl groups in the biaryl group can be optionally substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine Noxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be optionally substituted as described herein. The heterocyclic ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "optionally substituted" refers to a chemical group, such as alkyl, cycloalkyl, aryl, heteroaryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like The representation "1" as used herein in connection to chemical a group or moiety is intended to represent the covalent bond that the aforementioned chemical group or moiety is covalently bonded to another chemical group or moiety.

At various places in the present specification, substituents of compounds are disclosed in groups or in ranges. It is specifically intended that the description include each and every individual sub-combination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-4 substituents" is specifically intended to individually disclose a chemical group that can include 0, 1, 2, 3, 4, 0-4, 0-3, 0-2, 0-1, 1-4, 1-3, 1-2, 2-4, 2-3, and 3-4 substituents.

"Enantiomers" are a pair of stereoisomers that are non-superimposable mirror images of each other. A mixture of a pair of enantiomers in equal proportions can be known as a "racemic" mixture. The term "(+/−)" is used to designate a racemic mixture where appropriate. The absolute stereochemistry can be specified according to the Cahn-Ingold-Prelog R-S system. When a compound is an enantiomer, the stereochemistry at each chiral carbon and/or axis of chirality can be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein can contain one or more asymmetric centers and/or axis of chirality and can thus give rise to enantiomers, diastereomers, and other stereoisomeric forms that can be defined, in terms of absolute stereochemistry at each asymmetric atom or axis of chirality, as (R)- or (S)-. The present compounds and methods are meant to include all such possible isomers, including substantially enantiopure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., an S enantiomer, and 10% of the other enantiomer, e.g., an R enantiomer. ee=(90-10)/100=80%.

Thus, a composition containing 90% of one enantiomer and 10% of the other enantiomer is said to have an enantiomeric excess of 80%. Some compositions described herein contain an enantiomeric excess of at least about 1%, about 5%, about 10%, about 20%, about 30%, about 40%, about 50%, about 75%, about 90%, about 95%, about 99%, or greater of the S enantiomer. In other words, the compositions contain an enantiomeric excess of the S enantiomer over the R enantiomer. In other embodiments, some compositions described herein contain an enantiomeric excess of at least about 1%, about 5%, about 10%, about 20%, about 30%, about 40%, about 50%, about 75%, about 90%, about 95%, about 99%, or greater of the R enantiomer. In other words, the compositions contain an enantiomeric excess of the R enantiomer over the S enantiomer.

For instance, an enantiomer can, in some embodiments, be provided substantially free of the corresponding enantiomer, and can also be referred to as "optically enriched," "enantiomerically enriched," "enantiomerically pure", "substantially enantiopure" and "non-racemic," as used interchangeably herein. These terms refer to compositions in which the amount of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the total weight of the preparation (e.g., total weight of S and R isomers), such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 70% by weight of one enantiomer relative to the total weight of the preparation, such as at as at least about 75% by weight, such as at as at least about 80% by weight, such as at as at least about 85% by weight, such as at least about 90% by weight, and such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R) isomers. In other embodiments, provided herein is a mixture of compounds wherein individual compounds of the mixture exist predominately in an (S)- or (R)-isomeric configuration. For example, in some embodiments, the compound mixture has an (S)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (S)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (S)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture has an (R)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (R)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (R)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

Provided herein is an enantioselective method for preparing a tetraarylmethane having Formula I:

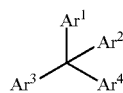

I wherein each of $Ar^1$, $Ar^2$, $Ar^3$, $Ar^4$ is independently aryl or heteroaryl;

the method comprising:

contacting a compound of Formula II:

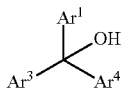

II with a heteroaromatic nucleophile in the presence of a chiral Brønsted acid under conditions that facilitate an electrophilic aromatic substitution reaction of the heteroaromatic nucleophile thereby forming the compound of Formula I. In certain embodiments, the compound of Formula I prepared according to the methods described herein is chiral, i.e., the structure of $Ar^1 \neq Ar^2 \neq Ar^3 \neq Ar^4$ and is in optically enriched form. Advantageously, as the electrophilic aromatic substitution reaction is believed to proceed through a triaryl methane carbocation, the compound of Formula II can be in racemic or enantiomerically enriched form.

In certain embodiments, $Ar^1$, $Ar^3$, and $Ar^4$ are selected from the group consisting of optionally substituted phenyl, optionally substituted furyl, optionally substituted pyrrolyl, optionally substituted pyrazolyl, optionally substituted thienyl, optionally substituted indolyl, optionally substituted imidazyl, optionally substituted thiazolyl, optionally substituted isothiazolyl, optionally substituted oxazolyl, optionally substituted isooxazolyl, optionally substituted benzofuranyl, optionally substituted indolyl, optionally substituted isoindolyl, optionally substituted benzothiophenyl, optionally substituted 1,3-benzodioxolyl, optionally substituted benzopyrazolyl, optionally substituted benzoimidazyl, optionally substituted benzothiazolyl, optionally substituted benzoisothiazolyl, optionally substituted benzooxazolyl, optionally substituted benzoisooxazolyl, optionally substituted napthyl, substituted anthracenyl, optionally substituted phenoaxazinyl, optionally substituted phenothiazinyl, optionally substituted isoquinolyl, optionally substituted quinoxalyl, optionally substituted quinazolyl, optionally substituted benzotriazolyl, optionally substituted benzimidazolyl, optionally substituted benzothiazolyl, optionally substituted benzisothiazolyl, optionally substituted benzisoxazolyl, optionally substituted benzoxadiazolyl, cinnobnyl, optionally substituted 1H-indazolyl, optionally substituted 2H-indazolyl, optionally substituted indolizinyl, optionally substituted isobenzofuyl, optionally substituted naphthyridinyl, optionally substituted phthalazinyl, optionally substituted pteridinyl, optionally substituted purinyl, optionally substituted oxazolopyridinyl, optionally substituted thiazolopyridinyl, optionally substituted imidazopyridinyl, optionally substituted furopyridinyl, optionally substituted thienopyridinyl, optionally substituted pyridopyrimidinyl, optionally substituted pyridopyrazinyl, optionally substituted pyridopyridazinyl, optionally substituted thienothiazolyl, optionally substituted thienoxazolyl, optionally substituted pyridine, optionally substituted quinoline, optionally substituted pyrimidine, optionally substituted pyrazine, optionally substituted pyridazine, optionally substituted pyrine, and the like.

In certain embodiments, $Ar^1$, $Ar^3$, and $Ar^4$ are selected from the group consisting of optionally substituted phenyl, optionally substituted furyl, optionally substituted pyrrolyl, optionally substituted pyrazolyl, optionally substituted thienyl, optionally substituted indolyl, optionally substituted imidazyl, optionally substituted thiazolyl, optionally substituted isothiazolyl, optionally substituted oxazolyl, optionally substituted isooxazolyl, optionally substituted benzofuranyl, optionally substituted indolyl, optionally substituted isoindolyl, optionally substituted benzothiophenyl, optionally substituted 1,3-benzodioxolyl, optionally substituted benzopyrazolyl, optionally substituted benzoimidazyl, optionally substituted benzothiazolyl, optionally substituted benzoisothiazolyl, optionally substituted benzooxazolyl, optionally substituted benzoisooxazolyl, optionally substituted napthyl, substituted anthracenyl, optionally substituted phenoaxazinyl, and optionally substituted phenothiazinyl.

In certain embodiments, the tetraarylmethane of Formula I has Formula Ia:

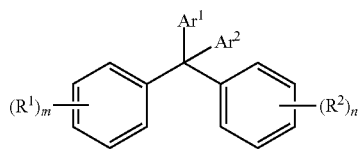

Ia wherein
each of m and n is independently selected from 1, 2, 3, or 4;
$Ar^1$ is aryl or heteroaryl;
$Ar^2$ is a heteroaryl;
$R^1$ and $R^2$ are each independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —$OR^3$, —$OSi(R^3)_3$, —$O(C=O)R^3$, —$(C=O)OR^3$, —$O(C=O)OR^3$, —$(C=O)R^3$, —$N(R^4)_2$, —$N(R^4)(C=O)R^3$, —$(C=O)N(R^4)_2$, —$N(R^4)(C=O)N(R^4)_2$, —$N(R^4)(C=O)OR^3$, —$O(C=O)N(R^4)_2$, —$SR^3$, —$(S=O)R^3$, —$SO_2R^3$, —$SO_2N(R^4)_2$, —$N(R^4)SO_2R^3$, —$SeR^3$, —$P(R^3)_3$, —$P(OR^3)_3$, and —$(P=O)(OR^3)_3$; or two instances of $R^1$ taken together with the carbons to which they are attached form a 5-6 membered cycloalkyl, heterocycloalkyl, aryl, or heteroaryl; or two instances of $R^2$ taken together with the carbons to which they are attached form a 5-6 membered cycloalkyl, heterocycloalkyl, aryl, or heteroaryl;
$R^3$ is selected from the group consisting of hydrogen, alkyl, haloalkyl, perhaloalkyl, alkene, alkyne, cycloalkyl, heterocycloalkyl, aryl, araalkyl, and heteroaryl; and
$R^4$ for each instance is independently selected from the group consisting of hydrogen, alkyl, haloalkyl, perhaloalkyl, alkene, alkyne, cycloalkyl, heterocycloalkyl, aryl, araalkyl, and heteroaryl; or two instances of $R^4$ taken together with the nitrogen to which they are attached form a 3-6 membered heterocycloalkyl; or one instance of $R^3$ and one instance of $R^4$ taken together with the atoms to which they are attached form a 4-6 membered heterocycloalkyl; and the method comprises:
contacting a compound of Formula IIa:

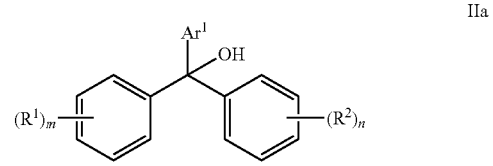

IIa with a heteroaromatic nucleophile in the presence of a chiral Brønsted acid under conditions that facilitate an electrophilic aromatic substitution reaction thereby forming the compound of Formula Ia.

Without wishing to be bound by theory, it is believed that the reaction of the compound of Formula II proceeds through a triaryl methane carbocation like intermediate, which reacts with the heteroaromatic nucleophile in an electrophilic aromatic substitution reaction. Thus, aryl and heteroaryl substituents that tend to stabilize the triaryl methane carbocation intermediate can improve the yield of the electrophilic aromatic substitution reaction. Likewise, more electron rich heteroaromatic nucleophiles can improve the yield of the electrophilic aromatic substitution reaction. In certain embodiments, one, two, or three moieties selected from the group of $Ar^1$, $Ar^2$, and $Ar^3$ in the compound of Formula II include at least one electron donating substituent. Exemplary electron donating substituents include, but are not limited to, —$OR^3$, —$OSi(R^3)_3$, —$O(C=O)R^3$, —$O(C=O)OR^3$, —$N(R^4)_2$, —$N(R^4)(C=O)R^3$, —$N(R^4)(C=N(R^4))R^3$, —$N(R^4)(C=O)N(R^4)_2$, —$N(R^4)(C=N(R^4))N(R^4)_2$, —$N(R^4)(C=O)OR^3$, —$O(C=O)N(R^4)_2$, —$SR^3$, —$N(R^4)SO_2R^3$, —$SeR^3$, —$P(R^3)_3$, —$P(OR^3)_3$, —$S(C=S)R^3$, —$S(C=S)SR^3$, —$N(R^4)(C=S)R^3$, —$N(R^4)(C=S)N(R^4)_2$, —$N(R^4)(C=S)SR^3$, and —$S(C=S)N(R^4)_2$, wherein $R^3$ is selected from the group consisting of hydrogen, alkyl, haloalkyl, perhaloalkyl, alkene, alkyne, cycloalkyl, heterocycloalkyl, aryl, araalkyl, and heteroaryl; and $R^4$ for each instance is independently selected from the group consisting of hydrogen, alkyl, haloalkyl, perhaloalkyl, alkene, alkyne, cycloalkyl, heterocycloalkyl, aryl, araalkyl, and heteroaryl; or two instances of $R^4$ taken together with the nitrogen to which they are attached form a 3-6 membered heterocycloalkyl; or one instance of $R^3$ and one instance of $R^4$ taken together with the atoms to which they are attached form a 4-6 membered heterocycloalkyl.

In certain embodiments, the electron donating substituent is covalently attached to at least one atom present in the aromatic rings of one or more of $Ar^1$, $Ar^2$, and $Ar^3$ of Formula II that is π-conjugated to the triaryl methane carbocation intermediate. For example, when Ar³ is an optionally substituted phenyl moiety, when the electron donating substituent is covalently attached at least at one site selected from the ortho position(s) and the para position of the phenyl moiety as depicted below:

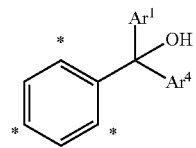

it is π-conjugated to the triaryl methane carbocation intermediate.

In such embodiments, the compound of Formula IIa can be represented by a structure selected from:

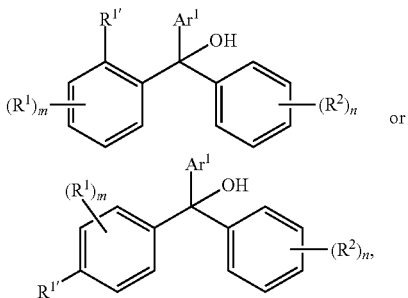

wherein m is 0, 1, 2, or 3;
n is 1, 2, 3, or 4;
p is 0, 1, 2, or 3;
q is 0, 1, or 2;
Ar¹ is selected from the group consisting of:

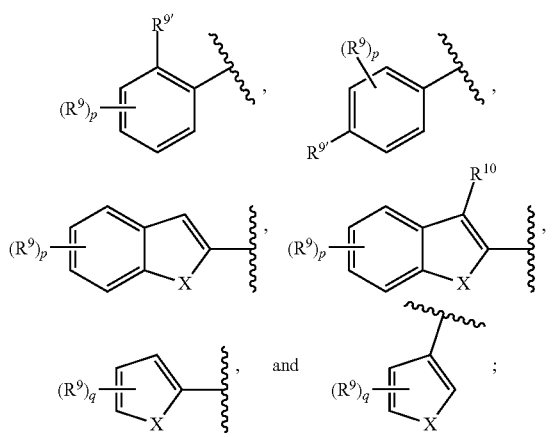

X is NR¹¹, O, S, or Se;
R¹ and R² are each independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —OR³, —OSi(R³)₃, —O(C=O)R³, —(C=O)R³, —O(C=O)OR³, —(C=O)R³, —N(R⁴)₂, —N(R⁴)(C=O)R³, —N(R⁴)(C=O)N(R⁴)₂, —N(R⁴)(C=O)OR³, —O(C=O)N(R⁴)₂, —SR³, —(S=O)R³, —SO₂R³, —SO₂N(R⁴)₂, —N(R⁴)SO₂R³, —SeR³, —P(R³)₃, —P(OR³)₃, and —(P=O)(OR³)₃; or two instances of R¹ taken together with the carbons to which they are attached form a 5-6 membered cycloalkyl, heterocycloalkyl, aryl, or heteroaryl; or two instances of R² taken together with the carbons to which they are attached form a 5-6 membered cycloalkyl, heterocycloalkyl, aryl, or heteroaryl;

R¹' is selected from the group consisting of —OR³, —OSi(R³)₃, —O(C=O)R³, —O(C=O)OR³, —N(R⁴)₂, —N(R⁴)(C=O)R³, —N(R⁴)(C=O)N(R⁴)₂, —N(R⁴)(C=O)OR³, —O(C=O)N(R⁴)₂, —SR³, —N(R⁴)SO₂R³, —SeR³, —P(R³)₃, and —P(OR³)₃; or R¹' and one instance of R¹ taken together with the carbons to which they are attached form a 5-6 membered cycloalkyl, heterocycloalkyl, aryl, or heteroaryl;

each R⁹ is independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —OR³, —OSi(R³)₃, —O(C=O)R³, —(C=O)OR³, —O(C=O)OR³, —(C=O)R³, —N(R⁴)₂, —N(R⁴)(C=O)R³, —(C=O)N(R⁴)₂, —N(R⁴)(C=O)N(R⁴)₂, —N(R⁴)(C=O)OR³, —O(C=O)N(R⁴)₂, —SR³, —(S=O)R³, —SO₂R³, —SO₂N(R⁴)₂, —N(R⁴)SO₂R³, —SeR³, —P(R³)₃, —P(OR³)₃, and —(P=O)(OR³)₃;

R⁹' is selected from the group consisting of —OR³, —OSi(R³)₃, —O(C=O)R³, —O(C=O)OR³, —N(R⁴)₂, —N(R⁴)(C=O)R³, —N(R⁴)(C=O)N(R⁴)₂, —N(R⁴)(C=O)OR³, —O(C=O)N(R⁴)₂, —SR³, —N(R⁴)SO₂R³, —SeR³, —P(R³)₃, and —P(OR³)₃; or two instances of R⁹' taken together with the carbons to which they are attached form a 5-6 membered cycloalkyl, heterocycloalkyl, aryl, or heteroaryl; and R¹⁰ is selected from the group consisting of alkyl, haloalkyl, perhaloalkyl, alkene, alkyne, cycloalkyl, heterocycloalkyl, aryl, araalkyl, heteroaryl, halide, —OR³, —OSi(R³)₃, —O(C=O)R³, —O(C=O)OR³, —N(R⁴)₂, —N(R⁴)(C=O)R³, —N(R⁴)(C=O)N(R⁴)₂, —N(R⁴)(C=O)OR³, —O(C=O)N(R⁴)₂, —SR³, —N(R⁴)SO₂R³, or —SeR³; and R¹¹ is hydrogen, alkyl, haloalkyl, perhaloalkyl, alkene, alkyne, cycloalkyl, heterocycloalkyl, aryl, araalkyl, heteroaryl, —(C=O)OR³, —(C=O)R³, —(C=O)N(R⁴)₂, —SO₂R³, or —SO₂N(R⁴)₂.

The heteroaromatic nucleophile can be a compound represented by the Formula IV:

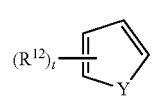

IV wherein t is 0, 1, 2, or 3;
Y is NR¹³, O, S, or Se;
each R¹² is independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —OR³, —OSi(R³)₃, —O(C=O)R³, —(C=O)OR³, —O(C=O)OR³, —(C=O)R³, —N(R⁴)₂, —N(R⁴)(C=O)R³, —(C=O)N(R⁴)₂, —N(R⁴)(C=O)N(R⁴)₂, —N(R⁴)(C=O)OR³, —O(C=O)N(R⁴)₂, —SR³, —(S=O)R³, —SO₂R³, —SO₂N(R⁴)₂, —N(R⁴)SO₂R³, —SeR³, —P(R³)₃, —P(OR³)₃, and —(P=O)(OR³)₃;

or two instances of $R^{12}$ taken together with the carbons to which they are attached form a 5-6 membered cycloalkyl, cycloalkylene, heterocycloalkyl, aryl, or heteroaryl; and $R^{13}$ is hydrogen, alkyl, haloalkyl, perhaloalkyl, alkene, alkyne, cycloalkyl, heterocycloalkyl, aryl, araalkyl, heteroaryl, —(C=O)OR$^3$, —(C=O)R$^3$, —(C=O)N(R$^4$)$_2$, —SO$_2$R$^3$, or —SO$_2$N(R$^4$)$_2$.

In certain embodiments, t is 1 or 2; Y is NH; $R^{12}$ is hydrogen, alkyl, haloalkyl, perhaloalkyl, alkene, alkyne, cycloalkyl, heterocycloalkyl, aryl, araalkyl, heteroaryl; or two instances of $R^{12}$ taken together with the carbons to which they are attached form a 5-6 membered cycloalkyl or cycloalkylene.

In certain embodiments, the heteroaromatic nucleophile is selected from the group consisting of optionally substituted pyrrole, optionally substituted 2-alkylpyrrole, optionally substituted 3-alkylpyrrole, optionally substituted 2-arylpyrrole, optionally substituted 3-arylpyrrole, optionally substituted tetrahydro-1H-indole, optionally substituted 4,7-dihydro-1H-indole, optionally substituted furan, optionally substituted thiophene, optionally substituted selenophene, optionally substituted benzothiophene, optionally substituted benzene, optionally substituted phenol, optionally substituted naphthol and optionally substituted thiophenol.

Typically, one or more equivalents of the heteroaromatic nucleophile can be used relative to the compound of Formula II. However, in instances in which the heteroaromatic nucleophile is costly or only available in small amounts, the compound of Formula II can be used in excess. In certain embodiments, the 1 to 10, 1 to 7, 1 to 5, 1 to 4, 1 to 3, 1 to 2 or 1 to 1.5, or 1 to 1.1 equivalents relative to the compound of Formula II is used.

Figure 2:
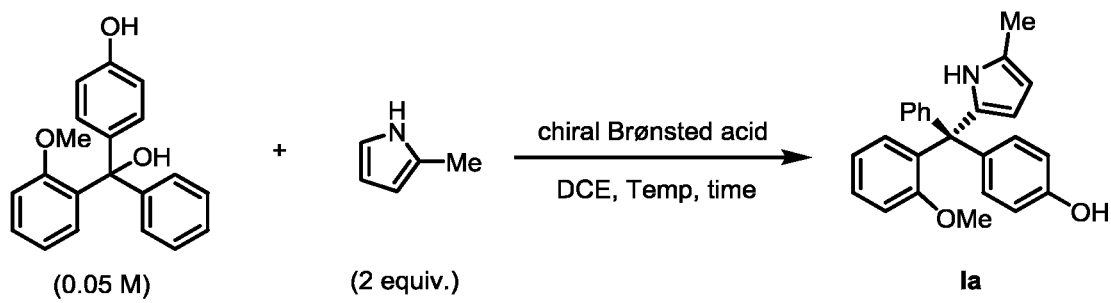
FIG. 2 depicts experimental results obtained from screening chiral Brønsted acids in a model electrophilic aromatic substitution reaction with 4-(hydroxy(2-methoxyphenyl)(phenyl)methyl)phenol in accordance with certain embodiments of the methods described herein.
Figure 2:
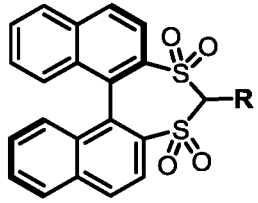
Figure 2:
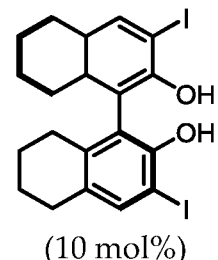
Figure 2:
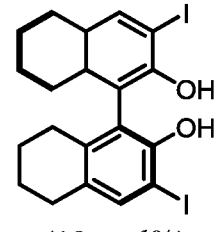

The chiral Brønsted acid used in the methods described herein can be any chiral Brønsted acid. The selection of the chiral Brønsted acid is well within the skill of a person skilled in the art and generally depends on the structure of the desired product and target yield and ee. The experimental results depicted in FIG. 2 show the results of screening different chiral Brønsted acids in the methods described herein. The observed ee and yield of screened chiral Brønsted acids can be optimized by screening structurally related chiral Brønsted acids to further improve yield and/or ee. For example, the yield and ee of entry 3 was improved when the structurally related analog entry 4 was tested.

In certain embodiments, the chiral Brønsted acid is a chiral phosphoric acid. The chiral phosphoric acid can be a C$_2$ symmetrical chiral phosphoric acid. In certain embodiments, the chiral phosphoric acid is represented by the Formula IIIa, Formula IIIb, Formula IIIc or Formula IIId:

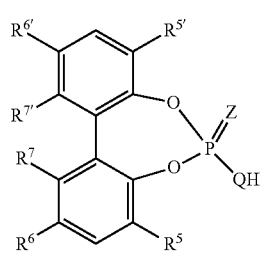

IIIa

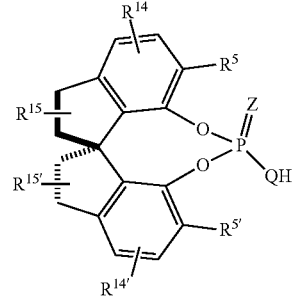

IIIb

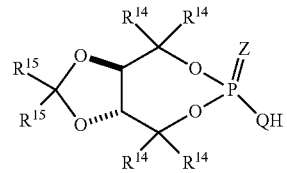

IIIc

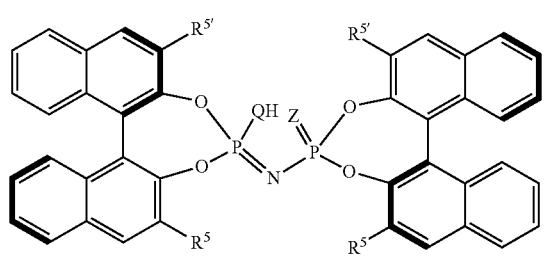

IIId wherein Q is O, S, or NSO$_2$R$^{16}$;

Z is O, S, or Se;

each of $R^5$ and $R^{5'}$ is independently hydrogen, alkyl, haloalkyl, perhaloalkyl, cycloalkyl, heterocycloalkyl, aryl, araalkyl, heteroaryl, halide, or triarylsilane;

each of $R^6$ and $R^{6'}$ is independently hydrogen, alkyl, haloalkyl, perhaloalkyl, cycloalkyl, heterocycloalkyl, aryl, araalkyl, heteroaryl, halide, or trialkylsilane;

each of $R^7$ and $R^{7'}$ is independently alkyl, haloalkyl, perhaloalkyl, cycloalkyl, heterocycloalkyl, aryl, araalkyl, heteroaryl, halide, or trialkylsilane; or $R^{6'}$ and $R^{7'}$ taken together with the carbons to which they are attached form 5-6 membered cycloalkyl or 6 membered aryl and $R^6$ and $R^7$ taken together with the carbons to which they are attached form 5-6 membered cycloalkyl or 6 membered aryl;

each of $R^{14}$ and $R^{14'}$ is independently hydrogen, alkyl, haloalkyl, perhaloalkyl, cycloalkyl, heterocycloalkyl, aryl, araalkyl, heteroaryl, halide, or trialkylsilane;

each of $R^{15}$ and $R^{15'}$ is independently hydrogen, alkyl, haloalkyl, perhaloalkyl, cycloalkyl, heterocycloalkyl, aryl, araalkyl, heteroaryl, halide, or trialkylsilane; and $R^{16}$ is alkyl or aryl.

In certain embodiments, the chiral phosphoric acid is represented by the Formula IIIa or Formula IIIb:

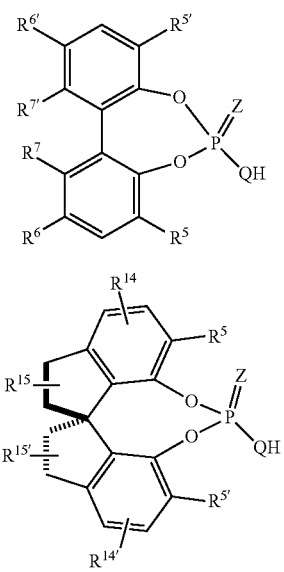

wherein Q is O;
Z is O;
each of $R^5$ and $R^{5'}$ is independently hydrogen, alkyl, haloalkyl, perhaloalkyl, cycloalkyl, heterocycloalkyl, aryl, araalkyl, heteroaryl, halide, or triarylsilane;
each of $R^6$ and $R^{6'}$ is independently hydrogen, alkyl, haloalkyl, perhaloalkyl, cycloalkyl, heterocycloalkyl, aryl, araalkyl, heteroaryl, halide, or trialkylsilane; and
each of $R^7$ and $R^{7'}$ is independently alkyl, haloalkyl, perhaloalkyl, cycloalkyl, heterocycloalkyl, aryl, araalkyl, heteroaryl, halide, or trialkylsilane; or $R^{6'}$ and $R^{7'}$ taken together with the carbons to which they are attached form 5-6 membered cycloalkyl or 6 membered aryl and $R^6$ and $R^7$ taken together with the carbons to which they are attached form 5-6 membered cycloalkyl or 6 membered aryl.

In certain embodiments, the chiral phosphoric acid has the structure:

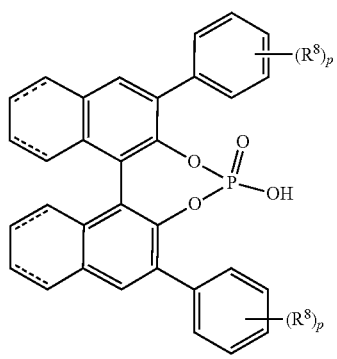

wherein
p is 1, 2, 3, or 4; and
$R^8$ is hydrogen, alkyl, haloalkyl, perhaloalkyl, cycloalkyl, heterocycloalkyl, aryl, halide, and triarylsilane.

In certain embodiments, the chiral phosphoric acid has the structure:

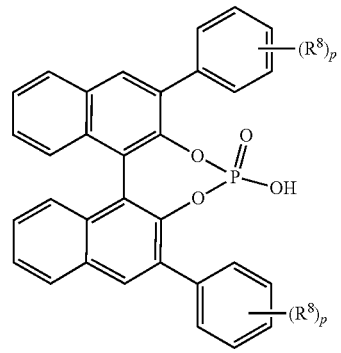

wherein
p is 1, 2, 3, or 4; and
$R^8$ is alkyl, cycloalkyl, or aryl.

The chiral Brønsted acid is typically optically enriched. In certain embodiments, the chiral Brønsted acid has an ee of 50% or greater, 60% or greater, 70% or greater, 80% or greater, 90% or greater, 95% or greater, 97% or greater, 98% or greater, 99% or greater. In certain embodiments, the chiral Brønsted acid has an ee of between 90% and 99.9%, 95% and 99.9%, or 98% and 99.9%.

Figure 3:
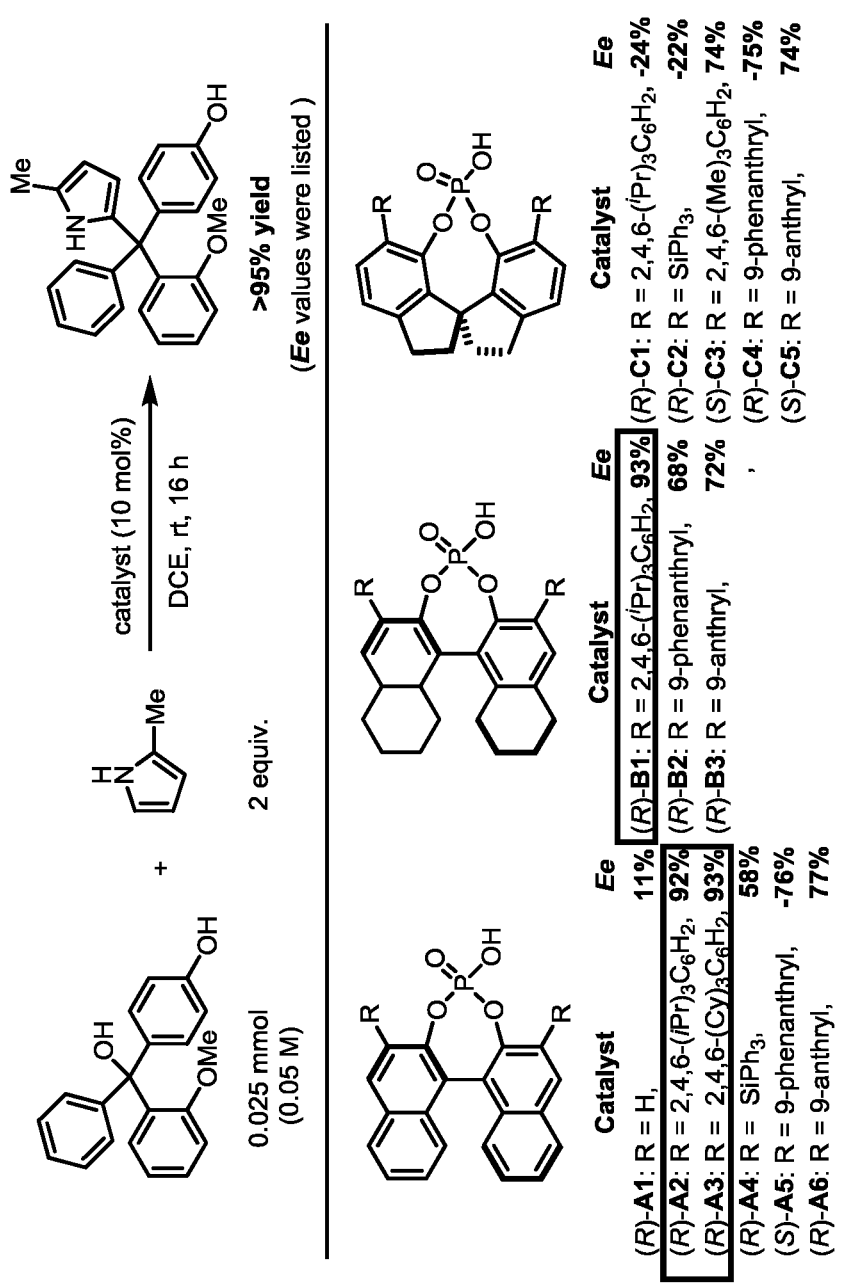
FIG. 3 depicts experimental results obtained from screening chiral phosphoric acids in a model electrophilic aromatic substitution reaction with 4-(hydroxy(2-methoxyphenyl)(phenyl)methyl)phenol in accordance with certain embodiments of the methods described herein.
Figure 7:
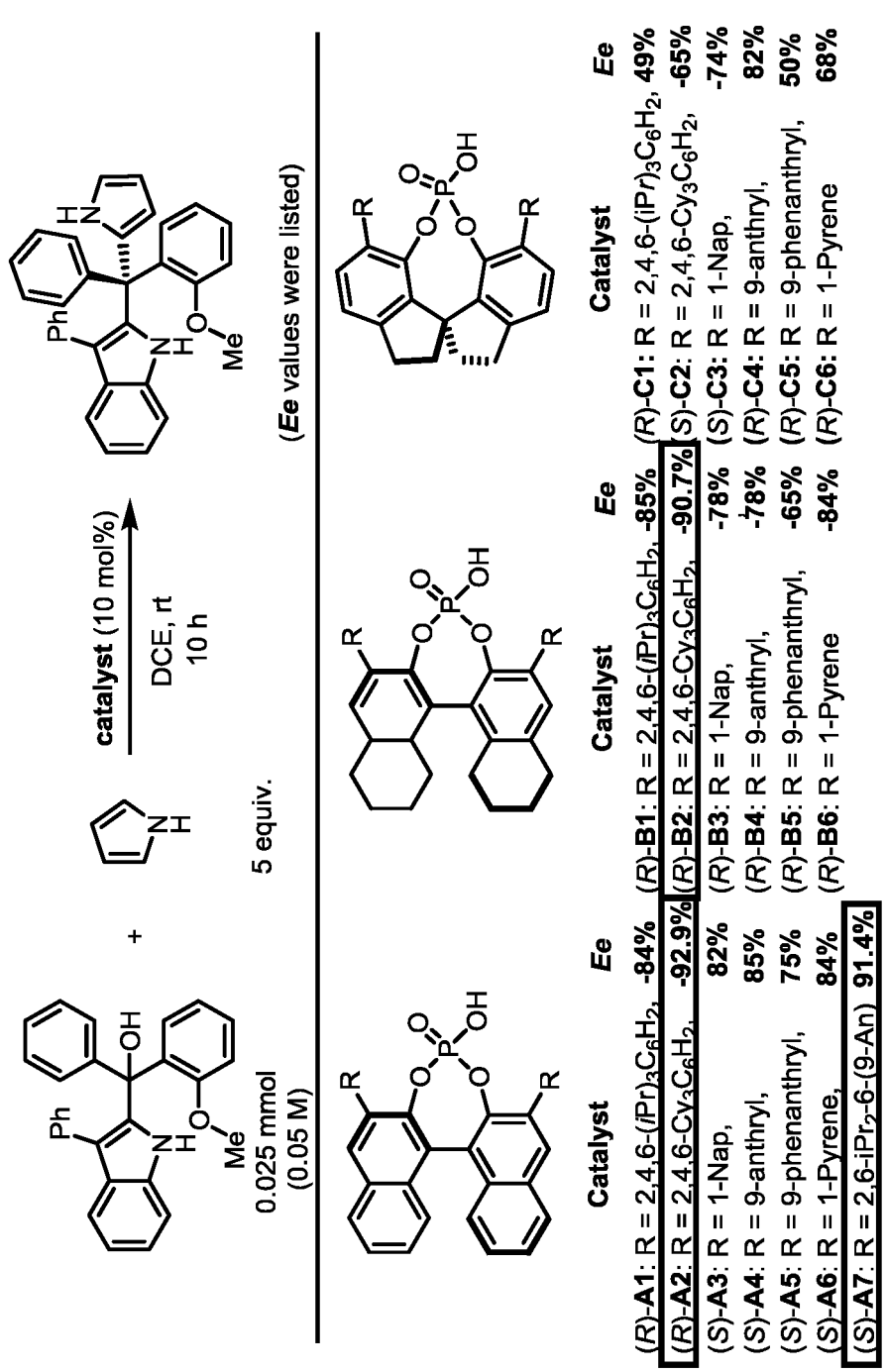
FIG. 7 depicts experimental results obtained from screening chiral Brønsted acids in a model electrophilic aromatic substitution reaction with (2-methoxyphenyl)(phenyl)(3-phenyl-1H-indol-2-yl)methanol in accordance with certain embodiments of the methods described herein.

The yield and ee of various chiral phosphoric acids of Formula IIIa or Formula IIIb are shown in FIG. 3 and FIG. 7. In all cases, the ee of the compound of Formula 1 is good to excellent.

The chiral Brønsted acid can be present in the reaction at between 0.5 to 20 mol % relative to the compound of Formula II. In certain embodiments, the chiral Brønsted acid is present in the reaction at between 0.5 to 15 mol %, 1 to 15 mol %, 2.5 to 15 mol %, 5 to 15 mol %, or 5 to 10 mol % relative to the compound of Formula II.

Figure 4:
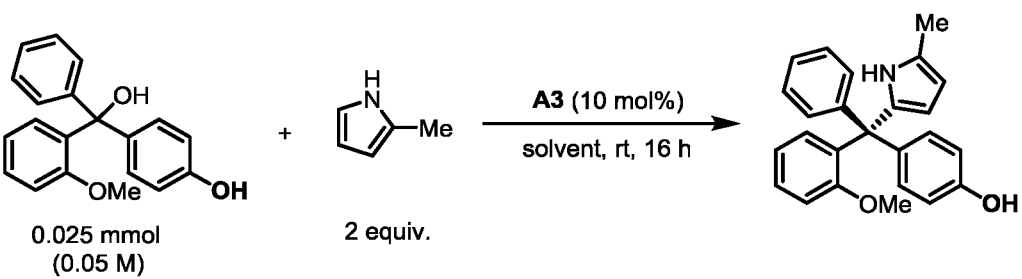
FIG. 4 depicts experimental results obtained from screening solvents acids in a model electrophilic aromatic substitution reaction with 4-(hydroxy(2-methoxyphenyl)(phenyl)methyl)phenol in accordance with certain embodiments of the methods described herein.
Figure 5:
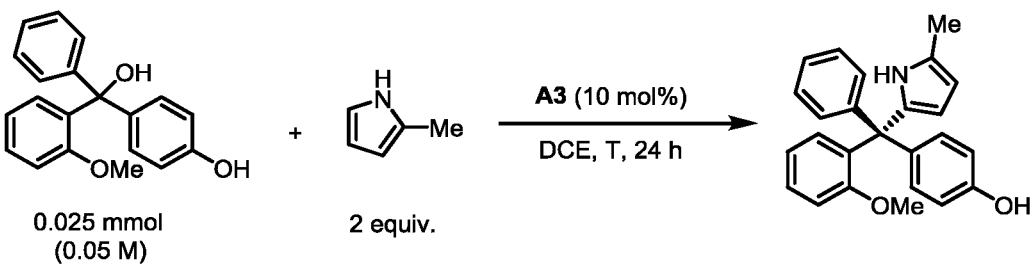
FIG. 5 depicts experimental results obtained from screening temperature in a model electrophilic aromatic substitution reaction with 4-(hydroxy(2-methoxyphenyl)(phenyl)methyl)phenol in accordance with certain embodiments of the methods described herein.
Figure 6:
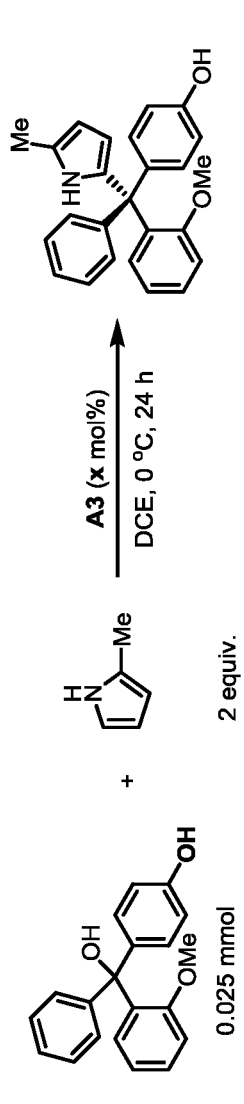
FIG. 6 depicts experimental results obtained from screening chiral Brønsted acid catalyst loading in a model electrophilic aromatic substitution reaction with 4-(hydroxy(2-methoxyphenyl)(phenyl)methyl)phenol in accordance with certain embodiments of the methods described herein.
Figure 8:
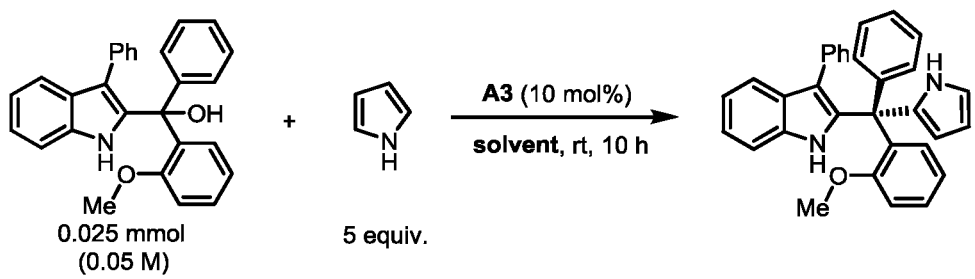
FIG. 8 depicts experimental results obtained from screening solvents in a model electrophilic aromatic substitution reaction with (2-methoxyphenyl)(phenyl)(3-phenyl-1H-indol-2-yl)methanol in accordance with certain embodiments of the methods described herein.
Figure 9:
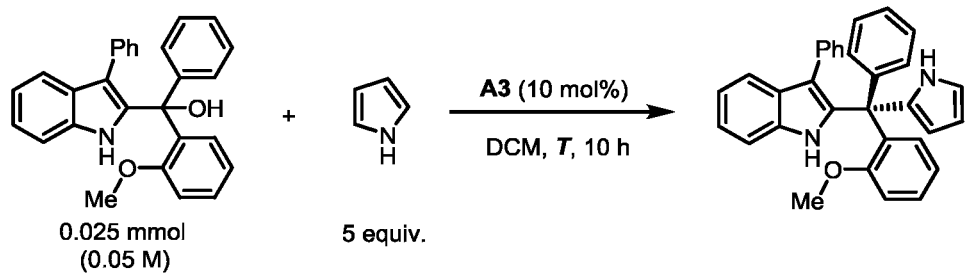
FIG. 9 depicts experimental results obtained from screening temperature in a model electrophilic aromatic substitution reaction with (2-methoxyphenyl)(phenyl)(3-phenyl-1H-indol-2-yl)methanol in accordance with certain embodiments of the methods described herein.
Figure 10:
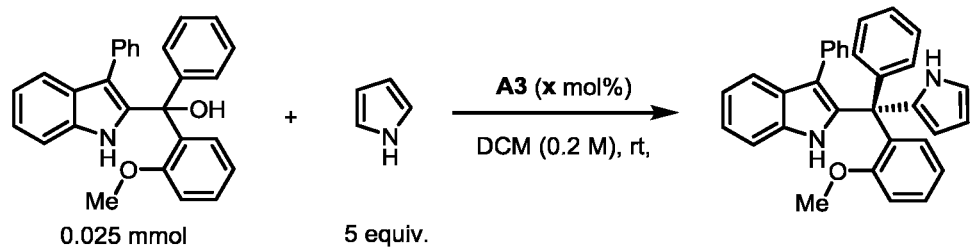
FIG. 10 depicts experimental results obtained from screening catalyst loading in a model electrophilic aromatic substitution reaction with (2-methoxyphenyl)(phenyl)(3-phenyl-1H-indol-2-yl)methanol in accordance with certain embodiments of the methods described herein.

Non-polar and polar aprotic solvents can be used in the methods described herein. In certain embodiments, the solvent is selected from aromatic solvents, haloaromatic solvents, ethers, ketones, haloalkanes, perhaloalkanes, and combinations thereof. Exemplary solvent include, but are not limited to benzene, toluene, chlorobenzene, trifluoromethylbenzene, diethyl ether, dimethoxyethane, tetrahydrofun, tetrahydropyran, dioxane, tert-butyl methylether, dichloromethane, chloroform, 1,2-dichloroethane, carbontetrachloride, and combinations thereof. FIG. 4 and FIG. 8 show that high yields and ee can be obtained in haloalkane solvents, such as dichloromethane and 1,2-dichloroethane.

Depending on the structure of the compound of Formula II, the heteraromatic nucleophile, and the desired ee/yield, the optimal temperature for conducting the method described herein can be any reaction temperature above −60° C. In certain embodiments, the reaction temperature is between −40° C. and 60° C., −40° C. and 50° C., −30° C. and 50° C., −30° C. and 40° C., −20° C. and 40° C., −20° C. and 30° C., −20° C. and 25° C., −10° C. and 25° C., −10° C. and 22° C., or 0° C. and 22° C. In certain embodiments, the reaction temperature is 22° C. or below.

Figure 11:
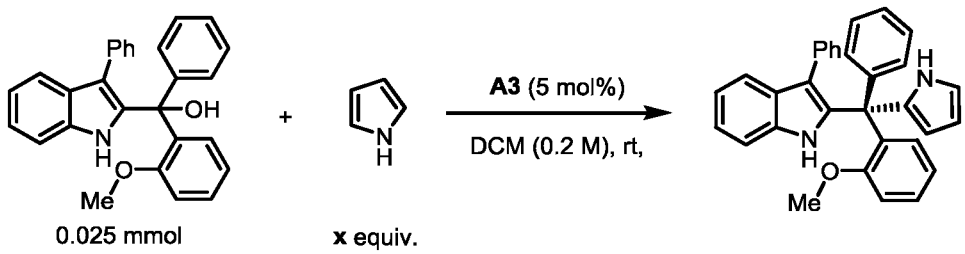
FIG. 11 depicts experimental results obtained from screening temperature in a model electrophilic aromatic substitution reaction with (2-methoxyphenyl)(phenyl)(3-phenyl-1H-indol-2-yl)methanol in accordance with certain embodiments of the methods described herein.
Figure 12:
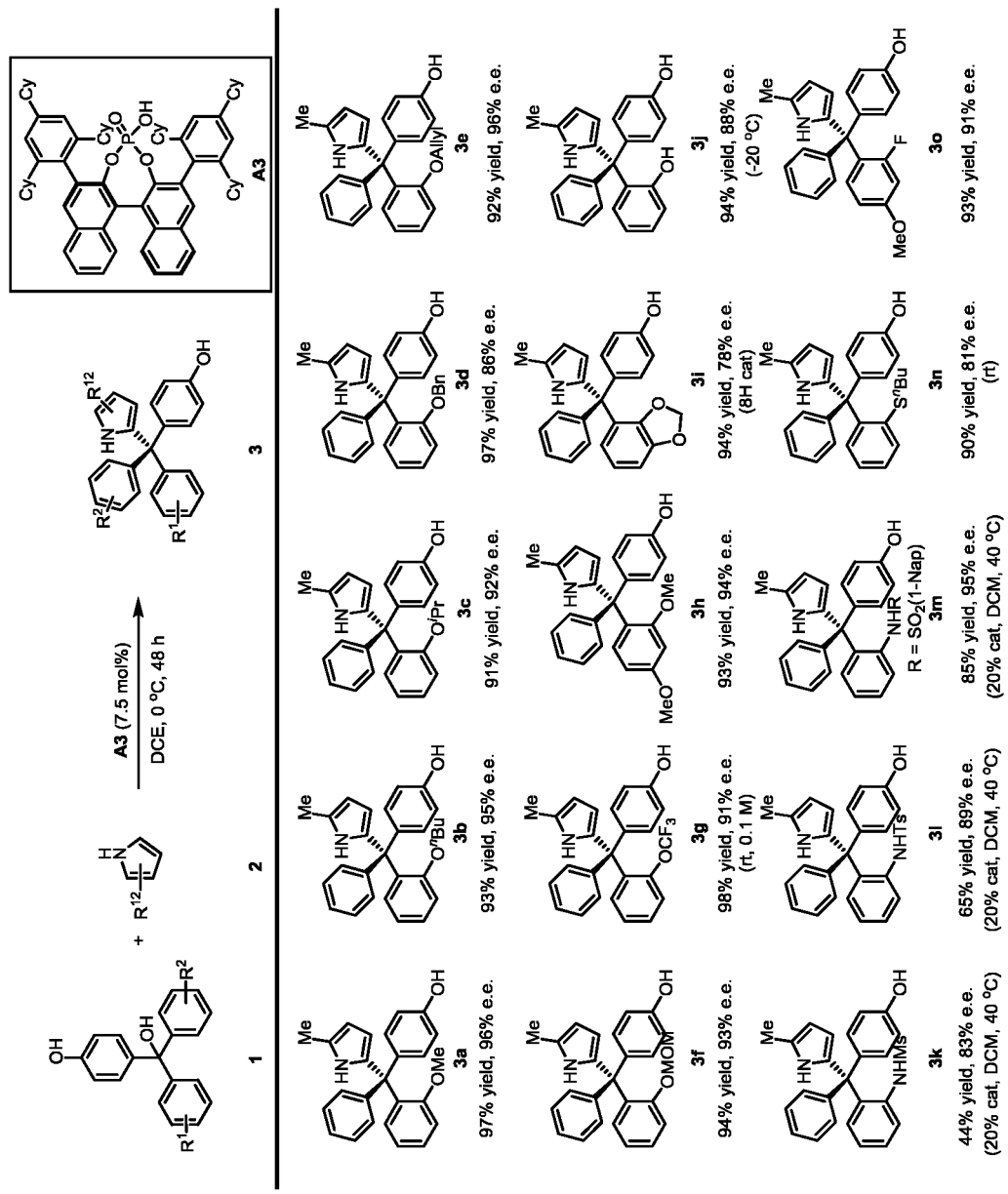
FIG. 12 depicts experimental results obtained from screening 4-(hydroxy(Ar$^3$)(Ar$^4$)methyl)phenol substrates in electrophilic aromatic substitution reactions with heteroaromatic nucleophiles with in accordance with certain embodiments of the methods described herein.
Figure 12:
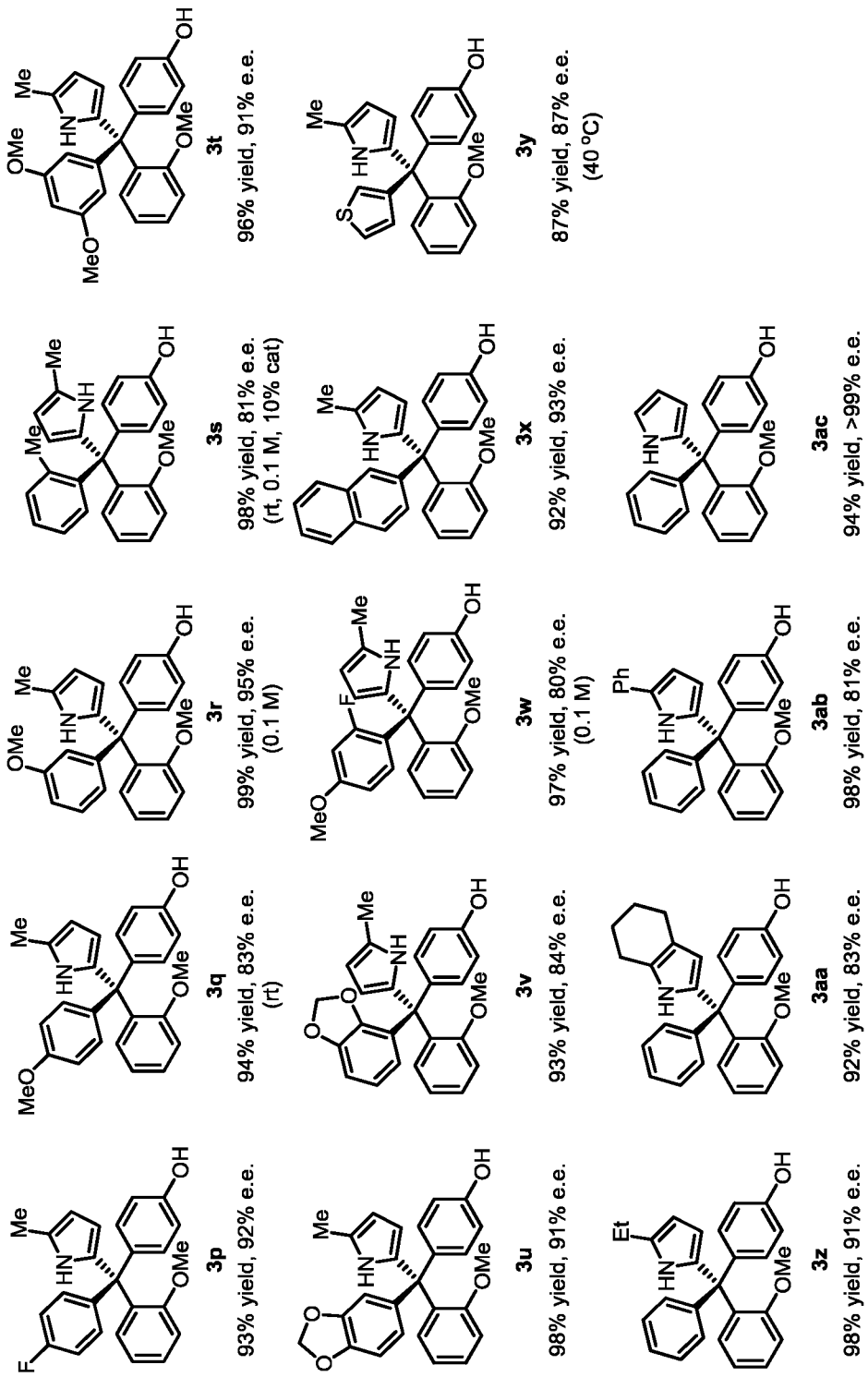
Figure 13:
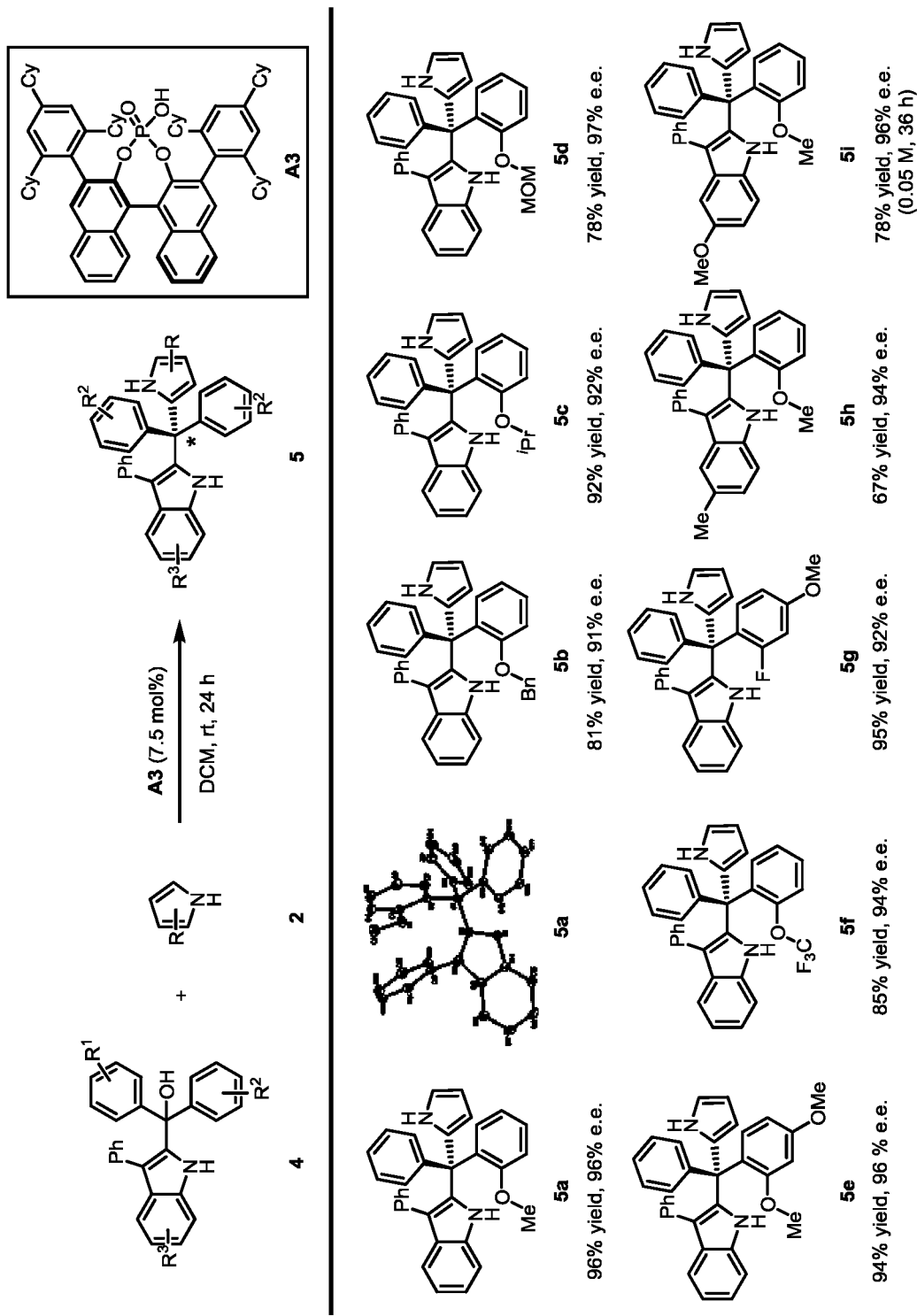
FIG. 13 depicts experimental results obtained from screening (Ar$^3$)(Ar$^4$)(3-phenyl-1H-indol-2-yl)methanol substrates in electrophilic aromatic substitution reactions with heteroaromatic nucleophiles with in accordance with certain embodiments of the methods described herein.
Figure 13:
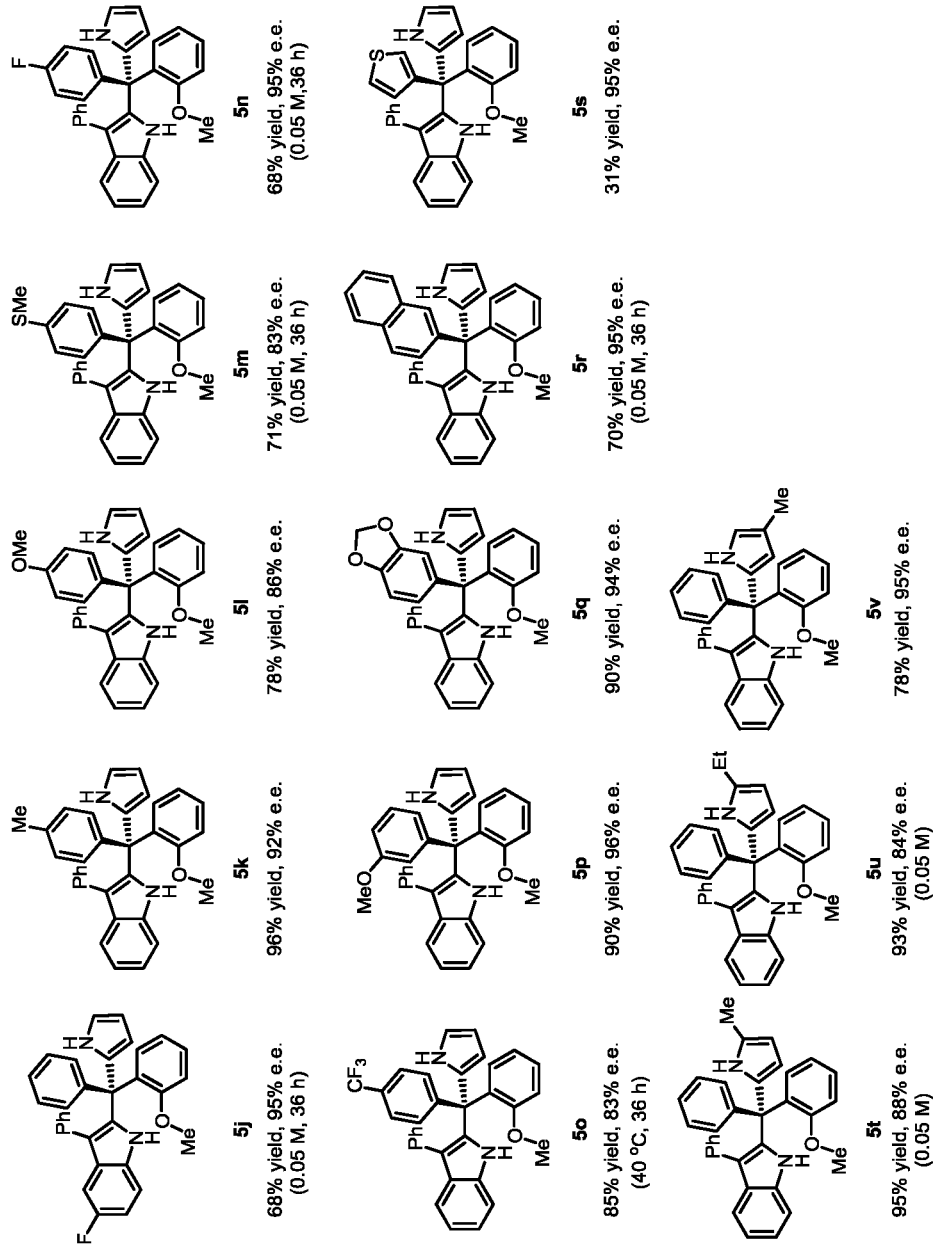

The experimental results in FIGS. 11 and 12 demonstrate the broad range of structurally and electronically diverse substituents that are tolerated on the compound of Formula II and afford the compound of Formula I in excellent yield and ee. Depending on the enantiomer of the chiral Brønsted acid utilized to catalyse the electrophilic aromatic substitution reaction either the (R) or the (S) enantiomer of the compound of Formula I can be selectively obtained. The compound of Formula I can be prepared with an enantiomeric excess (ee) of between 10% to 99.9%. In certain embodiments, the ee of the compound of Formula I is 20% to 99.9%, 30% to 99.9%, 40% to 99.9%, 40% to 99.5%, 40% to 98%, 50% to 98%, 60% to 98%, 70% to 98%, 75% to 98%, 80% to 98%, 80% to 96%, 85% to 98%, 90% to 98%, or 90% to 97%. In certain embodiments, the ee of the compound of Formula I is greater than 40%, greater than 50%, greater than 60%, greater than 70%, greater than 80%, greater than 90%, greater than 95%, or greater than 97%.

The methods described herein are able to prepare the compound of Formula I in yields of 30% to 98% or even higher. As demonstrated by the screening data presented in FIGS. 2-11, the methods described herein can be further optimized to increase yields and ee for specific compounds of Formula I using conventional methods well known in the art.

The ee of the compound of Formula I prepared according to the methods described herein can optionally be increased using any method known in the art, such as by recrystallization, chiral chromatography, or formation of diastereomers and separation using conventional analytical techniques (e.g., column chromatography, crystallization, etc).

The methods described herein can also be conducted with racemic or achiral Brønsted acids. In such instances, the compound of Formula I would be prepared in racemic form.

The method described herein provides an efficient means for preparing a wide array of chiral tetraarylmethanes of Formula I. These compounds can optionally be transformed to other useful compounds by using straightforward synthetic reactions, such as alkylation, oxidation and bromination. The enantiomeric excess of the compound of Formula I can generally remain intact without erosion from subsequent synthetic steps.

EXAMPLES

Flash column chromatography was performed over silica gel (200-300 mesh) purchased from Qindao Puke Co., China. All air or moisture sensitive reactions were conducted oven-dried glassware under a nitrogen atmosphere using anhydrous solvents. Anhydrous solvents were purified by the Innovative® solvent purification system. Chemicals were purchased from commercial suppliers and used without further purification unless otherwise stated. $^1$H, $^{13}$C, $^{19}$F, and $^{31}$P NMR spectra were collected on a Bruker AV 400 MHz NMR spectrometer using residue solvent peaks as an internal standard ($^3$H NMR: acetone-d$_6$, at 2.05 ppm; $^{13}$C NMR: acetone-d$_6$, at 29.84 ppm). Data for $^3$H NMR are recorded as follows: chemical shift (5, ppm), multiplicity (s=singlet; d=doublet; t=triplet; q=quarter; p=pentet; sept=septet; m=multiplet; br=broad), coupling constant (Hz), integration. Mass spectra were collected on an Agilent GC/MS 5975C system, a MALDI Micro MX mass spectrometer, or an API QSTAR XL System. IR spectra were recorded on Bruker TENSOR 27 spectrometer and reported in terms of frequency of absorption (cm$^{-1}$). Optical rotations were measured on JASCO P-2000 polarimeter with $[\alpha]^D$ values reported in degrees; concentration (c) is in 10 mg/mL. The enantiomeric excess values were determined by chiral HPLC using an Agilent 1200 LC instrument with Daicel CHIRALPAK® AD-H, IC—H, AS-H, or CHIRALCEL® OD-H columns.

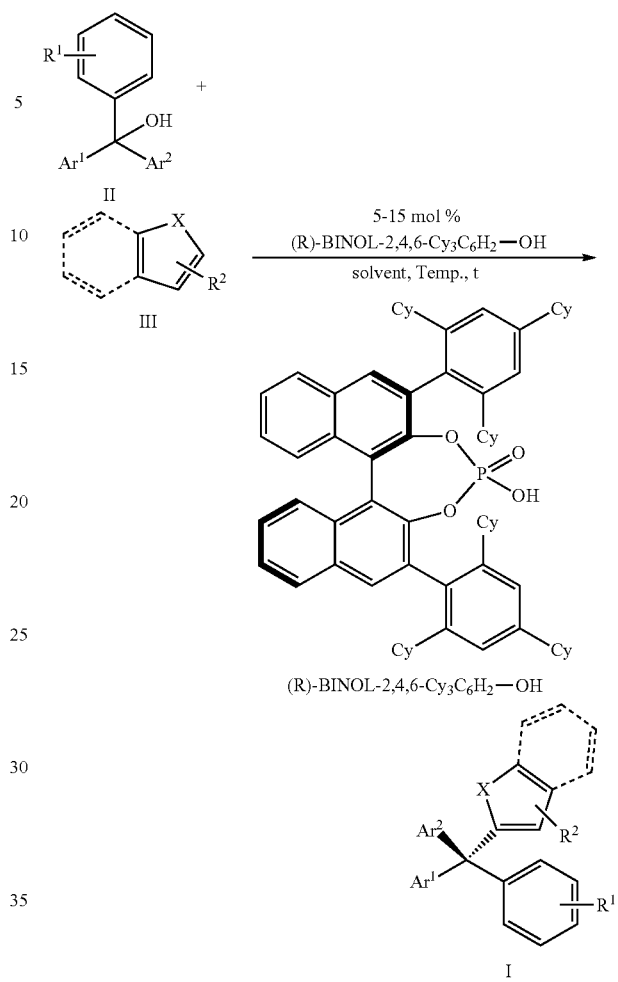

General Procedure: To a mixture of triarylmethanol II (0.2 mmol) and heterocyclic arenes (III) (0.2-0.4 mmol) in DCE (3.6 mL), the catalyst (R)-BINOL-2,4,6-Cy$_3$C$_6$H$_2$—OH (5-15 mol %) in DCE (0.4 mL) was added and then stirred for 48 h at a particular temperature. The progress was monitored by thin layer chromatography. Upon completion (time is specified in each case), the mixture was directly subjected to silica gel flash chromatography to give the pure product.

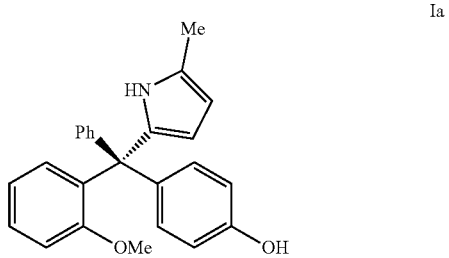

(R)-4-((2-Methoxyphenyl)(5-methyl-1H-pyrrol-2-yl)(phenyl)methyl) phenol (Ia) was prepared as colorless oil from 4-(hydroxy(2-methoxyphenyl)(phenyl)methyl)phenol (61.2 mg, 0.2 mmol) and 2-methylpyrrole (32.4 mg, 0.4 mmol) according to the General Procedure (eluent: hexanes/EtOAc=15:1 to 10:1) in 97% yield (71.7 mg, 96% ee).

[α]$_D^{26}$: +6.9 (c=1.0, CHCl$_3$). HPLC analysis of the product: Daicel CHIRALPAK IC column; 3% i-PrOH in hexanes; 1.0 mL/min; retention times: 9.7 min (major), 11.1 min (minor).

$^1$H NMR (400 MHz, acetone-d$_6$) δ 8.78 (s, 1H), 8.22 (s, 1H), 7.29-7.25 (m, 1H), 7.22-7.12 (m, 5H), 7.00-6.85 (m, 5H), 6.71 (d, J=8.7 Hz, 2H), 5.70-5.63 (m, 1H), 5.58-5.60 (m, 1H), 3.17 (s, 3H), 2.13 (s, 3H).

$^{13}$C NMR (100 MHz, acetone-d$_6$) δ 158.8, 156.0, 146.9, 137.6, 136.6, 136.5, 132.1, 130.8, 130.5, 129.1, 127.8, 127.5, 126.2, 121.0, 114.4, 114.0, 110.4, 105.3, 59.1, 55.5, 13.1.

IR (thin film) 3446, 3384, 3056, 2983, 2839, 1588, 1247, 1039, 733, 700 cm$^{-1}$.

HRMS (CI+) Calcd for C$_{25}$H$_{23}$NO$_2$ (M$^+$): 369.1729, Found: 369.1725.

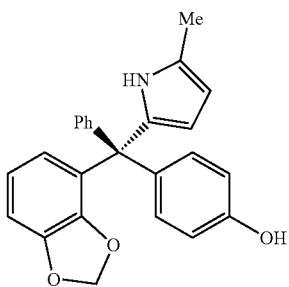

Ib (R)-4-(Benzo[d][1,3]dioxol-4-yl(5-methyl-1H-pyrrol-2-yl)(phenyl)methyl) phenol (Ib) was prepared as colorless oil from 4-(benzo[d][1,3]dioxol-4-yl(hydroxy)(phenyl)methyl)-phenol (64.0 mg, 0.2 mmol) and 2-methylpyrrole (32.4 mg, 0.4 mmol) according to the General Procedure (eluent: hexanes/EtOAc=15:1 to 10:1) in 94% yield (72.1 mg, 78% ee).

[α]$_D^{26}$: +4.5 (c=1.0, CHCl$_3$). HPLC analysis of the product: Daicel CHIRALPAK AD-H column; 3% i-PrOH in hexanes; 1.0 mL/min; retention times: 38.9 min (major), 40.8 min (minor).

$^1$H NMR (400 MHz, acetone-d$_6$) δ 9.08 (s, 1H), 8.30 (s, 1H), 7.26-7.13 (m, 5H), 6.94 (d, J=8.4 Hz, 2H), 6.81 (d, J=8.4 Hz, 1H), 6.77-6.71 (m, 3H), 6.55 (d, J=8.0 Hz, 1H), 5.72-5.59 (m, 4H), 2.16 (s, 3H).

$^{13}$C NMR (100 MHz, acetone-d$_6$) δ 156.5, 148.6, 146.3, 146.1, 136.3, 135.0, 131.9, 131.2, 130.7, 128.1, 128.0, 126.9, 123.5, 121.8, 114.8, 110.7, 108.3, 105.45, 100.8, 58.2, 13.1.

IR (thin film) 3440, 3416, 3052, 2975, 2885, 1589, 1440, 1259, 733 cm$^{-1}$.

HRMS (LD+) Calcd for C$_{25}$H$_{21}$NO$_3$ (M$^+$): 383.1521, Found: 383.1519.

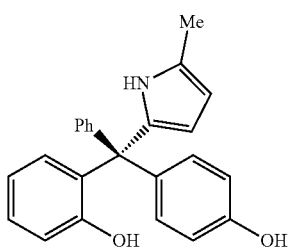

Ic (R)-2-((4-Hydroxyphenyl)(5-methyl-1H-pyrrol-2-yl)(phenyl)methyl) phenol (Ic) was prepared as colorless oil from 2-(hydroxy(4-hydroxyphenyl)(phenyl)methyl)phenol (58.4 mg, 0.2 mmol) and 2-methylpyrrole (32.4 mg, 0.4 mmol) according to the General Procedure (at −20° C.) (eluent: hexanes/EtOAc=15:1 to 10:1) in 94% yield (66.6 mg, 88% ee).

[α]$_D^{26}$: +4.3 (c=1.0, CHCl$_3$). HPLC analysis of the product: Daicel CHIRALPAK IC—H column; 5% i-PrOH in hexanes; 1.0 mL/min; retention times: 7.5 min (minor), 9.6 min (major).

$^1$H NMR (400 MHz, acetone-d$_6$) δ 9.39 (s, 1H), 8.34 (br, 1H), 7.27-7.12 (m, 6H), 6.94 (d, J=8.4 Hz, 2H), 6.86 (d, J=7.7 Hz, 1H), 6.79-6.73 (m, 4H), 6.39 (br, 1H), 5.87-5.80 (m, 1H), 5.77-5.71 (m, 1H), 2.17 (s, 3H).

$^{13}$C NMR (100 MHz, acetone-d$_6$) δ 156.7, 156.6, 146.4, 136.5, 134.3, 133.3, 132.2, 131.1, 130.9, 130.0, 129.4, 128.1, 127.0, 120.1, 117.8, 115.0, 110.7, 105.8, 58.4, 13.1.

IR (thin film) 3427, 3387, 3054, 2981, 2862, 1603, 1261, 1210, 1179, 737, 700 cm$^{-1}$.

HRMS (CI+) Calcd for C$_{24}$H$_{21}$NO$_2$ (M$^+$): 355.1572, Found: 355.1581.

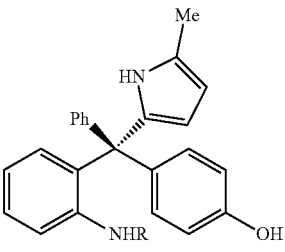

Id

R = SO$_2$(1-Nap)

(R)—N-(2-((4-Hydroxyphenyl)(5-methyl-1H-pyrrol-2-yl)(phenyl)methyl)-phenyl)naphtha ene-1-sulfonamide (Id) was prepared as colorless oil from N-(2-(hydroxy(4-hydroxyphenyl)(phenyl)methyl)phenyl)naphthalene-1-sulfonamide (96.2 mg, 0.2 mmol) and 2-methylpyrrole (32.4 mg, 0.4 mmol) according to the General Procedure (using 15 mol % of catalyst (29.8 mg, 0.03 mmol), DCM as solvent, at room temperature) (eluent: hexanes/EtOAc=15:1 to 10:1) in 85% yield (92.9 mg, 95% ee).

[α]$_D^{26}$: +4.5 (c=1.0, CHCl$_3$). HPLC analysis of the product: Daicel CHIRALPAK IC column; 30% i-PrOH in hexanes; 1.0 mL/min; retention times: 12.4 min (major), 15.1 min (minor).

$^1$H NMR (400 MHz, acetone-d$_6$) δ 9.42 (s, 1H), 8.50 (s, 1H), 8.24 (d, J=7.3 Hz, 1H), 8.19 (d, J=8.2 Hz, 1H), 8.07-7.98 (m, 2H), 7.67-7.61 (m, 3H), 7.46 (s, 1H), 7.30-7.24 (m, 3H), 7.15-7.09 (m, 4H), 6.93-6.88 (m, 4H), 6.74 (d, J=8.5 Hz, 2H), 6.19-6.11 (m, 1H), 6.00-5.94 (m, 1H), 2.13 (s, 3H).

$^{13}$C NMR (100 MHz, acetone-d$_6$) δ 156.9, 145.9, 138.9, 138.2, 136.2, 135.2, 135.1, 134.5, 133.3, 132.2, 131.7, 131.2, 130.9, 129.7, 129.3, 129.1, 128.7, 128.6, 128.4, 127.7, 127.4, 125.3, 125.2, 123.2, 118.9, 115.3, 111.0, 106.4, 59.0, 13.2.

IR (thin film) 3435, 3376, 3057, 2925, 2851, 1589, 1264, 743, 700 cm$^{-1}$.

HRMS (LD+) Calcd for C$_{34}$H$_{28}$N$_2$O$_3$S (M$^+$): 544.1821, Found: 544.1840.

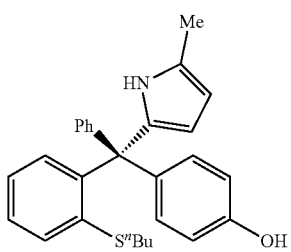

Ie (R)-4-((2-(Butylthio)phenyl)(5-methyl-1H-pyrrol-2-yl)(phenyl)methyl) phenol (Ie) was prepared as colorless oil from 4-((2-(butylthio)phenyl)(hydroxy)(phenyl)methyl) phenol (72.8 mg, 0.2 mmol) and 2-methylpyrrole (32.4 mg, 0.4 mmol) according to the General Procedure (at room temperature) (eluent: hexanes/EtOAc=15:1 to 10:1) in 90% yield (76.5 mg, 81% ee).

$[\alpha]_D^{26}$: +7.1 (c=1.0, CHCl$_3$). HPLC analysis of the product: Daicel CHIRALPAK IC column; 3% i-PrOH in hexanes; 1.0 mL/min; retention times: 8.3 min (major), 9.7 min (minor).

$^1$H NMR (400 MHz, acetone-d$_6$) δ 8.74 (s, 1H), 8.28 (s, 1H), 7.46 (d, J=7.5 Hz, 1H), 7.26-7.16 (m, 6H), 7.11 (t, J=7.8 Hz, 1H), 6.99-6.94 (m, 3H), 6.71 (d, j=8.6 Hz, 2H), 5.68-5.64 (m, 1H), 5.61-5.56 (m, 1H), 2.37 (t, J=6.9 Hz, 2H), 2.13 (s, 3H), 1.22-1.10 (m, 4H), 0.76 (t, J=6.9 Hz, 3H).

$^{13}$C NMR (100 MHz, acetone-d$_6$) δ 156.3, 148.5, 146.2, 140.7, 136.5, 136.2, 132.9, 132.6, 131.4, 131.2, 128.2, 128.0, 127.7, 126.5, 126.1, 114.6, 111.1, 105.6, 61.0, 35.6, 31.5, 22.7, 13.9, 13.1.

IR (thin film) 3444, 3386, 3052, 2957, 2927, 2865, 1587, 1262, 1175, 735, 700 cm$^{-1}$.

HRMS (LD+) Calcd for C$_{28}$H$_{29}$NOS (M$^+$): 427.1970, Found: 427.1982.

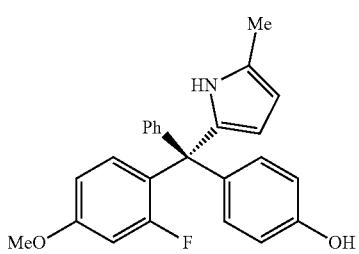

If (R)-4-((2-Fluoro-4-methoxyphenyl)(5-methyl-1H-pyrrol-2-yl)(phenyl) methy)phenol (If) was prepared as colorless oil from 4-((2-fluoro-4-methoxyphenyl)(hydroxy)(phenyl)methyl) phenol (64.8 mg, 0.2 mmol) and 2-methylpyrrole (32.4 mg, 0.4 mmol) according to the General Procedure (eluent: hexanes/EtOAc=15:1 to 10:1) in 93% yield (80.6 mg, 91% ee).

$[\alpha]_D^{26}$: +1.5 (c=1.0, CHCl$_3$). HPLC analysis of the product: Daicel CHIRALPAK OD-H column; 5% i-PrOH in hexanes; 1.0 mL/min; retention times: 19.1 min (major), 24.2 min (minor).

$^1$H NMR (400 MHz, acetone-d$_6$) δ 8.97 (s, 1H), 8.31 (s, 1H), 7.27-7.16 (m, 5H), 6.96-6.91 (m, 3H), 6.74 (d, J=8.8 Hz, 2H), 6.67 (dd, J$_1$=12.9, J$_2$=2.6 Hz, 1H), 6.61 (dd, J$_1$=12.9, J$_2$=2.7 Hz, 1H), 5.68-5.65 (m, 2H), 3.79 (s, 3H), 2.15 (m, 3H).

$^{13}$C NMR (100 MHz, acetone-d$_6$) δ 163.3 (d, J=247.6 Hz), 162.1 (d, J=11.0 Hz), 156.5, 146.5, 136.5, 135.3, 131.8 (d, J=5.7 Hz), 131.7, 130.3, 128.3, 128.0, 127.9 (d, J=11.3 Hz), 126.8, 114.9, 110.3, 109.4 (d, J=2.6 Hz), 105.5, 103.0 (d, J=26.5 Hz), 57.8, 55.8, 13.1.

$^{19}$F NMR (376 MHz, acetone-d$_6$) δ -97.8.

IR (thin film) 3446, 3054, 2932, 1616, 1261, 824, 733 cm$^{-1}$.

HRMS (CI+) Calcd for C$_{25}$H$_{22}$FNO$_2$ (M$^+$): 387.1635, Found: 387.1624.

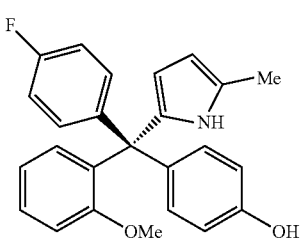

Ig (S)-4-((4-fluorophenyl)(2-methoxyphenyl)(5-methyl-1H-pyrrol-2-yl) methyl)phenol (Ig) was prepared as colorless oil from 4-((4-fluorophenyl)(hydroxy)(2-methoxyphenyl)methyl) phenol (62.8 mg, 0.2 mmol) and 2-methylpyrrole (32.4 mg, 0.4 mmol) according to the General Procedure (eluent: hexanes/EtOAc=15:1 to 10:1) in 93% yield (72.1 mg, 92% ee).

$[\alpha]_D^{26}$: +6.9 (c=1.0, CHCl$_3$). HPLC analysis of the product: Daicel CHIRALPAK IC—H column; 3% i-PrOH in hexanes; 1.0 mL/min; retention times: 8.7 min (major), 9.8 min (minor).

$^1$H NMR (400 MHz, acetone-d$_6$) δ 8.84 (s, 1H), 8.27 (s, 1H), 7.30-7.25 (m, 1H), 7.18-7.14 (m, 2H), 7.00-6.90 (m, 6H), 6.88 (td, J$_1$=7.6, J$_2$=1.0 Hz, 1H), 6.72 (d, J=8.8 Hz, 2H), 5.66 (t, J=2.4 Hz, 1H), 5.58 (t, J=3.0 Hz, 1H), 3.21 (s, 3H), 2.13 (s, 3H).

$^{13}$C NMR (100 MHz, acetone-d$_6$) δ 161.6 (d, J=240.1 Hz), 158.7, 156.1, 142.8 (d, J=3.3 Hz), 137.4, 136.4, 132.2 (d, J=6.7 Hz), 131.9, 130.7, 129.3, 128.0, 121.0, 114.5, 114.0 (d, 0.7=21.0 Hz), 113.8, 110.4, 105.4, 58.5, 55.4, 13.1.

$^{19}$F NMR (376 MHz, acetone-d$_6$) δ -118.1.

IR (thin film) 3447, 3053, 2980, 2936, 1593, 1476, 1261, 1020, 733 cm$^{-1}$.

HRMS (CI+) Calcd for C$_{25}$H$_{22}$NFO$_2$ (M$^+$): 387.1635, Found: 387.1638.

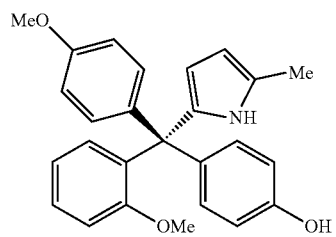

Ih (S)-4-((2-Methoxyphenyl)(4-methoxyphenyl)(5-methyl-1H-pyrrol-2-yl) methyl)phenol (Ih) was prepared as colorless oil from 4-(hydroxy(2-methoxyphenyl)(4-methoxyphenyl)methyl)phenol (67.2 mg, 0.2 mmol) and 2-methylpyrrole (32.4 mg, 0.4 mmol) according to the General Procedure (using 15 mol % of catalyst (at room temperature) (eluent: hexanes/EtOAc=15:1 to 10:1) in 94% yield (74.7 mg, 83% ee).

$[\alpha]_D^{26}$: +1.7 (c=1.0, CHCl$_3$). HPLC analysis of the product: Daicel CHIRALPAKIC-H column; 5% i-PrOH in hexanes; 1.0 mL/min; retention times: 8.7 min (major), 10.1 min (minor).

$^1$H NMR (400 MHz, acetone-d$_6$) δ 8.76 (s, 1H), 8.19 (s, 1H), 7.26 (t, J=1.9 Hz, 1H), 7.04 (d, J=8.4 Hz, 2H), 6.92-6.92 (m, 4H), 6.86 (t, J=7.4 Hz, 1H), 6.77 (d, J=8.7 Hz, 2H), 6.69 (d, J=8.2 Hz, 2H), 5.68-5.61 (m, 1H), 5.68-5.54 (m, 1H), 3.75 (s, 3H), 3.20 (s, 3H), 2.13 (s, 3H).

$^{13}$C NMR (100 MHz, acetone-d$_6$) δ 158.9, 158.4, 155.9, 138.7, 137.9, 137.3, 136.9, 131.8, 131.7, 130.7, 129.1, 127.6, 121.0, 114.4, 114.0, 112.8, 110.2, 105.3, 58.4, 55.6, 55.3, 13.1.

IR (thin film) 3445, 3389, 3050, 2838, 1590, 1249, 1176, 1031, 821, 735 cm$^{-1}$.

HRMS (LD+) Calcd for C$_{26}$H$_{25}$NO$_3$ (M$^+$): 399.1834, Found: 399.1827.

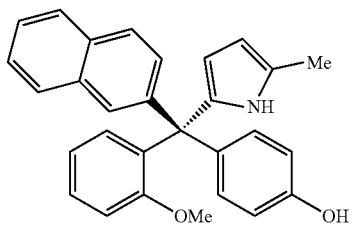

Ii (S)-4-((2-Methoxyphenyl)(5-methyl-1H-pyrrol-2-yl)(naphthalen-2-yl) methyl)phenol (Ii) was prepared as colorless oil from 4-(hydroxy(2-methoxyphenyl)(naphthalen-2-yl)methyl)phenol (71.2 mg, 0.2 mmol) and 2-methylpyrrole (32.4 mg, 0.4 mmol) according to the General Procedure (eluent: hexanes/EtOAc=15:1 to 10:1) in 92% yield (88.7 mg, 93% ee).

$[\alpha]_D^{26}$: +11.8 (c=1.0, CHCl$_3$). HPLC analysis of the product: Daicel CHIRALPAK IC—H column; 3% i-PrOH in hexanes; 1.0 mL/min; retention times: 11.7 min (major), 13.3 min (minor).

$^1$H NMR (400 MHz, acetone-d$_6$) δ 8.90 (s, 1H), 8.25 (s, 1H), 7.83 (d, J=7.3 Hz, 1H), 7.72-7.64 (m, 3H), 7.45-7.28 (m, 4H), 7.09-7.03 (m, 3H), 6.96-6.89 (m, 2H), 6.74 (d, J=8.6 Hz, 2H), 5.73-5.65 (m, 2H), 3.16 (s, 3H), 2.13 (s, 3H).

$^{13}$C NMR (100 MHz, acetone-d$_6$) δ 159.0, 156.1, 144.0, 137.4, 136.9, 136.3, 133.9, 132.8, 132.0, 130.9, 130.4, 129.3, 128.9, 128.4, 128.0, 128.0, 126.4, 126.31, 126.22, 121.1, 114.5, 114.0, 110.5, 105.5, 59.2, 55.5, 13.1.

IR (thin film) 3441, 3380, 3052, 2836, 1588, 1243, 734, 698 cm$^{-1}$.

HRMS (LD+) Calcd for C$_{29}$H$_{25}$NO$_2$ (M$^+$): 419.1885, Found: 419.1883.

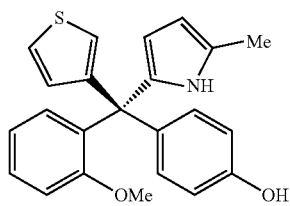

Ij (R)-4-((2-Methoxyphenyl)(5-methyl-1H-pyrrol-2-yl)(thiophen-3-yl) methyl)phenol (Ij) was prepared as colorless oil from 4-(hydroxy(2-methoxyphenyl)(thiophen-3-yl)methyl)phenol (62.4 mg, 0.2 mmol) and 2-methylpyrrole (32.4 mg, 0.4 mmol) according to the General Procedure (at 40° C.) (eluent: hexanes/EtOAc=15:1 to 10:1) in 87% yield (65.5 mg, 87% ee).

$[\alpha]_D^{26}$: +10.3 (c=1.0, CHCl$_3$). HPLC analysis of the product: Daicel CHIRALPAK AD-H column; 5% i-PrOH in hexanes; 1.0 mL/min; retention times: 12.9 min (major), 14.8 min (minor).

$^1$H NMR (400 MHz, acetone-d$_6$) δ 8.87 (s, 1H), 8.20 (s, 1H), 7.29-7.24 (m, 2H), 6.97-6.92 (m, 3H), 6.86-6.81 (m, 3H), 6.78 (d, J=5.0 Hz, 1H), 6.69 (d, J=8.6 Hz, 2H), 5.66-5.61 (m, 1H), 5.55 (t, J=2.9 Hz, 1H), 3.27 (s, 3H), 2.14 (s, 3H).

$^{13}$C NMR (100 MHz, acetone-d$_6$) δ 159.0, 156.1, 148.2, 137.6, 137.6, 135.9, 131.3, 131.0, 130.4, 129.2, 127.5, 123.8, 123.3, 121.0, 114.6, 114.1, 109.7, 105.5, 56.1, 55.7, 13.1.

IR (thin film) 3443, 3393, 3049, 2837, 1587, 1251, 1175, 733, 703 cm$^{-1}$.

HRMS (LD+) Calcd for C$_{23}$H$_{21}$NO$_2$S (M$^+$): 375.1298, Found: 375.1311.

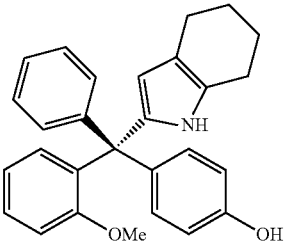

Ik (R)-4-((2-Methoxyphenyl)(phenyl)(4,5,6,7-tetrahydro-1H-indol-2-yl) methyl)phenol (Ik) was prepared as colorless oil from 4-(hydroxy(2-methoxyphenyl)(phenyl)methyl)phenol (61.2 mg, 0.2 mmol) and 4,5,6,7-tetrahydro-1H-indole (48.4 mg, 0.4 mmol) according to the General Procedure (eluent: hexanes/EtOAc=15:1 to 10:1) in 92% yield (75.1 mg, 83% ee).

$[\alpha]_D^{26}$: +0.8 (c=1.0, CHCl$_3$). HPLC analysis of the product: Daicel CHIRALPAK IC—H column; 3% i-PrOH in hexanes; 1.0 mL/min; retention times: 8.3 min (major), 9.3 min (minor).

$^1$H NMR (400 MHz, acetone-d$_6$) δ 8.47 (s, 1H), 8.23 (s, 1H), 7.28-7.21 (m, 6H), 7.03-6.85 (m, 5H), 6.70 (d, J=8.2 Hz, 2H), 5.46 (s, 1H), 3.16 (s, 3H), 2.45 (t, J=5.9 Hz, 2H), 2.40 (t, J=5.7 Hz, 2H), 1.72-1.69 (m, 4H).

$^{13}$C NMR (100 MHz, acetone-d$_6$) δ 158.9, 156.0, 146.9, 137.9, 136.6, 136.1, 132.1, 130.8, 130.5, 129.1, 127.5, 127.0, 126.1, 121.0, 115.5, 114.4, 114.0, 109.7, 59.1, 55.5, 24.8, 24.3, 23.7, 23.4.

IR (thin film) 3447, 3402, 3054, 2844, 1598, 1241, 1174, 733, 700 cm$^{-1}$.

HRMS (LD+) Calcd for C$_{28}$H$_{27}$NO$_2$ (M$^+$): 409.2042, Found: 409.2054.

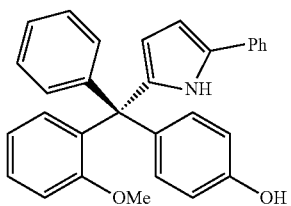

Il (R)-4-((2-Methoxyphenyl)(phenyl)(5-phenyl-1H-pyrrol-2-yl) methyl)phenol (Il) was prepared as colorless oil from 4-(hydroxy(2-methoxyphenyl)(phenyl)methyl)phenol (61.2 mg, 0.2 mmol) and 2-phenylpyrrole (57.2 mg, 0.4 mmol) according to the General Procedure (eluent: hexanes/EtOAc=15:1 to 10:1) in 98% yield (84.9 mg, 81% ee).

$[\alpha]_D^{26}$: +8.8 (c=1.0, CHCl$_3$). HPLC analysis of the product: Daicel CHIRALPAK OD-H column; 5% i-PrOH in hexanes; 1.0 mL/min; retention times: 11.2 min (minor), 12.2 min (major).

$^1$H NMR (400 MHz, acetone-d$_6$) δ 9.50 (s, 1H), 8.32 (s, 1H), 7.49 (d, J=7.8 Hz, 2H), 7.32-7.19 (m, 8H), 7.13-7.07 (m, 2H), 7.02-7.00 (m, 3H), 6.90 (t, J=7.6 Hz, 1H), 6.77 (d, J=8.6 Hz, 2H), 6.46 (t, J=2.9 Hz, 1H), 5.86 (t, J=2.8 Hz, 1H), 3.25 (s, 3H).

$^{13}$C NMR (100 MHz, acetone-d$_6$) δ 158.8, 156.2, 146.7, 139.8, 136.9, 136.4, 134.1, 132.3, 132.1, 131.0, 130.5, 129.4, 129.3, 127.7, 126.5, 126.1, 124.2, 121.2, 114.6, 114.3, 112.6, 105.8, 59.3, 55.7.

IR (thin film) 3449, 3366, 3054, 2836, 1600, 1254, 732, 697 cm$^{-1}$.

HRMS (LD+) Calcd for C$_{30}$H$_{25}$NO$_2$ (M$^+$): 431.1885, Found: 431.1876

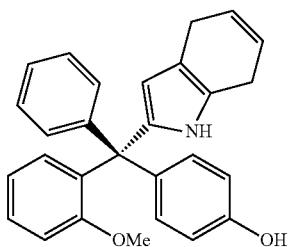

In (R)-4-((4,7-Dihydro-1H-indol-2-yl)(2-methoxyphenyl) (phenyl)methyl) phenol (In) was prepared as colorless foam solid from 4-(hydroxy(2-methoxyphenyl)(phenyl)methyl) phenol (61.2 mg, 0.2 mmol) and 4.7-dihydro-1H-indole (47.6 mg, 0.4 mmol, 2 equiv.) according to the General Procedure (eluent: hexanes/EtOAc=15:1 to 10:1) in 86% yield (70.4 mg, 86% ee).

$[\alpha]_D^{26}$: +2.2 (c=1.0, CHCl$_3$). HPLC analysis of the product: Daicel CHIRALPAKIC-H column; 3% i-PrOH in hexanes; 1.0 mL/min; retention times: 9.0 min (minor), 10.7 min (major).

$^1$H NMR (400 MHz, acetone-d$_6$) δ 8.66 (s, 1H), 8.21 (s, 1H), 7.29-7.14 (m, 6H), 7.02-6.86 (m, 5H), 6.72-6.69 (m, 2H), 5.85-5.82 (m, 1H), 5.79-5.76 (m, 1H), 5.53-5.52 (m, 1H), 3.15-3.10 (m, 4H), 3.17 (s, 3H).

$^{13}$C NMR (100 MHz, acetone-d$_6$) δ 158.9, 156.1, 146.9, 137.7, 137.0, 136.6, 132.1, 130.8, 130.5, 129.2, 127.6, 126.5, 126.2, 124.32, 124.27, 121.0, 114.4, 114.0, 112.7, 108.9, 59.2, 55.5, 25.6, 24.7.

IR (thin film) 3447, 3405, 2831, 1696, 1599, 1255, 1175, 1108, 820, 731 cm$^{-1}$.

HRMS (CI+) Calcd for C$_{28}$H$_{25}$NO$_2$ (M$^+$): 407.1885, Found: 407.1888.

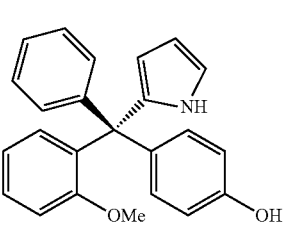

Im (R)-4-((2-Methoxyphenyl)(phenyl)(1H-pyrrol-2-yl) methyl)phenol (Im) was prepared as colorless oil from 4-(hydroxy(2-methoxyphenyl)(phenyl)methyl)phenol (61.2 mg, 0.2 mmol) and pyrrole (67.0 mg, 1.0 mmol, 5 equiv.) according to the General Procedure (eluent: hexanes/EtOAc=15:1 to 10:1) in 94% yield (66.8 mg, >99% ee).

$[\alpha]_D^{26}$: +3.6 (c=1.0, CHCl$_3$). HPLC analysis of the product: Daicel CHIRALPAK IC—H column; 2% i-PrOH in hexanes; 1.0 mL/min; retention times: 12.8 min (major >99%).

$^1$H NMR (400 MHz, acetone-d$_6$) δ 9.06 (s, 1H), 8.26 (s, 1H), 7.30-7.13 (m, 6H), 6.96-6.85 (m, 5H), 6.72-6.68 (m, 3H), 6.03-5.93 (m, 1H), 5.82-5.71 (m, 1H), 3.19 (s, 3H).

$^{13}$C NMR (100 MHz, acetone-d$_6$) δ 158.9, 156.1, 146.9, 137.9, 137.4, 136.7, 132.0, 130.7, 130.5, 129.3, 127.6, 126.3, 121.0, 118.1, 114.5, 114.0, 110.2, 107.3, 59.1, 55.5.

IR (thin film) 3447, 3055, 2835, 1598, 1241, 1176, 731 cm$^{-1}$.

HRMS (LD+) Calcd for C$_{24}$H$_{21}$NO$_2$ (M$^+$): 355.1572, Found: 355.1556.

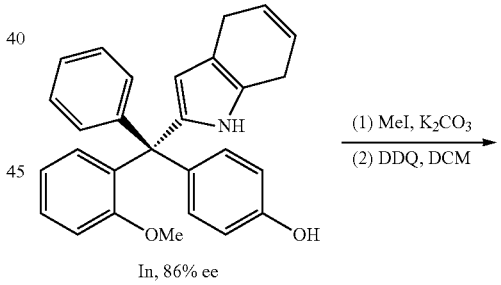

In, 86% ee

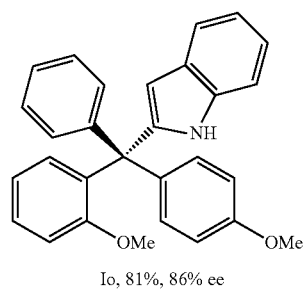

Io, 81%, 86% ee (R)-2-((2-Methoxyphenyl)(4-methoxyphenyl)(phenyl) methyl)-1H-indole Io). To a solution of In (61.1 mg, 0.15 mmol, 1.0 equiv.) in acetone (4 mL) was sequentially added MeI (64.4 mg, 0.45 mmol, 3.0 equiv.) and K$_2$CO$_3$ (104 mg, 0.75 mmol, 5.0 equiv.) at room temperature. The reaction mixture was stirred at room temperature for 24 h and filtered through a short pad of silica gel, which was washed with Et$_2$O. The filtrate was concentrated under reduced pressure. The crude product was dissolved in anhydrous DCM (8 mL). DDQ (38 mg, 0.175 mmol, 1.1 equiv.) was added in one portion. The reaction mixture was stirred at room temperature for 3 h. The reaction mixture was diluted with DCM (15 mL). Then it was washed with an aqueous solution of the solution of NaOH (15 mL, 10% wt.) and water (2×15 mL), and dried over Na$_2$SO$_4$. After that, the reaction mixture was concentrated under reduced pressure and purified by silica gel chromatography to afford the desired product (eluent: hexanes/EtOAc=15:1 to 10:1) in 81% yield for two steps (51.2 mg, 86% ee).

[α]$_D^{26}$: −1.5 (c=1.0, CHCl$_3$). HPLC analysis of the product: Daicel CHIRALPAK OD-H column; 3% i-PrOH in hexanes; 1.0 mL/min; retention times: 10.3 min (minor), 11.1 min (major).

$^1$H NMR (400 MHz, acetone-d$_6$) δ 9.46 (s, 1H), 7.46 (d, J=7.7 Hz, 1H), 7.28-7.18 (m, 6H), 7.09 (d, J=8.9 Hz, 2H), 7.03-6.88 (m, 5H), 6.82 (d, J=8.9 Hz, 2H), 6.34 (s, 1H), 3.77 (s, 3H), 3.20 (s, 3H).

$^{13}$C NMR (100 MHz, acetone-d$_6$) δ 159.0, 158.8, 146.0, 145.5, 137.7, 137.2, 136.1, 132.2, 130.81, 130.75, 129.7, 128.7, 127.9, 126.7, 121.7, 121.2, 120.7, 119.8, 114.0, 113.2, 111.8, 104.3, 59.6, 55.5, 55.4.

IR (thin film) 3448, 3053, 2836, 1592, 1290, 1105, 799, 731 cm$^{-1}$.

HRMS (CI+) Calcd for C$_{29}$H$_{25}$NO$_2$ (M)$^+$: 419.1885 Found: 419.1886.

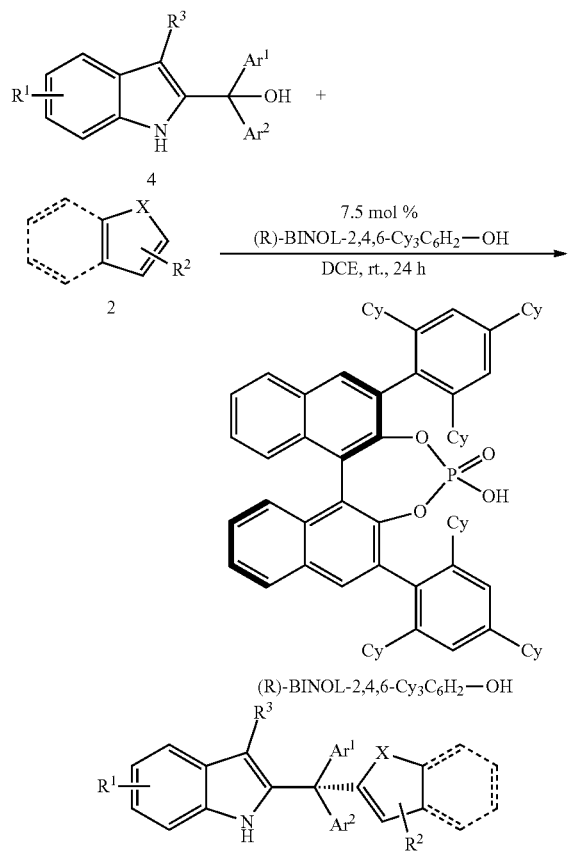

At room temperature, to an oven-dried 4-mL vial charged with a solution of tertiary alcohol 4 (0.2 mmol) and pyrrole 2 (0.4 mmol) in DCE (0.8 mL) was slowly added a solution of catalyst (R)-BINOL-2,4,6-Cy$_3$C$_6$H$_2$—OH (14.9 mg, 0.015 mmol, 7.5 mol %) in DCE (0.2 mL). The reaction mixture was stirred at the same temperature for 24 h. Next, Na$_2$CO$_3$ (212 mg, 2.0 mmol) was added. The mixture was stirred for 10 min and concentrated under reduced pressure. The residue was purified by silica gel chromatography to afford the desired product.

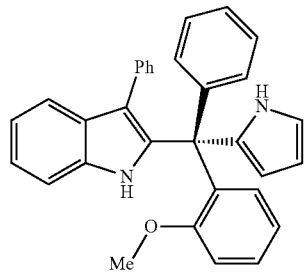

(S)-2-((2-Methoxyphenyl)(phenyl)(1H-pyrrol-2-yl)methyl)-3-phenyl-1H-indole (5a) was prepared as white foam from 4-(hydroxy(2-methoxyphenyl) (phenyl)methyl) phenol (81.3 mg, 0.2 mmol) and pyrrole (26.8 mg, 0.4 mmol) according to the General Procedure E (eluent: hexanes/EtOAc=20:1-? 15:1) in 96% yield (87.0 mg, 96% ee).

[α]$_D^{26}$: +0.5 (c=1.0, CHCl$_3$). HPLC analysis of the product: Daicel CHIRALPAK AD-H column; 5% i-PrOH in hexanes; 1.0 mL/min; retention times: 8.1 min (minor), 18.0 min (major).

$^1$H NMR (400 MHz, acetone-d$_6$) δ 9.42 (s, 1H), 9.32 (s, 1H), 7.41 (d, J=8.1 Hz, 1H), 7.26 (d, J=8.0 Hz, 1H), 7.24-7.06 (m, 7H), 7.02-6.86 (m, 7H), 6.78 (td, J$_1$=7.6 Hz, J$_2$=1.2 Hz, 1H), 6.70 (dd, J$_1$=8.2 Hz, J$_2$=1.2 Hz, 1H), 6.64 (td, J$_1$=2.7 Hz, J$_2$=1.6 Hz, 1H), 5.98 (dt, J$_1$=3.5 Hz, J$_2$=2.6 Hz, 1H), 5.84 (ddd, J$_1$=3.4 Hz, J$_2$=2.7 Hz, J$_3$=1.6 Hz, 1H), 3.19 (s, 3H).

$^{13}$C NMR (100 MHz, acetone-d$_6$) δ 158.6, 145.0, 137.6, 136.7, 135.5, 135.4, 135.0, 131.2, 130.9 (2C), 130.6, 129.6, 127.7, 127.5, 126.8, 125.7, 122.1, 120.7, 119.8, 119.6, 118.1, 116.3, 113.4, 111.8, 110.4, 107.8, 56.1, 55.5.

IR (thin film) 3412, 3055, 3008, 2935, 1591, 1543, 1245, 1089, 1022, 1089, 1022, 801, 745, 702 cm$^{-1}$.

HRMS (LD+) Calcd for C$_{32}$H$_{26}$N$_2$O (M$^+$): 454.2045, Found: 454.2052.

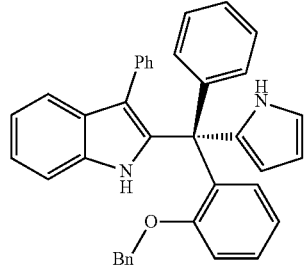

(S)-2-((2-(Benzyloxy)phenyl)(phenyl)(1H-pyrrol-2-yl)methyl)-3-phenyl-1H-indole (5b) was prepared as white foam from (2-(benzyloxy)phenyl) (phenyl)(3-phenyl-1H-indol-2-yl)methanol (96.2 mg, 0.2 mmol) and pyrrole (26.8 mg, 0.4 mmol) according to the General Procedure E (eluent: hexanes/EtOAc=20:1-? 15:1) in 81% yield (85.8 mg, 91% ee).

[α]$_D^{26}$: −2.2 (c=1.0, CHCl$_3$). HPLC analysis of the product: Daicel CHIRALPAK AD-H column; 10% i-PrOH in hexanes; 1.0 mL/min; retention times: 5.5 min (minor), 9.0 min (major).

$^1$H NMR (400 MHz, acetone-d$_6$) δ 9.42 (s, 1H), 9.35 (s, 1H), 7.37 (dd, J$_1$=8.1 Hz, J$_2$=2.1 Hz, 1H), 7.25-7.23 (m, 3H), 7.19-6.92 (m, 13H), 6.89-6.81 (m, 2H), 6.83-6.66 (m, 4H), 6.63-6.54 (m, 1H), 5.96-5.94 (m, 1H), 5.83-5.81 (m, 1H), 4.72 (d, J=12.0 Hz, 1H), 4.57 (d, J=12.1 Hz, 1H).

$^{13}$C NMR (100 MHz, acetone-d$_6$) δ 157.5, 144.8, 137.8, 137.5, 136.7, 135.6, 135.5, 134.5 131.3, 131.2, 131.0, 130.9, 129.6, 128.6, 127.9, 127.8, 127.6, 126.9, 125.8, 122.2, 120.8, 119.9, 119.6, 118.2, 116.2, 113.6, 111.9, 110.6, 107.9, 107.8 70.2, 56.3.

IR (thin film) 3414, 3054, 2961, 2926, 1591, 1485, 1447, 1292, 1230, 1093, 1019, 853, 737, 700 cm$^{-1}$.

HRMS (LD+) Calcd for C$_{38}$H$_{30}$N$_2$O (M$^+$): 530.2358, Found: 530.2350.

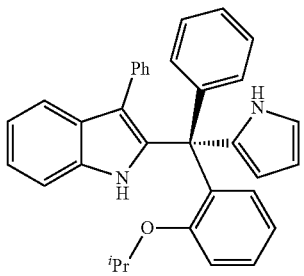

5c (S)-2-((2-Isopropoxyphenyl)(phenyl)(1H-pyrrol-2-yl)methyl)-3-phenyl-1H-indole (5c) was prepared as white foam from (2-isopropoxyphenyl)(phenyl) (3-phenyl-1H-indol-2-yl)methanol (86.7 mg, 0.2 mmol) and pyrrole (26.8 mg, 0.4 mmol) according to the General Procedure E (eluent: hexanes/EtOAc=20:1-? 15:1) in 92% yield (88.9 mg, 92% ee).

[α]$_D^{26}$:−9.4 (c=1.0, CHCl$_3$). HPLC analysis of the product: Daicel CHIRALPAK AD-H column; 10% i-PrOH in hexanes; 1.0 mL/min; retention times: 7.0 min (minor), 15.0 min (major).

$^1$H NMR (400 MHz, acetone-d$_6$) δ 9.47 (s, 1H), 9.28 (s, 1H), 7.42 (d, J=8.1 Hz, 1H), 7.34-7.05 (m, 8H), 7.02-6.87 (m, 7H), 6.73 (t, J=IF Hz, 2H), 6.61 (td, J$_1$=2.7 Hz, J$_2$=1.6 Hz, 1H), 5.95 (q, J=2.8 Hz, 1H), 5.81 (td, J$_1$=3.1 Hz, J$_2$=1.6 Hz, 1H), 4.35 (hept, J=6.0 Hz, 1H), 0.83 (d, J=6.0 Hz, 3H), 0.63 (d, J=5.9 Hz, 3H).

$^{13}$C NMR (100 MHz, acetone-d$_6$) δ 156.0, 144.9, 138.0, 136.8, 135.4, 135.3, 135.0, 131.4, 131.2, 130.9, 130.9, 129.4, 127.6, 127.6, 126.7, 125.7, 122.1, 119.8, 119.7, 119.6, 117.9, 116.2, 113.0, 111.8, 110.6, 107.8, 68.6, 56.3, 21.6, 20.9.

IR (thin film) 3445, 3417, 3056, 2976, 2929, 1592, 1483, 1449, 1289, 1242, 1118, 952, 751, 705 cm$^{-1}$.

HRMS (LD+) Calcd for C$_{34}$H$_{30}$N$_2$O (M$^+$): 482.2358, Found: 482.2339.

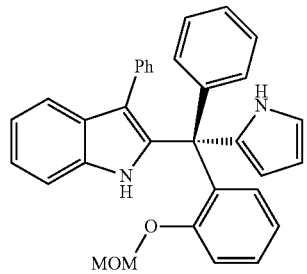

5d (S)-2-((2-(Methoxymethoxy)phenyl)(phenyl)(1H-pyrrol-2-yl)methyl)-3-phenyl-1H-indole (5d) was prepared as white foam from (2-(methoxymethoxy) phenyl)(phenyl)(3-phenyl-1H-indol-2-yl)methanol (87.1 mg, 0.2 mmol) and pyrrole (26.8 mg, 0.4 mmol) according to the General Procedure E (eluent: hexanes/EtOAc=20:1-? 15:1) in 78% yield (75.9 mg, 97% ee).

[α]$_D^{26}$:−1.9 (c=1.0, CHCl$_3$). HPLC analysis of the product: Daicel CHIRALPAK AD-H column; 10% i-PrOH in hexanes; 1.0 mL/min; retention times: 4.5 min (minor), 12.0 min (major).

$^1$H NMR (400 MHz, acetone-d$_6$) δ 9.47 (s, 1H), 9.32 (s, 1H), 7.41 (d, J=8.1 Hz, 1H), 7.26-7.19 (m, 3H), 7.17-7.04 (m, 5H), 7.01-6.78 (m, 9H), 6.64-6.64 (m, 1H), 5.99-5.96 (m, 1H), 5.86-5.83 (m, 1H), 4.51 (d, J=6.9 Hz, 1H), 4.45 (d, J=6.9 Hz, 1H), 2.81 (s, 3H).

$^{13}$C NMR (100 MHz, acetone-d$_6$) δ 156.7, 145.0, 137.5, 136.7, 135.6, 135.5, 135.3, 131.3, 131.0, 130.9, 130.7, 129.6, 127.8, 127.6, 126.8, 125.8, 122.2, 121.6, 119.9, 119.6, 118.3, 116.4, 115.6, 111.9, 110.4, 107.9, 94.78, 56.3, 55.6.

IR (thin film) 3443, 3054, 2954, 2933, 1592, 1484, 1234, 1153, 1078, 996, 917, 737, 705 cm$^{-1}$.

HRMS (LD+) Calcd for C$_{33}$H$_{28}$N$_2$O$_2$ (M$^+$): 484.2151, Found: 484.2168.

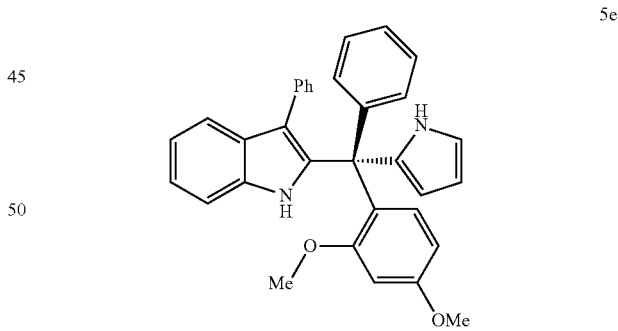

5e (S)-2-((2,4-Dimethoxyphenyl)(phenyl)(1H-pyrrol-2-yl)methyl)-3-phenyl-1H-indole (5e) was prepared as white foam from (2,4-dimethoxyphenyl) (phenyl)(3-phenyl-1H-indol-2-yl)methanol (87.0 mg, 0.2 mmol) and pyrrole (26.8 mg, 0.4 mmol) according to the General Procedure E (eluent: hexanes/EtOAc=20:1-? 15:1) in 94% yield (91.3 mg, 96% ee).

[α]$_D^{26}$:−4.6 (c=1.0, CHCl$_3$). HPLC analysis of the product: Daicel CHIRALPAK AD-H column; 10% i-PrOH in hexanes; 1.0 mL/min; retention times: 6.7 min (minor), 14.6 min (major).

$^1$H NMR (400 MHz, CD$_2$Cl$_2$) δ 8.45 (s, 1H), 8.42 (s, 1H), 7.38 (d, J=7.9 Hz, 1H), 7.32 (d, J=8.1 Hz, 1H), 7.23-7.14 (m, 6H), 7.10-7.00 (m, 4H), 6.92-6.89 (m, 3H), 6.61-6.59 (m, 1H), 6.36-6.33 (m, 2H), 6.13-6.10 (m, 1H), 5.91-5.00 (m, 1H), 3.78 (s, 3H), 3.33 (s, 3H).

$^{13}$C NMR (100 MHz, CD$_2$Cl$_2$) δ 161.0, 158.9, 144.3, 137.6, 135.7, 135.6, 134.3, 131.8, 130.8, 130.5, 130.4, 127.8, 127.4, 126.9, 126.0, 125.6, 122.2, 120.0, 119.6, 117.0, 115.8, 111.0, 109.9, 108.3, 104.5, 100.7, 55.9, 55.7, 55.2.

IR (thin film) 3434, 3410, 3052, 2926, 2843, 1606, 1493, 1451, 1414, 1301, 1260, 1030, 735, 701 cm$^{-1}$.

HRMS (LD+) Calcd for C$_{33}$H$_{28}$N$_2$O$_2$ (M$^+$): 484.2151, Found: 484.2163.

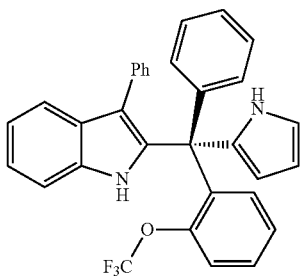

5f (S)-3-Phenyl-2-(phenyl(1H-pyrrol-2-yl)(2-(trifluoromethoxy)phenyl)methyl)-1H-indole (5f) was prepared as white foam from phenyl(3-phenyl-1H-indol-2-yl)(2-(trifluoromethoxy)phenyl)methanol (91.9 mg, 0.2 mmol) and pyrrole (26.8 mg, 0.4 mmol) according to the General Procedure E (7.5 mol % catalyst) (eluent: hexanes/EtOAc=20:1-? 15:1) in 85% yield (86.5 mg, 94% ee).

$[\alpha]_D^{26}$: +14.1 (c=1.0, CHCl$_3$). HPLC analysis of the product: Daicel CHIRALPAK AD-H column; 10% i-PrOH in hexanes; 1.0 mL/min; retention times: 4.0 min (minor), 11.8 min (major).

$^1$H NMR (400 MHz, acetone-d$_6$) δ 9.58 (s, 1H), 9.45 (s, 1H), 7.43 (d, J=8.2 Hz, 1H), 7.27-7.04 (m, 10H), 7.01-6.93 (m, 4H), 6.89-6.86 (m, 3H), 6.73-6.71 (m, 1H), 6.03-6.01 (m, 1H), 5.90-5.88 (m, 1H).

$^{13}$C NMR (100 MHz, acetone-d$_6$) δ 149.2, 144.2, 136.8, 136.3, 136.1, 135.8, 134.4, 131.9, 131.4, 130.9, 130.4, 123.0, 128.2, 127.7, 127.2, 126.0, 125.7, 122.6, 120.7 (q, J=255.9 Hz), 120.0, 119.8, 119.1, 117.8 (q, J=2.2 Hz), 117.2, 112.0, 110.7, 108.1, 56.1.

$^{19}$F NMR (376 MHz, acetone-d$_6$) δ −56.3.

IR (thin film) 3445, 3055, 1487, 1449, 1251, 1212, 1160, 898, 739, 704 cm$^{-1}$.

HRMS (LD+) Calcd for C$_{32}$H$_{23}$F$_3$N$_2$O (M$^+$): 508.1762, Found: 508.1745.

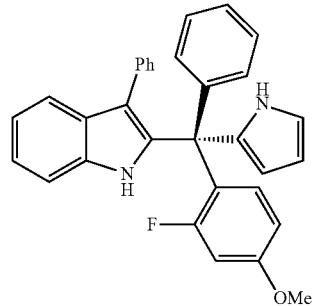

5g (S)-2-((2-Fluoro-4-methoxyphenyl)(phenyl)(1H-pyrrol-2-yl)methyl)-3-phenyl-1H-indole (5g) was prepared as white foam from (2-fluoro-4-methoxyphenyl)(phenyl)(3-phenyl-1H-indol-2-yl)methanol (84.7 mg, 0.2 mmol) and pyrrole (26.8 mg, 0.4 mmol) according to the General Procedure E (eluent: hexanes/EtOAc=20:1→15:1) in 95% yield (89.9 mg, 92% ee).

$[\alpha]_D^{26}$: +12.4 (c=1.0, CHCl$_3$). HPLC analysis of the product: Daicel CHIRALPAK AD-H column; 7% i-PrOH in hexanes; 1.0 mL/min; retention times: 24.4 min (minor), 25.4 min (major).

$^1$H NMR (400 MHz, acetone-d$_6$) δ 9.49 (s, 1H), 9.47-9.42 (m, 1H), 7.41 (d, J=8.2 Hz, 1H), 7.23-7.15 (m, 6H), 7.12-7.08 (m, 1H), 7.03-6.94 (m, 4H), 6.93-6.88 (m, 2H), 6.83 (t, J=9.0 Hz, 1H), 6.70-6.68 (m, 1H), 6.54 (dd, J$_1$=8.9, J$_2$=2.6 Hz, 1H), 6.26 (dd, J=13.0, J$_1$=2.6 Hz, 1H), 6.02-6.00 (m, 1H), 5.92-5.90 (m, 1H), 3.72 (s, 3H).

$^{13}$C NMR (100 MHz, acetone-d$_6$) δ 162.2 (d, J=247.5 Hz), 161.5 (d, J=10.0 Hz), 144.8, 136.8, 136.4, 135.7, 134.8, 131.7 (d, J=5.3 Hz), 131.4, 130.9, 130.4, 128.3, 127.7, 127.4, 125.9, 125.6 (d, J=12.3 Hz), 122.5, 120.0, 119.8, 118.8, 116.9, 112.0, 110.4 (d, J=2.0 Hz), 109.5 (d, J=2.7 Hz), 108.0, 103.0 (d, J=26.4 Hz), 55.8, 54.8.

$^{19}$F NMR (376 MHz, acetone-d$_6$) δ −100.4.

IR (thin film) 4039, 3054, 3024, 2962, 1617, 1578, 1497, 1450, 1306, 1260, 1158, 740, 706 cm$^{-1}$.

HRMS (LD+) Calcd for C$_{32}$H$_{25}$FN$_2$O (M$^+$): 472.1951, Found: 472.1943.

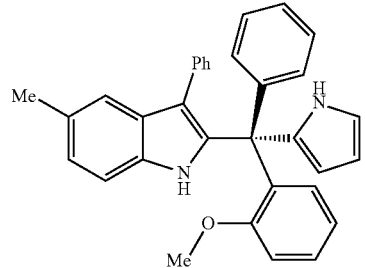

5h (S)-2-((2-Methoxyphenyl)(phenyl)(1H-pyrrol-2-yl)methyl)-5-methyl-3-phenyl-1H-indole (5h) was prepared as white foam from (2-methoxyphenyl) (6-methyl-3-phenyl-1H-indol-2-yl)(phenyl)methanol (83.9 mg, 0.2 mmol) and pyrrole (26.8 mg, 0.4 mmol) according to the General Procedure E (eluent: hexanes/EtOAc=20:1-? 15:1) in 67% yield (62.6 mg, 94% ee).

$[\alpha]_D^{26}$: +0.8 (c=1.0, CHCl$_3$). HPLC analysis of the product: Daicel CHIRALPAK AD-H column; 10% i-PrOH in hexanes; 1.0 mL/min; retention times: 7.4 min (minor), 10.9 min (major).

$^1$H NMR (400 MHz, acetone-d$_6$) δ 9.29 (s, 1H), 9.27 (s, 1H), 7.28 (d, J=8.2 Hz, 1H), 7.21-7.08 (m, 6H), 7.00 (s, 1H), 6.97-6.83 (m, 7H), 6.76 (td, J$_1$=7.6 Hz, J2=1.2 Hz, 1H), 6.71 (dd, J$_1$=8.2 Hz, J$_2$=1.2 Hz, 1H), 6.63-6.61 (m, 1H), 5.95 (dt, J$_1$=3.4 Hz, J$_2$=2.5 Hz, 1H), 5.79 (dd, J$_1$=3.3 Hz, J$_2$=1.6 Hz, 1H), 3.19 (s, 3H), 2.32 (s, 3H).

$^{13}$C NMR (100 MHz, acetone-d$_6$) δ 158.7, 145.1, 137.8, 136.9, 135.64, 135.1, 133.9, 131.3, 131.2, 131.0, 130.7, 129.7, 128.6, 127.7, 127.6, 126.8, 125.7, 123.7, 120.8, 119.2, 118.1, 115.9, 113.5, 111.6, 110.4, 107.8, 56.2, 55.5, 21.6.

IR (thin film) 3442, 3421, 3051, 3023, 2961, 1591, 1543, 1250, 1088, 1021, 797, 733, 702 cm$^{-1}$.

HRMS (LD+) Calcd for C$_{33}$H$_{28}$N$_2$O (M$^+$): 468.2202, Found: 468.2214.

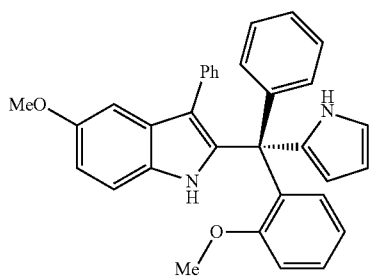

5i (S)-5-Methoxy-2-((2-methoxyphenyl)(phenyl)(1H-pyrrol-2-yl)methyl)-3-phenyl-1H-indole (5i) was prepared as white foam from (6-methoxy-3-phenyl-1H-indol-2-yl)(2-methoxyphenyl)(phenyl)methanol (87.1 mg, 0.2 mmol) and pyrrole (26.8 mg, 0.4 mmol) according to the General Procedure E (using 4 mL of DCM, 36 h) (eluent: hexanes/EtOAc=20:1-? 15:1) in 78% yield (75.8 mg, 96% ee).

[α]$_D$$^{26}$:−1.5 (c=1.0, CHCl$_3$). HPLC analysis of the product: Daicel CHIRALPAK AD-H column; 10% i-PrOH in hexanes; 1.0 mL/min; retention times: 8.1 min (minor), 13.8 min (major).

$^1$H NMR (400 MHz, acetone-d$_6$) δ 9.28 (s, 1H), 9.24 (s, 1H), 7.30 (d, J=8.5 Hz, 1H), 7.21-7.08 (m, 6H), 6.99-6.93 (m, 4H), 6.89-6.83 (m, 2H), 6.79-6.71 (m 4H), 6.63-6.61 (m, 1H), 5.97-5.95 (m, 1H), 5.85-5.73 (m, 1H), 3.67 (s, 3H), 3.20 (s, 3H).

$^{13}$C NMR (100 MHz, acetone-d$_6$) δ 158.7, 155.1, 145.0, 138.5, 136.9, 135.6, 135.1, 131.2 (2C), 131.0, 130.7, 130.6, 129.7, 127.72, 127.69, 126.8, 125.8, 120.8, 118.1, 116.1, 113.5, 112.6, 112.3, 110.4, 107.9, 101.5, 56.3, 55.8, 55.5.

IR (thin film) 3442, 3054, 2942, 2832, 1589, 1482, 1443, 1255, 1150, 1027, 799, 738, 706 cm$^{-1}$.

HRMS (LD+) Calcd for C$_{33}$H$_{28}$N$_2$O$_2$ (M$^+$): 484.2151, Found: 484.2138.

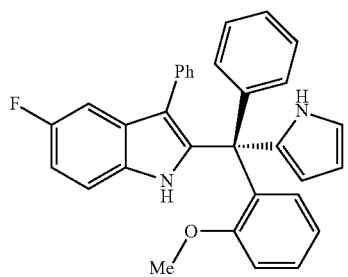

5j (A)-5-Fluoro-2-((2-methoxyphenyl)(phenyl)(1H-pyrrol-2-yl)methyl)-3-phenyl-1H-indole (5j) was prepared as white foam from (6-fluoro-3-phenyl-1H-indol-2-yl)(2-methoxyphenyl)(phenyl)methanol (84.7 mg, 0.2 mmol) and pyrrole (26.8 mg, 0.4 mmol) according to the General Procedure E (using 4 mL of DCM, 36 h) (eluent: hexanes/EtOAc=20:1-? 15:1) in 68% yield (63.8 mg, 95% ee).

[α]$_D$$^{26}$: −3.2 (c=1.0, CHCl$_3$). HPLC analysis of the product: Daicel CHIRALPAK AD-H column; 10% i-PrOH in hexanes; 1.0 mL/min; retention times: 6.6 min (minor), 8.3 min (major).

$^1$H NMR (400 MHz, CD$_2$Cl$_2$) δ 8.48 (s, 1H), 8.39 (s, 1H), 7.28-7.14 (m, 7H), 7.01-6.97 (m, 5H), 6.91 (td, J$_1$=9.1 Hz, J$_2$=2.5 Hz, 1H), 6.84-6.77 (m, 4H), 6.60-6.58 (m, 1H), 6.09-6.07 (m, 1H), 5.86-5.82 (m, 1H), 3.31 (s, 3H).

$^{13}$C NMR (100 MHz, CD$_2$Cl$_2$) δ 158.5 (d, J=231.9 Hz), 158.1, 143.6, 139.4, 135.1 (d, J=14.6 Hz), 133.3, 131.0, 130.8, 130.6, 130.4, 129.5, 127.8, 127.6, 127.1, 125.9, 121.0, 117.2, 116.1 (d, J=4.7 Hz), 113.4, 111.8 (d, J=9.6 Hz), 110.4, 110.1, 108.4, 108.1, 104.3 (d, J=23.8 Hz), 103.9, 56.0, 55.8.

$^{19}$F NMR (376 MHz, CD$_2$Cl$_2$) δ −128.6.

IR (thin film) 3439, 3411, 2054, 2935, 2834, 1588, 1481, 1440, 1249, 1102, 1022, 907, 857, 751, 704 cm$^{-1}$.

HRMS (LD+) Calcd for C$_{32}$H$_{25}$FN$_2$O (M$^+$): 472.1951, Found: 472.1963.

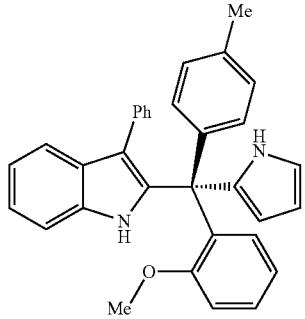

5k (S)-2-((2-Methoxyphenyl)(1H-pyrrol-2-yl)(p-tolyl)methyl)-3-phenyl-1H-indole (5k) was prepared as white foam from (2-methoxyphenyl) (3-phenyl-1H-indol-2-yl)(p-tolyl)methanol (81.9 mg, 0.2 mmol) and pyrrole (26.8 mg, 0.4 mmol) according to the General Procedure E (eluent: hexanes/EtOAc=20:1-? 15:1) in 96% yield (90.2 mg, 92% ee).

[α]$_D$$^{26}$:−1.5 (c=1.0, CHCl$_3$). HPLC analysis of the product: Daicel CHIRALPAK AD-H column; 10% i-PrOH in hexanes; 1.0 mL/min; retention times: 5.3 min (minor), 11.4 min (major).

$^1$H NMR (400 MHz, acetone-d$_6$) δ 9.38 (s, 1H), 9.29 (s, 1H), 7.40 (d, J=8.0 Hz, 1H), 7.27 (d, J=8.0 Hz, 1H), 7.17-6.85 (m, 13H), 6.79-6.75 (m, 1H), 6.71 (d, J=2.8 Hz, 1H), 6.65-6.59 (m, 1H), 5.99 (d, J=8.0 Hz, 1H), 5.84-5.87 (m, 1H), 3.21 (s, 3H), 2.26 (s, 3H).

$^{13}$C NMR (100 MHz, acetone-d$_6$) δ 158.7 141.9, 137.9, 136.7 136.0, 135.7, 135.4, 134.9, 131.2, 130.9, 130.7 (2C), 129.5, 128.4, 127.5, 125.6, 122.0, 120.7, 119.8, 119.5, 118.0, 116.0, 113.4, 111.8, 110.3, 107.8, 55.8, 55.5, 21.0.

IR (thin film) 3436, 3423, 3051, 3019, 2961, 2929, 2590, 1484, 1251, 1180, 1092, 1021, 804, 740, 704 cm$^{-1}$.

HRMS (LD+) Calcd for C$_{33}$H$_{28}$N$_2$O (M$^+$): 468.2202, Found: 468.2213.

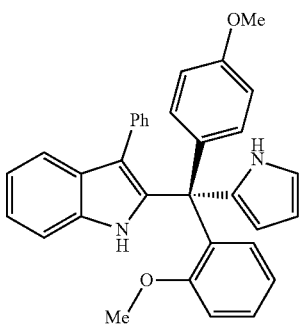

51

(S)-2-((2-Methoxyphenyl)(4-methoxyphenyl)(1H-pyrrol-2-yl)methyl)-3-phenyl-1H-indole (51) was prepared as white foam from (2-methoxyphenyl) (4-methoxyphenyl)(3-phenyl-1H-indol-2-yl)methanol (87.1 mg, 0.2 mmol) and pyrrole (26.8 mg, 0.4 mmol) according to the General Procedure E (eluent: hexanes/EtOAc=20:1-? 15:1) in 78% yield (75.7 mg, 86% ee).

$[\alpha]_D^{26}$: −1.5 (c=1.0, CHCl$_3$). HPLC analysis of the product: Daicel CHIRALPAK OD-H column; 5% i-PrOH in hexanes; 1.0 mL/min; retention times: 7.9 min (minor), 9.3 min (major).

$^1$H NMR (400 MHz, acetone-d$_6$) δ 9.37 (s, 1H), 9.29 (s, 1H), 7.40 (d, J=8.1 Hz, 1H), 7.29-7.03 (m, 5H), 7.03-6.83 (m, 7H), 6.80-6.57 (m, 5H), 5.98-5.96 (m, 1H), 5.83-5.81 (m, 1H), 3.72 (s, 3H), 3.23 (s, 3H).

$^{13}$C NMR (100 MHz, acetone) δ 158.8, 158.7, 138.2, 136.8, 136.7, 136.0, 135.4, 135.1, 131.9, 131.3, 130.91, 130.88, 129.6, 127.6, 125.7, 122.1, 120.8, 119.8, 119.5, 118.0, 115.9, 113.4, 113.0, 111.8, 110.3, 107.8, 55.6, 55.5, 55.4.

IR (thin film) 3435, 3413, 3049, 2958, 2835, 1595, 1452, 1245, 1177, 1095, 1024, 800, 729, 703 cm$^{-1}$.

HRMS (LD+) Calcd for C$_{33}$H$_{28}$N$_2$O$_2$ (M$^+$): 484.2151, Found: 484.2168.

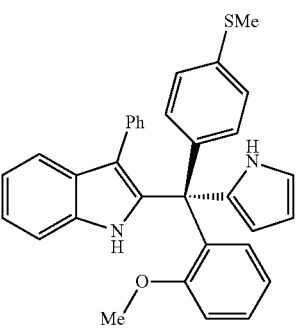

5m (S)-2-((2-Methoxyphenyl)(4-(methylthio)phenyl)(1H-pyrrol-2-yl)methyl)-3-phenyl-1H-indole (5m) was prepared as white foam from (2-methoxyphenyl) (4-(methylthio)phenyl)(3-phenyl-1H-indol-2-yl)methanol (90.2 mg, 0.2 mmol) and pyrrole (26.8 mg, 0.4 mmol) according to the General Procedure E (using 4 mL of DCM, 36 h) (eluent: hexanes/EtOAc=20:1→15:1) in 71% yield (70.9 mg, 83% ee).

$[\alpha]_D^{26}$: −4.8 (c=1.0, CHCl$_3$). HPLC analysis of the product: Daicel CHIRALPAK AD-H column; 10% i-PrOH in hexanes; 1.0 mL/min; retention times: 6.3 min (minor), 10.8 min (major).

$^1$H NMR (400 MHz, Acetone-d$_6$) δ 9.40 (s, 1H), 9.32 (s, 1H), 7.40 (d, J=8.1 Hz, 1H), 7.23-7.16 (m, 2H), 7.10-7.06 (m, 3H), 7.03-6.84 (m, 9H), 6.79 (t, J=7.6 Hz, 1H), 6.74 (d, J=8.1 Hz, 1H), 6.67-6.62 (m, 1H), 5.99-5.96 (m, 1H), 5.84-5.82 (m, 1H), 3.23 (s, 3H), 2.42 (s, 3H).

$^{13}$C NMR (100 MHz, Acetone) δ 158.7, 141.6, 137.8, 136.82, 136.77, 135.6, 135.5, 134.9, 131.4, 131.3, 131.0, 130.9, 129.7, 127.6, 125.8, 125.7, 122.2, 120.9, 119.9, 119.6, 118.2, 116.2, 113.5, 111.9, 110.4, 107.9, 55.9, 55.6, 15.6.

IR (thin film) 3437, 3051, 2927, 2834, 1590, 1485, 1450, 1250, 1023, 812, 739, 708 cm$^{-1}$.

HRMS (LD+) Calcd for C$_{33}$H$_{28}$N$_2$OS (M$^+$): 500.1922, Found: 500.1904.

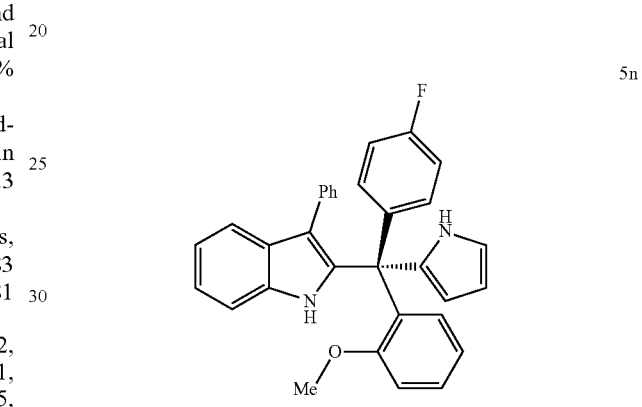

5n (S)-2-((4-Fluorophenyl)(2-methoxyphenyl)(1H-pyrrol-2-yl)methyl)-3-phenyl-1H-indole (5n) was prepared as white foam from (4-fluorophenyl) (2-methoxyphenyl)(3-phenyl-1H-indol-2-yl)methanol (84.7 mg, 0.2 mmol) and pyrrole (26.8 mg, 0.4 mmol) according to the General Procedure E (using 4 mL of DCM, 36 h) (eluent: hexanes/EtOAc=20:1-? 15:1) in 68% yield (63.8 mg, 95% ee).

$[\alpha]_D^{26}$: +7.4 (c=1.0, CHCl$_3$). HPLC analysis of the product: Daicel CHIRALPAK AD-H column; 10% i-PrOH in hexanes; 1.0 mL/min; retention times: 6.6 min (minor), 14.5 min (major).

$^1$H NMR (400 MHz, acetone-d$_6$) δ 9.45 (s, 1H), 9.38 (s, 1H), 7.40 (d, J=8.1 Hz, 1H), 7.24-7.13 (m, 4H), 7.11-7.06 (m, 1H), 7.00-6.90 (m, 5H), 6.88-6.73 (m, 6H), 6.67-6.65 (m, 1H), 6.00-5.97 (m, 1H), 5.83-5.81 (m, 1H), 3.23 (s, 3H).

$^{13}$C NMR (100 MHz, acetone-d$_6$) δ 161.9 (d, J=241.7 Hz), 158.6, 140.5 (d, J=3.3 Hz), 137.6, 136.7, 135.6, 135.5, 135.1, 132.5 (d, J=7.9 Hz), 131.3, 130.9, 130.8, 129.9, 127.7, 125.8, 122.3, 120.9, 119.9, 119.7, 118.4, 116.4, 114.0 (d, J=21.0 Hz), 113.5, 111.9, 110.3, 107.9, 55.8, 55.5.

$^{19}$F NMR (376 MHz, acetone-d$_6$) δ −119.1.

IR (thin film) 3441, 3415, 3052, 2934, 2837, 1595, 1494, 1236, 1164, 1098, 1023, 821, 741, 706 cm$^{-1}$.

HRMS (LD+) Calcd for C$_{32}$H$_{25}$FN$_2$O (M$^+$): 472.1951, Found: 472.1971.

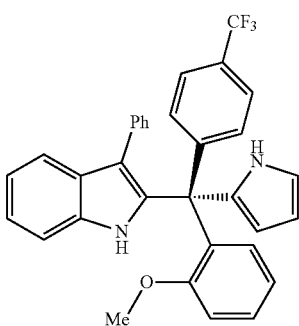

(S)-2-((2-Methoxyphenyl)(1H-pyrrol-2-yl)(4-(trifluoromethyl)phenyl)methyl)-3-phenyl-1H-indole (5o) was prepared as white foam from (2-methoxyphenyl)(3-phenyl-1H-indol-2-yl)(4-(trifluoromethyl)phenyl)methanol (94.7 mg, 0.2 mmol) and pyrrole (26.8 mg, 0.4 mmol) according to the General Procedure E (under 40° C. 36 h) (eluent: hexanes/EtOAc=20:1→15:1) in 85% yield (84.1 mg, 83% ee).

$[\alpha]_D^{26}$: +14.5 (c=1.0, CHCl$_3$). HPLC analysis of the product: Daicel CHIRALPAK AD-H column; 10% i-PrOH in hexanes; 1.0 mL/min; retention times: 4.0 min (minor), 6.2 min (major).

$^1$H NMR (400 MHz, acetone-d$_6$) δ 9.54 (s, 1H), 9.50 (s, 1H), 7.41 (d, J=8.1 Hz, 1H), 7.38-7.33 (m, 4H), 7.27-7.19 (m, 2H), 7.13-7.09 (m, 1H), 7.01-6.95 (m, 5H), 6.90-6.83 (m, 3H), 6.78 (d, J=8.2 Hz, 1H), 6.72-6.69 (m, 1H), 6.05-6.00 (m, 1H), 5.86-5.84 (m, 1H), 3.22 (s, 3H).

$^{13}$C NMR (100 MHz, acetone-d$_6$) δ 158.4, 148.8, 136.9, 136.6, 135.5, 135.0, 134.8, 131.33, 131.32, 130.90, 130.89, 130.1, 128.2 (q, J=31.6 Hz), 127.7, 126.0, 125.5 (q, 0.7=269.6 Hz), 124.2 (q, 0.7=3.9 Hz), 122.4, 121.1, 120.0, 119.7, 118.7, 116.8, 113.5, 111.9, 110.4, 108.1, 56.3, 55.4.

$^{19}$F NMR (376 MHz, acetone-d$_6$) δ −62.6.

IR (thin film) 3436, 3416, 3054, 2961, 2837, 1590, 1483, 1324, 1164, 1116, 1018, 801, 737, 705 cm$^{-1}$.

HRMS (LD+) Calcd for C$_{33}$H$_{25}$F$_3$N$_2$O (M$^+$): 522.1919, Found: 522.1934.

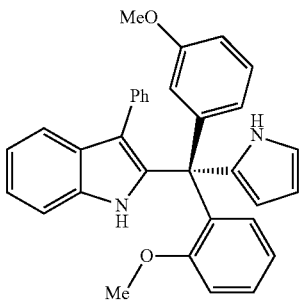

(S)-2-((2-Methoxyphenyl)(3-methoxyphenyl)(1H-pyrrol-2-yl)methyl)-3-phenyl-1H-indole (5p) was prepared as white foam from (2-methoxyphenyl)(3-methoxyphenyl)(3-phenyl-1H-indol-2-yl)methanol (87.1 mg, 0.2 mmol) and pyrrole (26.8 mg, 0.4 mmol) according to the General Procedure E (eluent: hexanes/EtOAc=20:1-? 15:1) in 90% yield (87.5 mg, 96% ee).

$[\alpha]_D^{26}$: +6.5 (c=1.0, CHCl$_3$). HPLC analysis of the product: Daicel CHIRALPAK AD-H column; 10% i-PrOH in hexanes; 1.0 mL/min; retention times: 5.5 min (minor), 9.1 min (major).

$^1$H NMR (400 MHz, Acetone-d$_6$) δ 9.43 (s, 1H), 9.31 (s, 1H), 7.41 (d, J=8.1 Hz, 1H), 7.28-7.25 (m, 1H), 7.20-7.14 (m, 1H), 7.11-6.90 (m, 9H), 6.83-6.67 (m, 5H), 6.64-6.62 (m, 1H), 5.99-5.97 (m, 1H), 5.88-5.86 (m, 1H), 3.60 (s, 3H), 3.22 (s, 3H).

$^{13}$C NMR (100 MHz, Acetone) δ 159.7, 158.8, 146.5, 137.7, 136.7, 135.4, 135.3, 134.9, 131.2, 130.94, 130.87, 129.7, 128.6, 127.6, 125.7, 123.3, 122.2, 120.9, 119.9, 119.6, 118.0, 117.3, 116.2, 113.4, 111.85, 111.78, 110.4, 107.9, 56.2, 55.6, 55.2.

IR (thin film) 3437, 3052, 2939, 2834, 1593, 1483, 1244, 1178, 1028, 799, 739, 704 cm$^{-1}$.

HRMS (LD+) Calcd for C$_{33}$H$_{28}$N$_2$O$_2$ (M$^+$): 484.2151, Found: 484.2170.

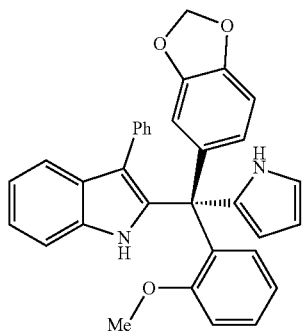

(S)-2-(Benzo[d][1,3]dioxol-5-yl(2-methoxyphenyl)(1H-pyrrol-2-yl)methyl)-3-phenyl-1H-indole (5q) was prepared as white foam from benzo[d][1,3]dioxol-5-yl(2-methoxyphenyl)(3-phenyl-1H-indol-2-yl)methanol (89.9 mg, 0.2 mmol) and pyrrole (26.8 mg, 0.4 mmol) according to the General Procedure E (eluent: hexanes/EtOAc=20:1→15:1) in 90% yield (90.0 mg, 94% ee).

$[\alpha]_D^{26}$: +10.8 (c=1.0, CHCl$_3$). HPLC analysis of the product: Daicel CHIRALPAK AD-H column; 10% i-PrOH in hexanes; 1.0 mL/min; retention times: 6.6 min (minor), 15.1 min (major).

$^1$H NMR (400 MHz, acetone-d$_6$) δ 9.44 (s, 1H), 9.35 (s, 1H), 7.40 (d, J=8.1, 1H), 7.24-7.15 (m, 2H), 7.10-7.06 (m, 1H), 7.02-6.86 (m, 7H), 6.82-6.75 (m, 2H), 6.68-6.62 (m, 2H), 6.57-6.54 (m, 2H), 5.99-5.96 (m, 1H), 5.86-5.83 (m, 3H), 3.27 (s, 3H).

$^{13}$C NMR (100 MHz, acetone-d$_6$) δ 158.8, 147.5, 146.6, 138.5, 138.1, 136.9, 135.7, 135.4, 135.1, 131.2, 130.92, 130.90, 129.7, 127.6, 125.7, 124.1, 122.2, 120.9, 119.9, 119.6, 118.1, 116.2, 113.6, 111.9, 111.8, 110.3, 107.9, 107.3, 101.7, 56.1, 55.7.

IR (thin film) 3437, 3052, 2890, 2836, 1592, 1485, 1428, 1238, 1034, 934, 809, 737, 708 cm$^{-1}$.

HRMS (LD+) Calcd for C$_{33}$H$_{26}$N$_2$O$_3$ (M$^+$): 498.1943, Found: 498.1919.

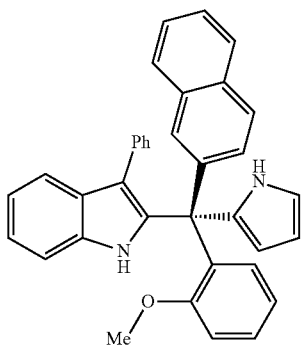

(S)-2-((2-Methoxyphenyl)(naphthalen-2-yl)(1H-pyrrol-2-yl)methyl)-3-phenyl-1H-indole (5r) was prepared as white foam from (2-methoxyphenyl) (naphthalen-2-yl)(3-phenyl-1H-indol-2-yl)methanol (91.1 mg, 0.2 mmol) and pyrrole (26.8 mg, 0.4 mmol) according to the General Procedure E (using 4 mL of DCM, 36 h) (eluent: hexanes/EtOAc=20:1-? 15:1) in 70% yield (70.6 mg, 95% ee).

$[\alpha]_D^{26}$:−15.0 (c=1.0, CHCl$_3$). HPLC analysis of the product: Daicel CHIRALPAK AD-H column; 10% i-PrOH in hexanes; 1.0 mL/min; retention times: 5.3 min (minor), 10.5 min (major).

$^1$H NMR (400 MHz, acetone-d$_6$) δ 9.52 (s, 1H), 9.40 (s, 1H), 7.78 (d, J=7.8 Hz, 1H), 7.74 (s, 1H), 7.64 (d, J=8.0 Hz, 1H), 7.60 (d, J=8.7 Hz, 1H), 7.45-7.34 (m, 3H), 7.32-7.16 (m, 3H), 7.11-7.08 (m, 1H), 7.00-6.96 (m, 2H), 6.94-6.73 (m, 7H), 6.69-6.64 (m, 1H), 6.02-5.98 (m, 1H), 5.89-5.87 (m, 1H), 3.18 (s, 3H).

$^{13}$C NMR (100 MHz, acetone-d$_6$) δ 158.9, 142.7, 137.8, 136.8, 135.6, 135.5, 134.8, 133.7, 133.0, 131.3, 131.1, 131.0, 129.82, 129.80, 129.2, 129.0, 128.0, 127.6, 126.8, 126.4, 126.3, 125.8, 122.1, 120.9, 119.9, 119.6, 118.3, 116.2, 113.5, 112.0, 110.5, 108.0, 56.3, 55.6.

IR (thin film) 3434, 3051, 2963, 2936, 1592, 1485, 1425, 1251, 1177, 1097, 1023, 809, 739, 706 cm$^{-1}$.

HRMS (LD+) Calcd for C$_{36}$H$_{28}$N$_2$O (M$^+$): 504.2202, Found: 504.2191.

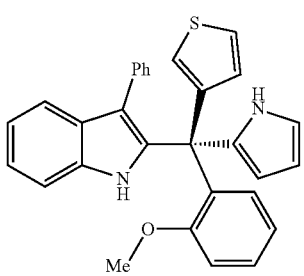

(R)-2-((2-Methoxyphenyl)(1H-pyrrol-2-yl)(thiophen-3-yl)methyl)-3-phenyl-1H-indole (5s) was prepared as white foam from (2-methoxyphenyl) (3-phenyl-1H-indol-2-yl)(thiophen-3-yl)methanol (82.3 mg, 0.2 mmol) and pyrrole (26.8 mg, 0.4 mmol) according to the General Procedure E (eluent: hexanes/EtOAc=20:1-? 15:1) in 31% yield (28.3 mg, 95% ee).

$[\alpha]_D^{26}$:−12.9 (c=1.0, CHCl$_3$). HPLC analysis of the product: Daicel CHIRALPAK AD-H column; 10% i-PrOH in hexanes; 1.0 mL/min; retention times: 6.3 min (minor), 13.0 min (major).

$^1$H NMR (400 MHz, acetone-d$_6$) δ 9.38 (s, 1H), 9.37 (s, 1H), 7.40 (d, J=8.1 Hz, 1H), 7.24 (d, J=8.0 Hz, 1H), 7.17-7.12 (m, 2H), 7.09-7.05 (m, 1H), 7.00-6.85 (m, 8H), 6.80-6.69 (m, 3H), 6.64-6.62 (m, 1H), 5.96 (q, J=2.8 Hz, 1H), 5.81-5.79 (m, 1H), 3.29 (s, 3H).

$^{13}$C NMR (100 MHz, acetone-d$_6$) δ 158.8, 145.8, 138.1, 136.7, 135.51, 135.46, 134.6, 131.2, 131.0, 130.9, 130.5, 129.7, 127.7, 125.8, 124.5, 124.2, 122.1, 120.8, 119.9, 119.6, 118.1, 115.4, 113.3, 111.9, 109.7, 107.9, 55.7, 53.1.

IR (thin film) 3417, 3051, 2927, 2841, 1590, 1544, 1481, 1425, 1290, 1242, 1095, 1025, 847, 801, 737, 704 cm$^{-1}$.

HRMS (LD+) Calcd for C$_{30}$H$_{24}$N$_2$OS (M$^+$): 460.1609, Found: 460.1605.

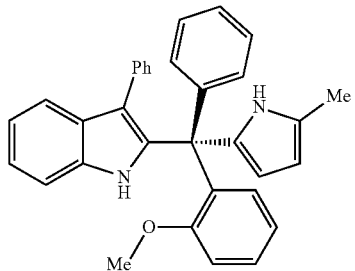

(S)-2-((2-Methoxyphenyl)(5-methyl-1H-pyrrol-2-yl)(phenyl)methyl)-3-phenyl-1H-indole (5t) was prepared as white foam from (2-methoxyphenyl) (phenyl)(3-phenyl-1H-indol-2-yl)methanol (89.2 mg, 0.22 mmol) and 2-methylpyrrole (16.2 mg, 0.2 mmol) according to the General Procedure E (using 4 mL of DCM, 24 h) (eluent: hexanes/EtOAc=20:1→15:1) in 95% yield (89.3 mg, 88% ee).

$[\alpha]_D^{26}$: −14.8 (c=1.0, CHCl$_3$). HPLC analysis of the product: Daicel CHIRALPAK OD-H column; 3% i-PrOH in hexanes; 1.0 mL/min; retention times: 5.5 min (minor), 6.3 min (major).

$^1$H NMR (400 MHz, acetone-d$_6$) δ 9.45 (s, 1H), 8.99 (s, 1H), 7.39 (d, J=8.1 Hz, 1H), 7.31-7.07 (m, 8H), 7.02-6.95 (m, 7H), 6.84-6.74 (m, 2H), 5.61-5.57 (m, 2H), 3.20 (s, 3H), 2.05 (s, 3H).

$^{13}$C NMR (100 MHz, acetone-d$_6$) δ 158.6, 145.6, 137.8, 136.7, 135.7, 135.5, 133.3, 131.09, 131.07, 130.8, 130.4, 129.6, 127.72, 127.69, 127.5, 126.7, 125.7, 122.12, 120.9, 119.8, 119.7, 116.3, 113.7, 111.8, 110.9, 105.7, 56.2, 55.6, 13.1.

IR (thin film) 3439, 3411, 3054, 2932, 2790, 1588, 1484, 1248, 1178, 1106, 1021, 743, 698 cm$^{-1}$.

HRMS (LD+) Calcd for C$_{33}$H$_{28}$N$_2$O (M$^+$): 468.2202, Found: 468.2213.

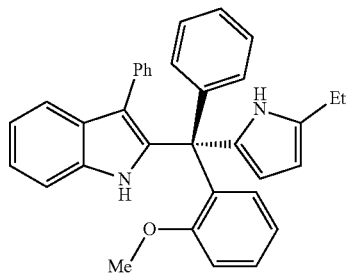

(S)-2-((5-Ethyl-1H-pyrrol-2-yl)(2-methoxyphenyl)(phenyl)methyl)-3-phenyl-1H-indole (5u) was prepared as white foam from (2-methoxyphenyl) (phenyl)(3-phenyl-1H-indol-2-yl)methanol (89.2 mg, 0.22 mmol) and 2-ethylpyrrole (19.0 mg, 0.2 mmol) according to the General Procedure E (using 4 mL of DCM, 36 h) (eluent: hexanes/EtOAc=20:1→15:1) in 93% yield (89.7 mg, 84% ee).

$[\alpha]_D^{26}$:−11.9 (c=1.0, CHCl$_3$). HPLC analysis of the product: Daicel CHIRALPAK AD-H column; 3% i-PrOH in hexanes; 1.0 mL/min; retention times: 4.8 min (minor), 5.7 min (major).

$^1$H NMR (400 MHz, acetone-d$_6$) δ 9.44 (s, 1H), 9.00 (s, 1H), 7.39 (d, J=8.1 Hz, 1H), 7.29 (d, J=1.9 Hz, 1H), 7.22-7.06 (m, 7H), 7.03-6.91 (m, 7H), 6.84-6.74 (m, 2H), 5.61 (s, 2H), 3.21 (s, 3H), 2.43 (q, J=7.6 Hz, 2H), 1.10 (t, J=7.5 Hz, 3H).

$^{13}$C NMR (100 MHz, acetone-d$_6$) δ 158.6, 145.6, 137.9, 136.7, 135.8, 135.5, 134.4, 133.2, 131.1 (2C), 130.8, 130.4, 129.6, 127.7, 127.5, 126.8, 125.7, 122.1, 120.9, 119.8, 119.7, 116.3, 113.7, 111.8, 110.8, 103.8, 56.3, 55.6, 21.2, 14.2.

IR (thin film) 3442, 3416, 3053, 2966, 2932, 2883, 1589, 1451, 1250, 1177, 1107, 1023, 740, 700 cm$^{-1}$.

HRMS (LD+) Calcd for C$_{34}$H$_{30}$N$_2$O (M$^+$): 482.2358, Found: 482.2339.

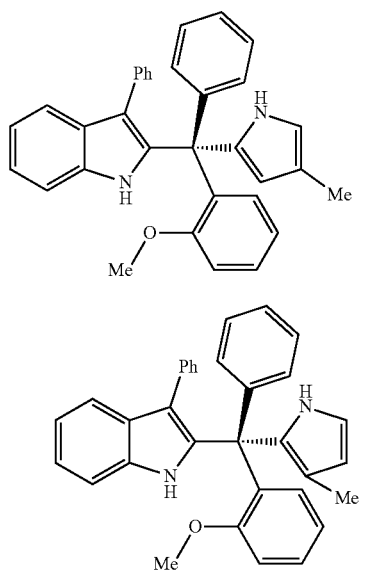

5v

5v'

(S)-2-((2-Methoxyphenyl)(4-methyl-1H-pyrrol-2-yl)(phenyl)methyl)-3-phenyl-1H-indole (5v) and (R)-2-((2-methoxyphenyl)(3-methyl-1H-pyrrol-2-yl) (phenyl)methyl)-3-phenyl-1H-indole (5v') were prepared as white foam from (2-methoxyphenyl)(phenyl)(3-phenyl-1H-indol-2-yl)methanol (89.2 mg, 0.22 mmol) and 3-methylpyrrole (32.4 mg, 0.4 mmol) according to the General Procedure E (using 4 mL of DCM, 36 h) (eluent: hexanes/EtOAc=20:1→15:1) in 90% yield (84.4 mg, 5v/5v' =6.7/1).

The pure sample of major product 5v for characterization was obtained by purifying through an achiral HPLC column. The analysis data for the major product 5v is as below.

$[\alpha]_D^{26}$:−4.4 (c=1.0, CHCl$_3$). HPLC analysis of the product: Daicel CHIRALPAK AD-H column; 5% i-PrOH in hexanes; 1.0 mL/min; retention times: 6.1 min (minor), 11.0 min (major).

$^1$H NMR (400 MHz, acetone-d$_6$) δ 9.43 (s, 1H), 8.95 (s, 1H), 7.39 (d, J=8.1 Hz, 1H), 7.25-7.04 (m, 9H), 6.97-6.93 (m, 5H), 6.88-6.82 (m, 2H), 6.78 (d, J=7.6 Hz, 1H), 6.69 (d, J=8.1 Hz, 1H), 6.37 (s, 1H), 5.61 (s, 1H), 3.18 (s, 3H), 1.95 (s, 3H).

$^{13}$C NMR (100 MHz, acetone-d$_6$) δ 158.7, 145.2, 137.8, 136.8, 135.5, 135.6, 135.2, 131.3, 131.00, 130.96, 130.7, 129.7, 127.7, 127.5, 126.8, 125.7, 122.1, 120.8, 119.8, 119.6, 117.7, 116.3, 116.2, 113.5, 112.3, 111.9, 56.3, 55.5, 12.3.

IR (thin film) 3416, 3053, 2927, 2867, 2542, 1589, 1483, 1449, 1242, 1178, 1110, 1023, 980, 803, 738, 698 cm$^{-1}$.

HRMS (LD+) Calcd for C$_{33}$H$_{28}$N$_2$O (M$^+$): 4.2202, Found: 468.2205.

Synthesis of the Triarylmethyl Alcohol Substrates

General Procedure A

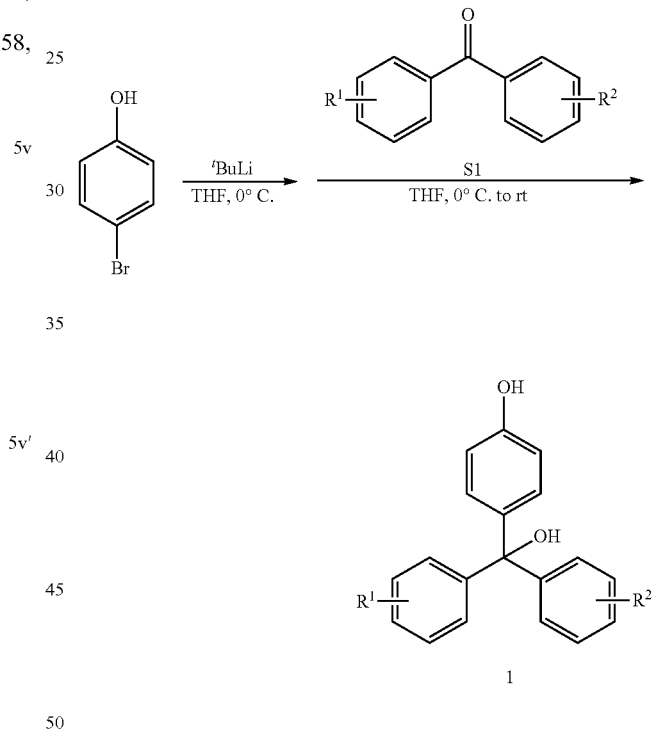

At 0° C., to a stirred solution of 4-bromophenol (0.78 g, 4.5 mmol) in THF (30 mL) was slowly added tert-butyllithium (1.6 M in pentane, 9.3 mL, 14.9 mmol). The resulting mixture was kept stirring at 0° C. for 2 h. Next, a solution of SI (3 mmol) (Ip, H.-W.; Ng, C.-F.; Chow, H.-F.; Kuck, D. J. Am. Chem. Soc. 2016, 138, 13778 13781. Ma, S.; Liu, J. X.; Li, S. H.; Chen, B.; Cheng, J. J.; Kuang, J. Q.; Liu, Y.; Wan, B. Q.; Wang, Y. L.; Ye, J. T.; Yu, Q.; Yuan, W. M.; Yu, S. C. Adv. Synth. Catal. 2011, 353, 1005-1017) in THF (10 mL) was added and the reaction mixture was kept stirring overnight. A saturated aqueous solution of NH$_4$Cl was added to quench the reaction. The reaction mixture was extracted with EtOAc (3×30 mL). The combined organic layers were dried over anhydrous Na$_2$SO$_4$, filtered, and concentrated. The residue was purified by silica gel flash chromatography to afford the pure tertiary alcohol 1.

General Procedure B

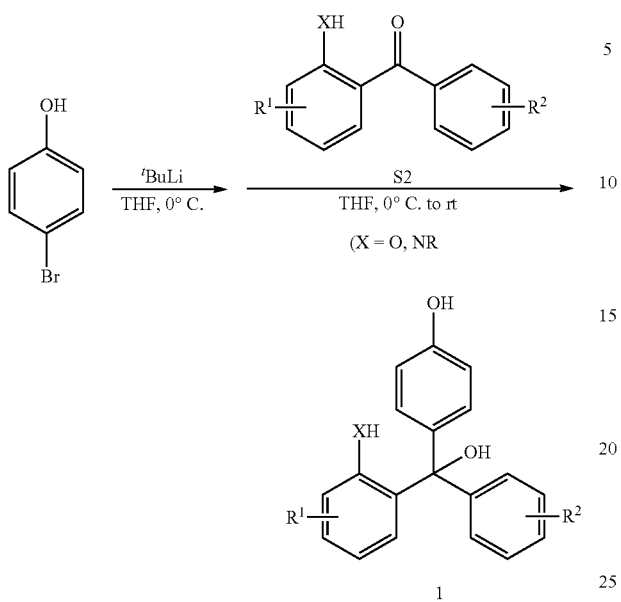

At 0° C., to a stirred solution of 4-bromophenol (1.30 g, 7.5 mmol) in THF (50 mL) was slowly added tert-butyllithium (1.6 M in pentane, 15.5 mL, 24.8 mmol). The resulting mixture was kept stirring at 0° C. for 2 h. After that, a solution of S2 (3 mmol) (Soldi, C.; Lamb, K. N.; Squitieri, R. A.; Gonzalez-López, M.; Maso, D.; M. J.; Shaw, J. T. *J. Am. Chem. Soc.* 2014, I36, 15142-15145.) in THF (10 mL) was added and the reaction mixture was kept stirring overnight. A saturated aqueous solution of NH$_4$Cl was added to quench the reaction. The reaction mixture was extracted with EtOAc (3×30 mL). The combined organic layers were dried over anhydrous Na$_2$SO$_4$, filtered, and concentrated. The residue was purified by silica gel flash chromatography to afford the pure tertiary alcohol 1.

General Procedure C

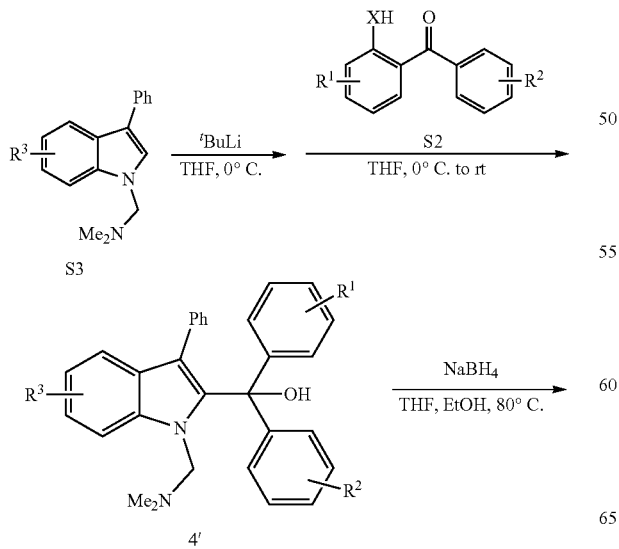

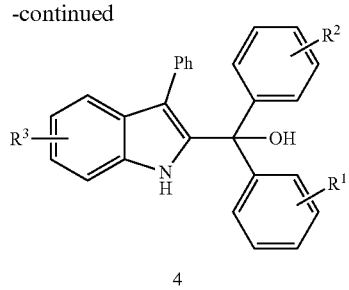

At 0° C., to a stirred solution of S3 (2 mmol) (Katritzky, A. R; Lue, P.; Chen, Y. X. *J. Org. Chem.* 1990, 55, 3688-3691) in THF (20 mL) was slowly added tert-butyllithium (1.6 M in pentane, 1.3 mL, 2.1 mmol). The resulting mixture was kept stirring at 0° C. for 0.5 h. After that, a solution of S2 (2 mmol) in THF (10 mL) was added and the reaction mixture was kept stirring at room temperature overnight. A saturated aqueous NH$_4$Cl solution was added to quench the reaction. The reaction mixture was extracted with EtOAc three times (3×30 mL). The combined organic layers were dried over anhydrous Na$_2$SO$_4$, filtered, and concentrated. The residue was purified by silica gel flash chromatography to afford the pure tertiary alcohol 4'.

To a solution of 4' in THF (3 mL) and ethanol (3 mL) was added NaBH$_4$ (2.2 mmol). The reaction mixture was heated to reflux for 3 h before it was cooled to room temperature. A saturated aqueous solution of NH$_4$Cl was added to quench the reaction. The reaction mixture was extracted with EtOAc three times (3×20 mL). The combined organic layers were dried over anhydrous Na$_2$SO$_4$, filtered, and concentrated. The residue was purified by silica gel flash chromatography to afford the pure tertiary alcohol 4.

What is claimed is:

1. An enantioselective method for preparing a tetraarylmethane, wherein the tetraarylmethane has Formula Ia:

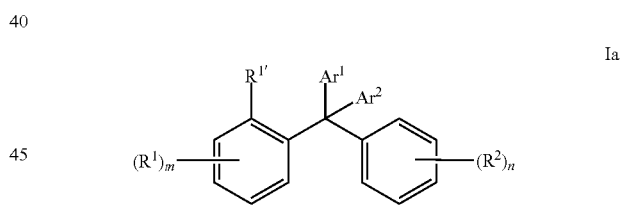

wherein
m is 0, 1, 2, or 3; n is 1, 2, 3, or 4;
p is 0, 1, 2, or 3;
t is 0, 1, 2, or 3;
Ar$^1$ is:

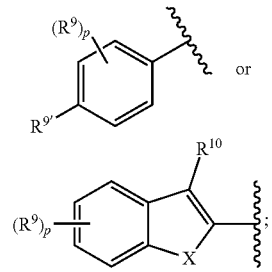

$Ar^2$ is:

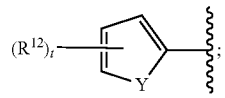

X is NH;
Y is NH;
$R^{1'}$ is selected from the group consisting of —$OR^3$, —$OSi(R^3)_3$, —$O(C=O)R^3$, —$O(C=O)OR^3$, —$N(R^4)_2$, —$N(R^4)(C=O)R^3$, —$N(R^4)(C=O)N(R^4)_2$, —$N(R^4)(C=O)OR^3$, —$O(C=O)N(R^4)_2$, —$SR^3$, —$N(R^4)SO_2R^3$, —$SeR^3$, —$P(R^3)_3$, and —$P(OR^3)_3$;

$R^1$ and $R^2$ are each independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —$OR^3$, —$OSi(R^3)_3$, —$O(C=O)R^3$, —$(C=O)OR^3$, —$O(C=O)OR^3$, —$(C=O)R^3$, —$N(R^4)_2$, —$N(R^4)(C=O)R^3$, —$(C=O)N(R^4)_2$, —$N(R^4)(C=O)N(R^4)_2$, —$N(R^4)(C=O)OR^3$, —$O(C=O)N(R^4)_2$, —$SR^3$, —$(S=O)R^3$, —$SO_2R^3$, —$SO_2N(R^4)_2$, —$N(R^4)SO_2R^3$, —$SeR^3$, —$P(R^3)_3$, —$P(OR^3)_3$, and —$(P=O)(OR^3)_3$; or two instances of $R^1$ taken together with the carbons to which they are attached form a 5-6 membered cycloalkyl, heterocycloalkyl, aryl, or heteroaryl; or two instances of $R^2$ taken together with the carbons to which they are attached form a 5-6 membered cycloalkyl, heterocycloalkyl, aryl, or heteroaryl;

$R^3$ is selected from the group consisting of hydrogen, alkyl, haloalkyl, perhaloalkyl, alkene, alkyne, cycloalkyl, heterocycloalkyl, aryl, araalkyl, and heteroaryl; and $R^4$ for each instance is independently selected from the group consisting of hydrogen, alkyl, haloalkyl, perhaloalkyl, alkene, alkyne, cycloalkyl, heterocycloalkyl, aryl, araalkyl, and heteroaryl; or two instances of $R^4$ taken together with the nitrogen to which they are attached form a 3-6 membered heterocycloalkyl; or one instance of $R^3$ and one instance of $R^4$ taken together with the atoms to which they are attached form a 4-6 membered heterocycloalkyl;

each $R^9$ is independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —$OR^3$, —$OSi(R^3)_3$, —$O(C=O)R^3$, —$(C=O)OR^3$, —$O(C=O)OR^3$, —$(C=O)R^3$, —$N(R^4)_2$, —$N(R^4)(C=O)R^3$, —$(C=O)N(R^4)_2$, —$N(R^4)(C=O)N(R^4)_2$, —$N(R^4)(C=O)OR^3$, —$O(C=O)N(R^4)_2$, —$SR^3$, —$(S=O)R^3$, —$SO_2R^3$, —$SO_2N(R^4)_2$, —$N(R^4)SO_2R^3$, —$SeR^3$, —$P(R^3)_3$, —$P(OR^3)_3$, and —$(P=O)(OR^3)_3$;

$R^{9'}$ is —OH;

$R^{10}$ is selected from the group consisting of alkyl, haloalkyl, perhaloalkyl, cycloalkyl, heterocycloalkyl, aryl, araalkyl, heteroaryl, and halide; and each $R^{12}$ is independently selected from the group consisting of hydrogen, alkyl, haloalkyl, perhaloalkyl, alkene, alkyne, cycloalkyl, heterocycloalkyl, aryl, araalkyl, heteroaryl, halide, azide, —$OR^3$, —$OSi(R^3)_3$, —$O(C=O)R^3$, —$O(C=O)OR^3$, —$N(R^4)_2$, —$N(R^4)(C=O)R^3$, —$N(R^4)(C=O)N(R^4)_2$, —$N(R^4)(C=O)OR^3$, —$O(C=O)N(R^4)_2$, —$SR^3$, —$N(R^4)SO_2R^3$, —$SeR^3$, —$P(R^3)_3$, and —$P(OR^3)_3$; or two instances of $R^{12}$ taken together with the carbons to which they are attached form a 5-6 membered cycloalkyl, heterocycloalkyl, aryl, or heteroaryl; and the method comprises:

contacting a compound of Formula IIa, wherein the compound of Formula IIa is

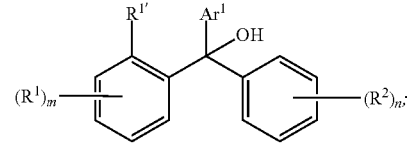

wherein $Ar^1$ is selected from the group consisting of:

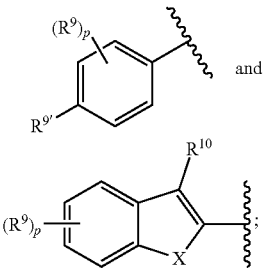

m is 0, 1, 2, or 3;
n is 1, 2, 3, or 4;
p is 0, 1, 2, or 3;
X is NH;
$R^{1'}$ is selected from the group consisting of —$OR^3$, —$OSi(R^3)_3$, —$O(C=O)R^3$, —$O(C=O)OR^3$, —$N(R^4)_2$, —$N(R^4)(C=O)R^3$, —$N(R^4)(C=O)N(R^4)_2$, —$N(R^4)(C=O)OR^3$, —$O(C=O)N(R^4)_2$, —$SR^3$, —$N(R^4)SO_2R^3$, —$SeR^3$, —$P(R^3)_3$, and —$P(OR^3)_3$;
each $R^9$ is independently selected from the group consisting of hydrogen, alkyl, haloalkyl, perhaloalkyl, alkene, alkyne, cycloalkyl, heterocycloalkyl, aryl, araalkyl, heteroaryl, halide, cyanide, nitro, azide, —$OR^3$, —$OSi(R^3)_3$, —$O(C=O)R^3$, —$(C=O)OR^3$, —$O(C=O)OR^3$, —$(C=O)R^3$, —$N(R^4)_2$, —$N(R^4)(C=O)R^3$, —$(C=O)N(R^4)_2$, —$N(R^4)(C=O)N(R^4)_2$, —$N(R^4)(C=O)OR^3$, —$O(C=O)N(R^4)_2$, —$SR^3$, —$(S=O)R^3$, —$SO_2R^3$, —$SO_2N(R^4)_2$, —$N(R^4)SO_2R^3$, —$SeR^3$, —$P(R^3)_3$, —$P(OR^3)_3$, and —$(P=O)(OR^3)_3$;
$R^{9'}$ is —OH; and
$R^{10}$ is selected from the group consisting of alkyl, haloalkyl, perhaloalkyl, cycloalkyl, heterocycloalkyl, aryl, araalkyl, heteroaryl, and halide;
with a heteroaromatic nucleophile in the presence of a chiral Brønsted acid under conditions that facilitate an electrophilic aromatic substitution reaction thereby forming the compound of Formula Ia, wherein the heteroaromatic nucleophile is represented by the Formula IV:

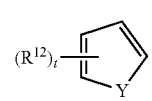

IV wherein
t is 0, 1, 2, or 3;
Y is NH; and each $R^{12}$ is independently selected from the group consisting of hydrogen, alkyl, haloalkyl, perhaloalkyl, alkene, alkyne, cycloalkyl, heterocycloalkyl, aryl, araalkyl, heteroaryl, halide, azide, —$OR^3$, —$OSi(R^3)_3$, —$O(C=O)R^3$, —$O(C=O)OR^3$, —$N(R^4)_2$, —$N(R^4)(C=O)R^3$, —$N(R^4)(C=O)N(R^4)_2$, —$N(R^4)(C=O)OR^3$, —$O(C=O)N(R^4)_2$, —$SR^3$, —$N(R^4)SO_2R^3$, —$SeR^3$, —$P(R^3)_3$, and —$P(OR^3)_3$; or two instances of $R^{12}$ taken together with the carbons to which they are attached form a 5-6 membered cycloalkyl, heterocycloalkyl, aryl, or heteroaryl; and the chiral Brønsted acid is a chiral phosphoric acid represented by Formula IIIa, Formula IIIb, or Formula IIId:

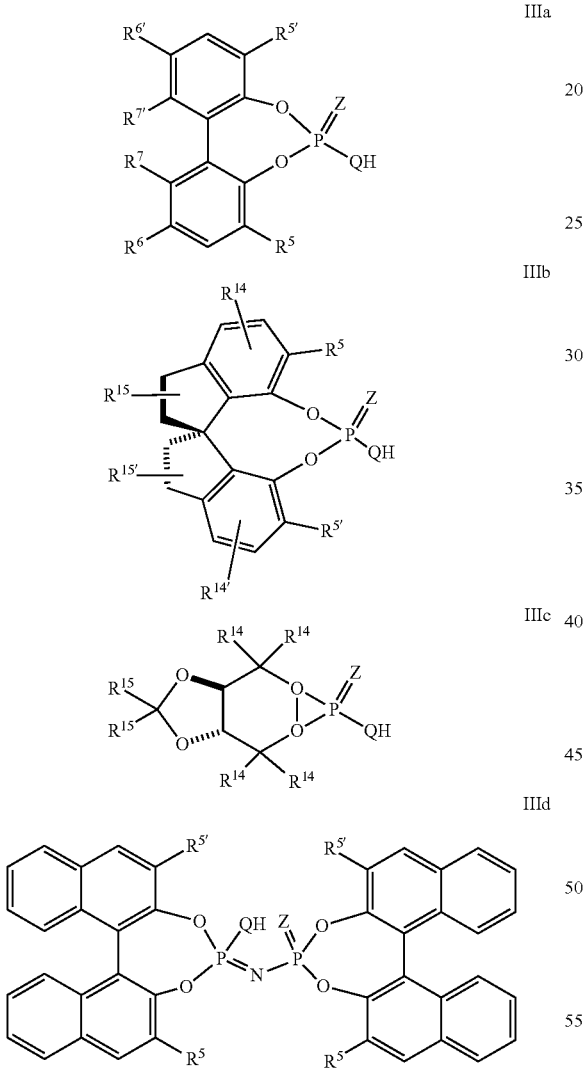

wherein
Q is O, S, or $NSO_2R^{16}$;
Z is O, S, or Se;
each of $R^5$ and $R^{5'}$ is independently hydrogen, alkyl, haloalkyl, perhaloalkyl, cycloalkyl, heterocycloalkyl, aryl, araalkyl, heteroaryl, halide, or triarylsilane;
each of $R^6$ and $R^{6'}$ is independently hydrogen, alkyl, haloalkyl, perhaloalkyl, cycloalkyl, heterocycloalkyl, aryl, araalkyl, heteroaryl, halide, or trialkylsilane;

each of $R^7$ and $R^{7'}$ is independently alkyl, haloalkyl, perhaloalkyl, cycloalkyl, heterocycloalkyl, aryl, araalkyl, heteroaryl, halide, or trialkylsilane; or $R^{6'}$ and $R^{7'}$ taken together with the carbons to which they are attached form 5-6 membered cycloalkyl or 6 membered aryl and $R^6$ and $R^7$ taken together with the carbons to which they are attached form 5-6 membered cycloalkyl or 6 membered aryl;

each of $R^{14}$ and $R^{14'}$ is independently hydrogen, alkyl, haloalkyl, perhaloalkyl, cycloalkyl, heterocycloalkyl, aryl, araalkyl, heteroaryl, halide, or trialkylsilane;

each of $R^{15}$ and $R^{15'}$ is independently hydrogen, alkyl, haloalkyl, perhaloalkyl, cycloalkyl, heterocycloalkyl, aryl, araalkyl, heteroaryl, halide, or trialkylsilane; and $R^{16}$ is alkyl or aryl.

2. The method of claim 1, wherein the chiral phosphoric acid is represented by the Formula IIIe:

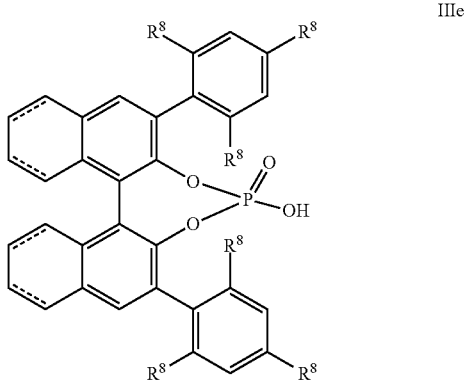

wherein $R^8$ is alkyl, cycloalkyl, or aryl.

3. The method of claim 2, wherein $R^8$ is isopropyl, cyclohexyl, or phenyl.

4. The method of claim 1, wherein each $R^{12}$ is independently selected from the group consisting of hydrogen, alkyl, haloalkyl, perhaloalkyl, alkene, alkyne, cycloalkyl, heterocycloalkyl, aryl, araalkyl, heteroaryl, halide, azide, —$OR^3$, —$OSi(R^3)_3$, —$O(C=O)R^3$, —$O(C=O)OR^3$, —$N(R^4)_2$, —$N(R^4)(C=O)R^3$, —$N(R^4)(C=O)N(R^4)_2$, —$N(R^4)(C=O)OR^3$, —$O(C=O)N(R^4)_2$, —$SR^3$, —$N(R^4)SO_2R^3$, and —$SeR^3$; or two instances of $R^{12}$ taken together with the carbons to which they are attached form a 6 membered cycloalkyl or aryl.

5. The method of claim 1, wherein m is 0 or 1; $R^{1'}$ is —$OR^3$, —$OSi(R^3)_3$, —$O(C=O)R^3$, —$O(C=O)OR^3$, or —$O(C=O)N(R^4)_2$,
and the heteroaromatic nucleophile is selected from: wherein

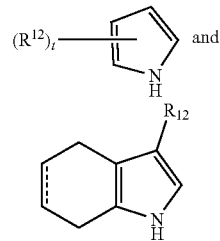

t is 0 or 1; and

R$^{12}$ is selected from the group consisting of hydrogen, alkyl, haloalkyl, perhaloalkyl, alkene alkyne, cycloalkyl, heterocycloalkyl, aryl, araalkyl, heteroaryl, halide, azide, —OR$^3$, —OSi(R$^3$)$_3$, —O(C=O)R$^3$, —O(C=O)OR$^3$, —N(R$^4$)$_2$, —N(R$^4$)(C=O)R$^3$, —N(R$^4$)(C=O)N(R$^4$)$_2$, —N(R$^4$)(C=O)OR$^3$, —O(C=O)N(R$^4$)$_2$, —SR$^3$, —N(R$^4$)SO$_2$R$^3$, —SeR$^3$, —P(R$^3$)$_3$, and —P(OR$^3$)$_3$.

6. The method of claim 5, wherein the chiral Brønsted acid is represented by the Formula IIIf or Formula IIIg:

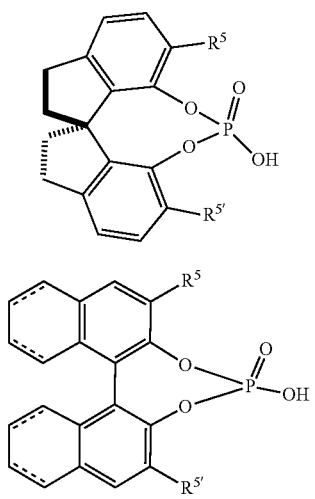

wherein each of R$^5$ and R$^{5'}$ is alkyl, aryl, or triarylsilane.

7. The method of claim 6, wherein each of R$^5$ and R$^{5'}$ is 2,4,6-(iPr)$_3$C$_6$H$_2$—, 2,4,6-Cy$_3$C$_6$H$_2$—, 1-napthyl, 9-anthryl, 9-phenanthryl, or 1-pyrene.

8. The method of claim 1, wherein the step of contacting the compound of Formula IIa with the heteroaromatic nucleophile in the presence of the chiral Brønsted acid occurs in a solvent selected from the group consisting of chlorobenzene, PhCF$_3$, PhF, CCl$_4$, CH$_2$Cl$_2$ (DCM), CHCl$_3$, PhMe, and ClCH$_2$CH$_2$Cl (DCE).

9. The method of claim 1, wherein the chiral Brønsted acid is present at a mole concentration of between 0.1% and 25% relative to the compound of Formula IIa.

10. The method of claim 1, wherein the step of contacting the compound of Formula IIa with the heteroaromatic nucleophile in the presence of the chiral Brønsted acid occurs at a temperature between −30° C. and 40° C.

11. The method of claim 1, wherein the tetraarylmethane having Formula Ia is prepared with an enantiomeric excess (ee) between 40 to 99.9%.

12. The method of claim 4, wherein the tetraarylmethane having Formula Ia is prepared with an ee of 80 to 97%.

13. The method of claim 1, wherein the compound of Formula IIa is a racemic mixture.

* * * * *